(12) United States Patent
Burkhart et al.

(10) Patent No.: US 10,487,262 B2
(45) Date of Patent: Nov. 26, 2019

(54) MATERIALS FOR ORGANIC ELECTROLUMINESCENT DEVICES

(71) Applicant: Merck Patent GmbH, Darmstadt (DE)

(72) Inventors: Beate Burkhart, Darmstadt (DE); Holger Heil, Frankfurt am Main (DE); Lara-Isabel Rodriguez, Darmstadt (DE); Sebastian Meyer, Aschaffenburg (DE); Amandine Darsy, Frankfurt am Main (DE); Rouven Linge, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 15/560,575

(22) PCT Filed: Feb. 26, 2016

(86) PCT No.: PCT/EP2016/000340
§ 371 (c)(1),
(2) Date: Sep. 22, 2017

(87) PCT Pub. No.: WO2016/150544
PCT Pub. Date: Sep. 29, 2016

(65) Prior Publication Data
US 2018/0051206 A1    Feb. 22, 2018

(30) Foreign Application Priority Data

Mar. 25, 2015 (EP) .................... 15000876

(51) Int. Cl.
| | | |
|---|---|---|
| *H01L 51/50* | (2006.01) | |
| *C09K 11/06* | (2006.01) | |
| *H01L 51/00* | (2006.01) | |
| *C07C 13/62* | (2006.01) | |
| *C07D 207/323* | (2006.01) | |
| *C07D 209/44* | (2006.01) | |
| *C07D 307/36* | (2006.01) | |
| *C07D 333/08* | (2006.01) | |
| *C09K 11/02* | (2006.01) | |

(52) U.S. Cl.
CPC .............. *C09K 11/06* (2013.01); *C07C 13/62* (2013.01); *C07D 207/323* (2013.01); *C07D 209/44* (2013.01); *C07D 307/36* (2013.01); *C07D 333/08* (2013.01); *C09K 11/025* (2013.01); *H01L 51/0054* (2013.01); *H01L 51/0056* (2013.01); *H01L 51/0058* (2013.01); *H01L 51/0065* (2013.01); *H01L 51/0067* (2013.01); *H01L 51/0068* (2013.01); *H01L 51/0072* (2013.01); *C07C 2603/54* (2017.05); *C09K 2211/1007* (2013.01); *C09K 2211/1011* (2013.01); *C09K 2211/1018* (2013.01); *H01L 51/001* (2013.01); *H01L 51/0003* (2013.01); *H01L 51/0085* (2013.01); *H01L 51/5012* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 51/5096* (2013.01); *Y02E 10/549* (2013.01)

(58) Field of Classification Search
None
See application file for complete search history.

(56) References Cited

U.S. PATENT DOCUMENTS

| | | |
|---|---|---|
| 2009/0184313 A1 | 7/2009 | Buesing et al. |
| 2009/0261717 A1 | 10/2009 | Buesing et al. |
| 2010/0176716 A1 | 7/2010 | Igawa et al. |
| 2011/0092701 A1 | 4/2011 | Pflumm et al. |
| 2011/0108821 A1 | 5/2011 | Kaiser et al. |
| 2012/0172597 A1 | 7/2012 | Fortte et al. |
| 2013/0053558 A1 | 2/2013 | Pflumm et al. |
| 2015/0329772 A1 | 11/2015 | Heil et al. |

FOREIGN PATENT DOCUMENTS

| | | | |
|---|---|---|---|
| DE | 102006025846 A1 | 6/2007 | |
| DE | 102009033371 A1 | 12/2011 | |
| JP | 2002-069044 | * 3/2002 | ............. C09K 11/06 |
| JP | 2005082532 A | 3/2005 | |
| JP | 2007220904 A | 8/2007 | |
| WO | 2007114038 A1 | 10/2007 | |
| WO | 2008006449 A1 | 1/2008 | |
| WO | 2009141026 A1 | 11/2009 | |
| WO | 2010012328 A1 | 2/2010 | |
| WO | 2011057701 A1 | 5/2011 | |
| WO | 2014106522 A1 | 7/2014 | |

OTHER PUBLICATIONS

Li, et al., "Full Emission Color Tuning in Bis-Dipolar Diphenylamino-Endcapped Oligoarylfluorenes," Chem. Mater., vol. 17, pp. 5032-5040 (2005).
Zhan, et al., "Substituent effects on the electronic structure of siloles," Chem. Commun., pp. 1948-1955 (2009).
Liu, et al., "Theoretical study of optical and electronic properties of the bis-dipolar diphenylamino-endcapped oligoarylfluorenes as promising light emitting materials," J. Phys. Org. Chem., vol. 20, pp. 600-609 (2007).
Chen, et al., "2,5-Difluorenyl-Substituted Siloles for the Fabrication of High-Performance Yellow Organic Light-Emitting Diodes," Chem. Eur. J., vol. 20, pp. 1931-1939 (2014).

(Continued)

*Primary Examiner* — Gregory D Clark
(74) *Attorney, Agent, or Firm* — Kim IP Law Group PLLC

(57) ABSTRACT

The present invention relates to a compound of formula (I) or (II), which is suitable for use as functional material in an electronic device, in particular as emitter material in an organic electroluminescent device.

16 Claims, No Drawings

(56) References Cited

OTHER PUBLICATIONS

Promarak, et al., "Synthesis and characterization of N-carbazole end-capped oligofluorene-thiophenes," Tetrahedron, vol. 63, pp. 8881-8890 (2007).
Wong, et al., "Synthesis and Properties of Novel Thiophene-Based Conjugated Homologues: 9,9-Diphenylfluorene-Capped Oligothiophenes," Org. Lett., vol. 4, No. 25, pp. 4439-4442 (2002).

* cited by examiner

MATERIALS FOR ORGANIC ELECTROLUMINESCENT DEVICES

CROSS-REFERENCE TO RELATED APPLICATIONS

This patent application is a U.S. national stage application, filed pursuant to 35 U.S.C. § 371, of PCT Application No. PCT/EP2016/000340, filed Feb. 26, 2016, which claims priority to European Patent Application No. 15000876.1, filed Mar. 25, 2015, both of which are incorporated by reference herein in their entireties.

The present invention relates to a compound of a formula (I) or (II). The compound is suitable for use as functional material in an electronic device, in particular an organic electroluminescent device (OLED). The invention furthermore relates to certain embodiments of electronic devices comprising the compound of the formula (I) or (II), and to a process for the preparation of the compound of the formula (I) or (II).

In accordance with the present invention, the term electronic device is taken to mean in general electronic devices which comprise organic materials. These are preferably taken to mean OLEDs and some further embodiments of electronic devices comprising organic materials which are disclosed later in the application.

The general structure and principle of functioning of OLEDs are known to the person skilled in the art and is described, inter alia, in U.S. Pat. Nos. 4,539,507, 5,151,629, EP 0676461 and WO 1998/27136.

With respect to the performance data of the electronic devices, further improvements are necessary, in particular with a view to broad commercial use, for example in displays or as light sources. Of particular importance in this connection are the lifetime, the efficiency and the operating voltage of the electronic devices and the colour values achieved.

In particular in the case of blue-emitting OLEDs, there is potential for improvement with respect to the lifetime of the devices and the colour values achieved for the emitted light. An important starting point for achieving the said improvements is the choice of the emitter compound employed in the electronic device.

Blue-fluorescent emitters known from the prior art are a multiplicity of compounds, in particular arylamines containing one or more condensed aryl groups and/or indenofluorene groups. Examples thereof are the pyrene-arylamines disclosed in U.S. Pat. No. 5,153,073 and the pyrene-arylamines disclosed in WO 2012/048780. Further examples of arylamine emitters are benzo-indenofluorenamines, for example in accordance with WO 2008/006449 or WO 2008/003464, and dibenzoindenofluorenamines, for example in accordance with WO 2007/140847.

Furthermore, the use of fluorenamines which contain aromatic groups condensed onto the fluorene system is known in the prior art. The compounds which contain two or more arylamino groups are employed as fluorescent emitters (US 2012/0161615). However, the compounds exhibit green to green-blue emission and not blue emission.

Furthermore, KR 2009/131536 and WO 2004/061048 disclose benzofluorene derivatives which carry a diphenylamino group. However, compounds of this type have excessively short-wave emission to be used as blue-fluorescent emitters, or their efficiency and lifetime are unsatisfactory on use in OLEDs.

In summary, the technical object is thus to provide deep-blue-fluorescent emitters which preferably have a narrow emission band. The object is furthermore preferably to provide compounds with which high power efficiency can be achieved and with which deep-blue emission of the electronic device can be achieved and at the same time, which exhibit an improved lifetime.

Surprisingly, it has now been found that compounds comprising at least two groups selected from benzindenofluorenyl derivatives or benzofluorenyl derivatives which are connected to a five-membered ring have deep-blue colour coordinates, a very narrow emission spectrum and exhibit at the same time a significantly improved lifetime. Consequently, these compounds achieve the technical object presented above. Deep-blue colour coordinates in the case of emitter compounds are highly desirable for use in displays and lighting applications. In particular in the case of blue-emitting compounds, a narrow emission spectrum, i.e. an emission band having a small width, is highly desirable for tuning the colour impressions of the various colours in a display or in the case of a lighting application. At the same time, there continues to be a demand for blue-emitting compounds, which result in good efficiencies and at the same time in improved lifetimes in organic electronic devices.

The invention thus relates to a compound of formula (I) or formula (II):

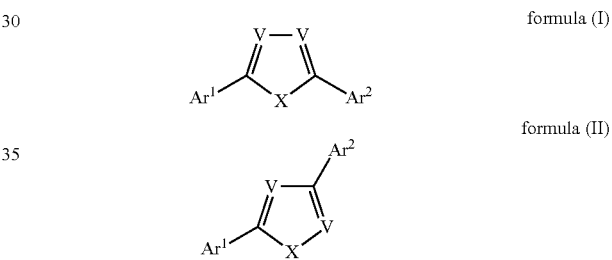

where

X is selected from the group consisting of $C(R^1)_2$, $Si(R^1)_2$, $Ge(R^1)_2$, O, S, $NR^1$ and Se;

V is, on each occurrence, identically or differently, selected from the group consisting of N or $CR^2$;

$Ar^1$, $Ar^2$ is, identically or differently, selected from one of the following formulae (3) to (8):

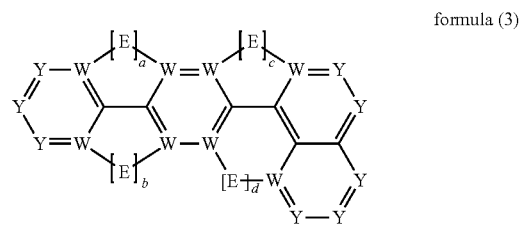

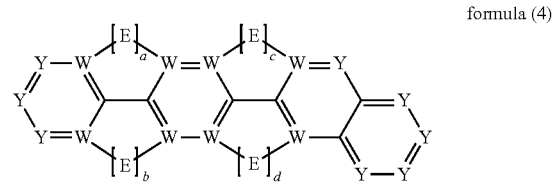

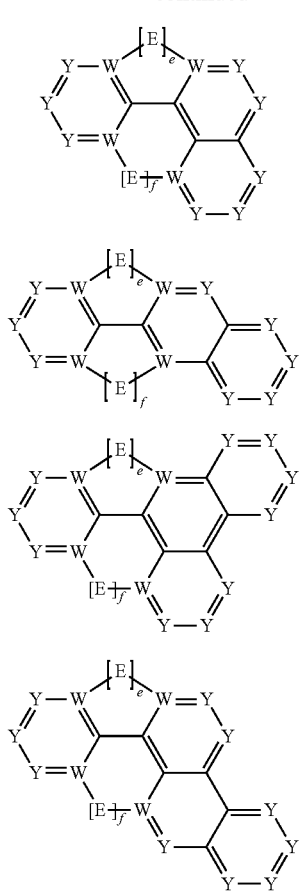

formula (5)

formula (6)

formula (7)

formula (8)

where Ar¹ and Ar² are connected to the 5-membered ring of formula (I) or (II) via one group Y of one of the formulae (3) to (8);

Y is equal to C if the 5-membered ring of formula (I) or (II) is bonded to Y and is equal $CR^3$ or N if the 5-membered ring of formula (I) or (II) is not bonded to the group Y;

E is on each occurrence, identically or differently, a divalent bridge selected from $B(R^1)$, $C(R^1)_2$, $Si(R^1)_2$, $C=O$, $C=NR^1$, $C=C(R^1)_2$, O, S, S=O, $SO_2$, $N(R^1)$, $P(R^1)$ and $P(=O)R^1$;

W is equal to C if a bridge E is bonded to the group W and is equal to $CR^3$ or N if no bridge E is bonded to the group W;

$R^1$, $R^2$, $R^3$ is on each occurrence, identically or differently, H, D, F, Br, Cl, I, $C(=O)R^4$, CN, $Si(R^4)_3$, $N(R^4)_2$, $P(=O)(R^4)_2$, $S(=O)R^4$, $S(=O)_2R^4$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals $R^4$ and where one or more $CH_2$ groups in the above-mentioned groups may be replaced by $-R^4C=CR^4-$, $-C\equiv C-$, $Si(R^4)_2$, $C=O$, $C=NR^4$, $-C(=O)O-$, $-C(=O)NR^4-$, $NR^4$, $P(=O)(R^4)$, $-O-$, $-S-$, SO or $SO_2$, or an aromatic or heteroaromatic ring system having 5 to 30 aromatic ring atoms, which may in each case be substituted by one or more radicals $R^4$, or an aryloxy or heteroaryloxy group having 5 to 30 aromatic ring atoms, which may be substituted by one or more radicals $R^4$, where two or more substituents $R^1$, two or more substituents $R^2$, or two or more substituents $R^3$ may be linked to one another and may form a ring;

$R^4$ is on each occurrence, identically or differently, H, D, F, Br, Cl, I, $C(=O)R^5$, CN, $Si(R^5)_3$, $N(R^5)_2$, $P(=O)(R^5)_2$, $S(=O)R^5$, $S(=O)_2R^5$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals $R^5$ and where one or more $CH_2$ groups in the above-mentioned groups may be replaced by $-R^5C=CR^5-$, $-C\equiv C-$, $Si(R^5)_2$, $C=O$, $C=NR^5$, $-C(=O)O-$, $-C(=O)NR^5-$, $NR^5$, $P(=O)(R^5)$, $-O-$, $-S-$, SO or $SO_2$, or an aromatic or heteroaromatic ring system having 5 to 30 aromatic ring atoms, which may in each case be substituted by one or more radicals $R^5$, or an aryloxy or heteroaryloxy group having 5 to 30 aromatic ring atoms, which may be substituted by one or more radicals $R^5$, where two or more radicals $R^4$ may be linked to one another and may form a ring;

$R^5$ is on each occurrence, identically or differently, H, D, F or an aliphatic, aromatic or heteroaromatic organic radical having 1 to 20 C atoms, in which, in addition, one or more H atoms may be replaced by D or F;

a, b, c, d, e, f is on each occurrence, identically or differently, 0 or 1, with the proviso that a+b=1 or 2, c+d=1 or 2 and e+f=1 or 2, where a=0 or b=0 or c=0 or d=0 or e=0 or f=0 in each case means that the corresponding bridge X is not present.

For the purposes of the present application, the following definitions of chemical groups apply:

An aryl group in the sense of this invention contains 6 to 60 aromatic ring atoms; a heteroaryl group in the sense of this invention contains 5 to 60 aromatic ring atoms, at least one of which is a heteroatom. The heteroatoms are preferably selected from N, O and S. This represents the basic definition. If other preferences are indicated in the description of the present invention, for example with respect to the number of aromatic ring atoms or the heteroatoms present, these apply.

An aryl group or heteroaryl group here is taken to mean either a simple aromatic ring, i.e. benzene, or a simple heteroaromatic ring, for example pyridine, pyrimidine or thiophene, or a condensed (annellated) aromatic or heteroaromatic polycycle, for example naphthalene, phenanthrene, quinoline or carbazole. A condensed (annellated) aromatic or heteroaromatic polycycle in the sense of the present application consists of two or more simple aromatic or heteroaromatic rings condensed with one another.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aryloxy group in accordance with the definition of the present invention is taken to mean an aryl group, as defined above, which is bonded via an oxygen atom. An analogous definition applies to heteroaryloxy groups.

An aromatic ring system in the sense of this invention contains 6 to 60 C atoms in the ring system. A heteroaromatic ring system in the sense of this invention contains 5 to 60 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an $sp^3$-hybridised C, Si, N or O atom, an $sp^2$-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, such as, for example, systems such as biphenyl, terphenyl or diphenyltriazine.

An aromatic or heteroaromatic ring system having 5-60 aromatic ring atoms, which may in each case also be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or $CH_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The formulation that two or more radicals may form a ring with one another is, for the purposes of the present application, intended to be taken to mean, inter alia, that the two radicals are linked to one another by a chemical bond. This is illustrated by the following schemes:

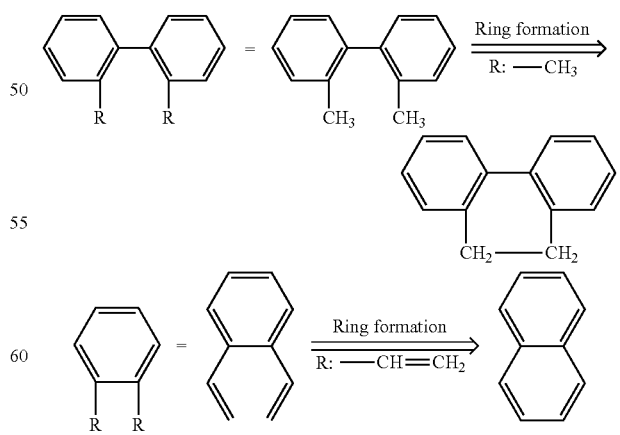

Furthermore, however, the above-mentioned formulation is also intended to be taken to mean that, in the case where one of the two radicals represents hydrogen, the second radical is bonded at the position to which the hydrogen atom was bonded, with formation of a ring. This is illustrated by the following scheme:

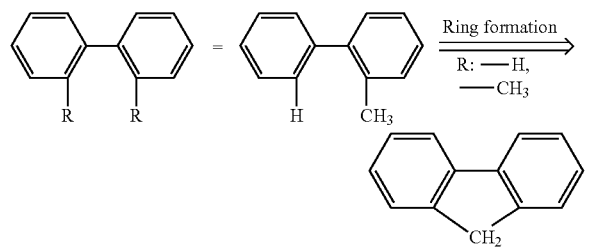

In accordance with a preferred embodiment, X is selected from $C(R^1)_2$, $Si(R^1)_2$, O or S, more preferably from $Si(R^1)_2$, O or S. In a very particular preferred embodiment, X is equal to 0.

It is furthermore preferred for V to be equal to $CR^2$.

In a particularly preferred embodiment, the compound is a compound of formula (I), where two groups V are equal to $CR^2$, and two radicals $R^2$ are linked to one another and form an aliphatic or an aromatic ring.

In a very particularly preferred embodiment, the compound is a compound of formula (I), where two groups V are equal to $CR^2$, and two radicals $R^2$ form a phenyl group, which is condensed on the 5-membered ring in order to form a compound of formula (I-1):

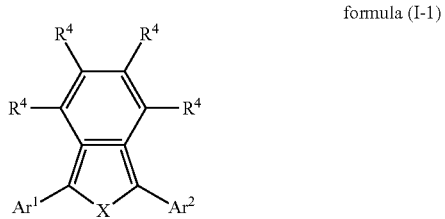

formula (I-1)

where $Ar^1$, $Ar^2$, X and $R^4$ have the same meaning as above.

In accordance with a further preferred embodiment, E is selected from $C(R^1)_2$, $Si(R^1)_2$, O, S, $N(R^1)$, more preferably $C(R^1)_2$.

It is furthermore preferred that the group Y is equal to C if the 5-membered ring of formula (I) or (II) is bonded to Y and is equal to $CR^3$ if the 5-membered ring of formula (I) or (II) is not bonded to Y.

In accordance with a further preferred embodiment, a+b=1 and c+d=1 in formulae (3) and (4) and e+f=1 or 2 in formulae (5), (6), (7) and (8).

The radical $R^1$ is preferably on each occurrence, identically or differently, H, D, F, CN, $Si(R^4)_3$, $N(R^4)_2$, a straight-chain alkyl or alkoxy group having 1 to 10 C atoms or a branched or cyclic alkyl or alkoxy group having 3 to 10 C atoms, where the above-mentioned groups may each be substituted by one or more radicals $R^4$ and where one or more $CH_2$ groups in the above-mentioned groups may be replaced by —C≡C—, —$R^4$C=$CR^4$—, $Si(R^4)_2$, C=O, C=$NR^4$, —$NR^4$—, —O—, —S—, —C(=O)O— or —C(=O)$NR^4$—, or an aromatic or heteroaromatic ring system having 5 to 20 aromatic ring atoms, which may in each case be substituted by one or more radicals $R^4$, where two radicals $R^1$ may be linked to one another and may form a ring.

More preferably, $R^1$ is selected from H, a straight-chain alkyl group having 1 to 10 C atoms or a branched or cyclic alkyl group having 3 to 10 C atoms or an aromatic or heteroaromatic ring system having 5 to 20 aromatic ring atoms, which may in each case be substituted by one or more radicals $R^4$.

The radical $R^2$ is preferably on each occurrence, identically or differently, H, D, F, CN, $Si(R^4)_3$, $N(R^4)_2$, a straight-chain alkyl or alkoxy group having 1 to 10 C atoms or a branched or cyclic alkyl or alkoxy group having 3 to 10 C atoms, where the above-mentioned groups may each be substituted by one or more radicals $R^4$ and where one or more $CH_2$ groups in the above-mentioned groups may be replaced by —C≡C—, —$R^4$C=$CR^4$—, $Si(R^4)_2$, C=O, C=$NR^4$, —$NR^4$—, —O—, —S—, —C(=O)O— or —C(=O)$NR^4$—, or an aromatic or heteroaromatic ring system having 5 to 20 aromatic ring atoms, which may in each case be substituted by one or more radicals $R^4$; where two radicals $R^2$ may be linked to one another and may form a ring.

More preferably, $R^2$ is selected from H, a straight-chain alkyl group having 1 to 10 C atoms or a branched or cyclic alkyl group having 3 to 10 C atoms or an aromatic or heteroaromatic ring system having 5 to 20 aromatic ring atoms, which may in each case be substituted by one or more radicals $R^4$; where two radicals $R^2$ may be linked to one another and may form a ring.

The radical $R^3$ is preferably on each occurrence, identically or differently, H, D, F, CN, $Si(R^4)_3$, $N(R^4)_2$, a straight-chain alkyl or alkoxy group having 1 to 10 C atoms or a branched or cyclic alkyl or alkoxy group having 3 to 10 C atoms, where the above-mentioned groups may each be substituted by one or more radicals $R^4$ and where one or more $CH_2$ groups in the above-mentioned groups may be replaced by —C≡C—, —$R^4$C=$CR^4$—, $Si(R^4)_2$, C=O, C=$NR^4$, —$NR^4$—, —O—, —S—, —C(=O)O— or —C(=O)$NR^4$—, or an aromatic or heteroaromatic ring system having 5 to 20 aromatic ring atoms, which may in each case be substituted by one or more radicals $R^4$, where two radicals $R^3$ may be linked to one another and may form a ring.

More preferably, $R^3$ is selected from H, a straight-chain alkyl group having 1 to 10 C atoms or a branched or cyclic alkyl group having 3 to 10 C atoms or an aromatic or heteroaromatic ring system having 5 to 20 aromatic ring atoms, which may in each case be substituted by one or more radicals $R^4$.

The radical $R^4$ is preferably on each occurrence, identically or differently, H, D, F, CN, $Si(R^5)_3$, $N(R^5)_2$, a straight-chain alkyl or alkoxy group having 1 to 10 C atoms or a branched or cyclic alkyl or alkoxy group having 3 to 10 C atoms, where the above-mentioned groups may each be substituted by one or more radicals $R^5$ and where one or more $CH_2$ groups in the above-mentioned groups may be replaced by —C≡C—, —$R^5$C=$CR^5$—, $Si(R^5)_2$, C=O, C=$NR^5$, —$NR^5$—, —O—, —S—, —C(=O)O— or —C(=O)$NR^5$—, or an aromatic or heteroaromatic ring system having 5 to 20 aromatic ring atoms, which may in each case be substituted by one or more radicals $R^5$, where two or more radicals $R^5$ may be linked to one another and may form a ring.

More particularly, $R^4$ is selected from H or a straight-chain alkyl having 1 to 10 C atoms.

In accordance with a further preferred embodiment, $Ar^1$ and $Ar^2$, identically or differently, selected from one of the following formulae (3-1) to (8-3):

formula (3-1)
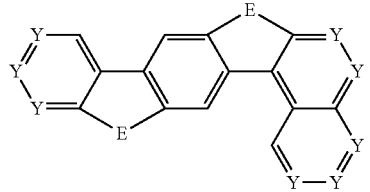
formula (3-2)
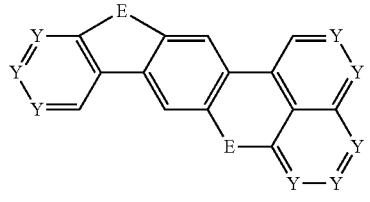
formula (3-3)
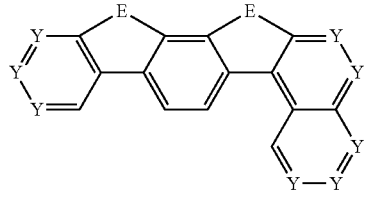
formula (3-4)
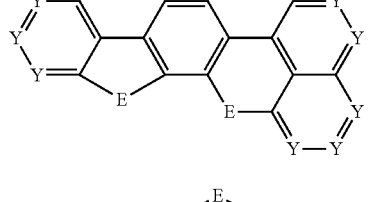
formula (4-1)
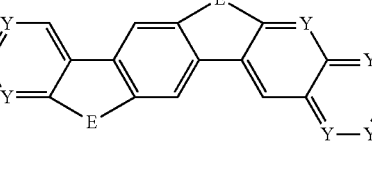
formula (4-2)
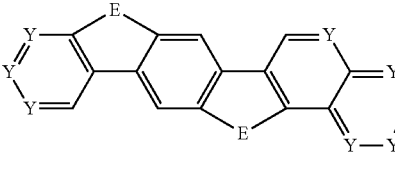
formula (4-3)
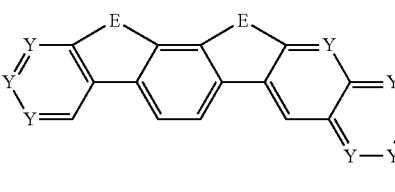
formula (4-4)
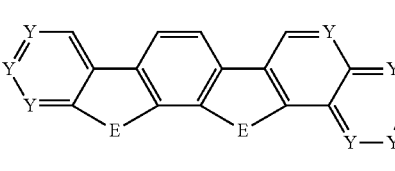
formula (5-1)
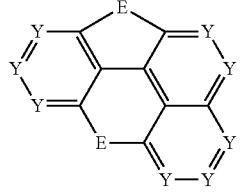
formula (5-2)
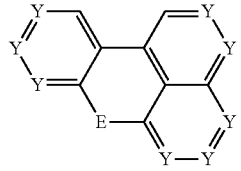
formula (5-3)
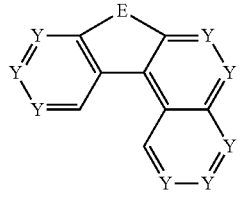
formula (6-1)
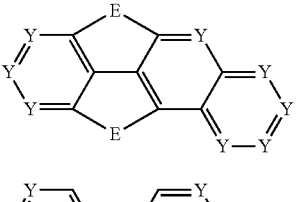
formula (6-2)
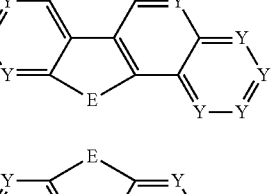
formula (6-3)
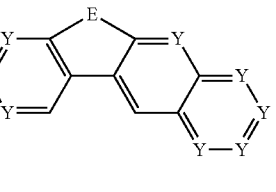
formula (7-1)
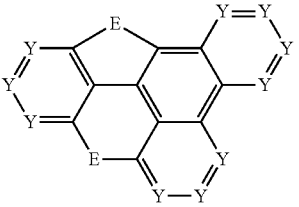
formula (7-2)
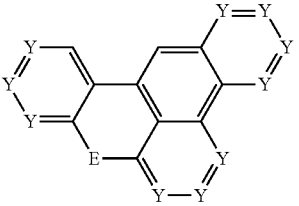

-continued formula (7-3)
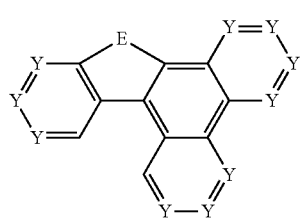

formula (8-1)
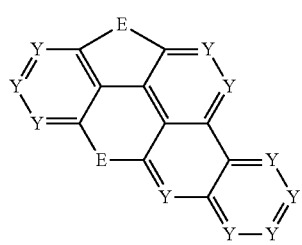

formula (8-2)
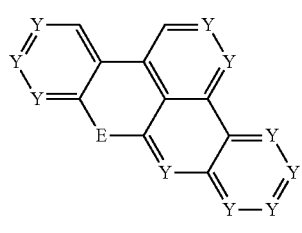

formula (8-3)
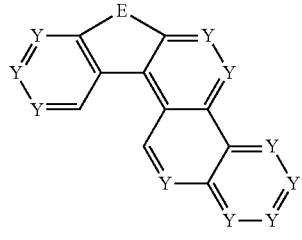

where the meaning of Y and E is the same meaning as above.

More particularly, Ar$^1$ and Ar$^2$ are preferably selected from one of the following formulae: (3-1), (3-2), (3-3), (3-4), (5-1), (5-2), or (5-3).

In a very particularly preferred embodiment, Ar$^1$ and Ar$^2$ are, identically or differently, selected from one of the following formulae (3-1-1) to (8-3-2):

formula (3-1-1)
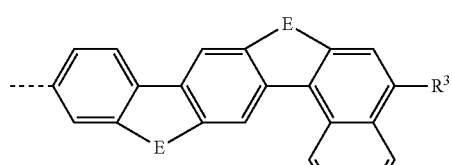

formula (3-1-2)
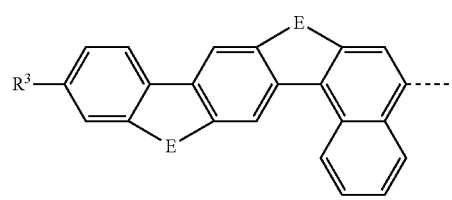

formula (3-2-1)
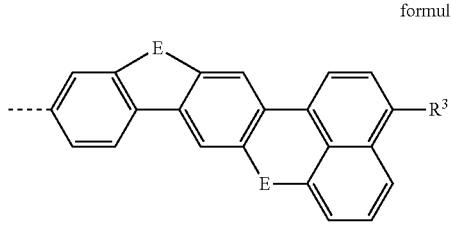

formula (3-2-2)
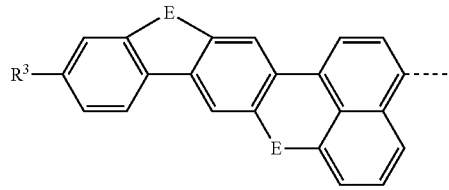

formula (3-3-1)
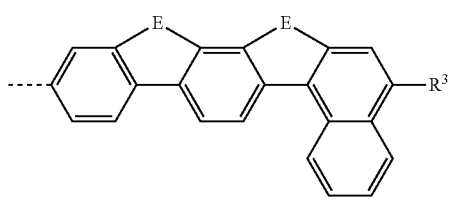

formula (3-3-2)
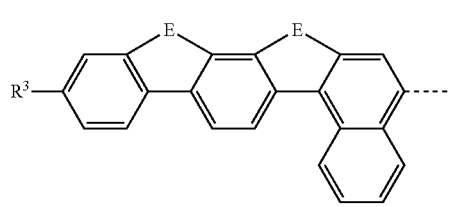

formula (3-4-1)
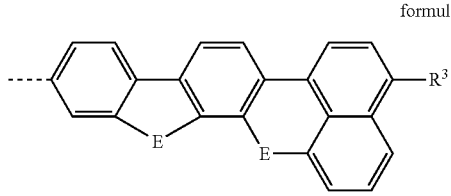

formula (3-4-2)
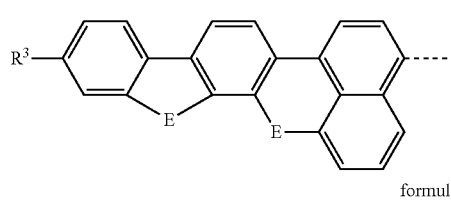

formula (4-1-1)
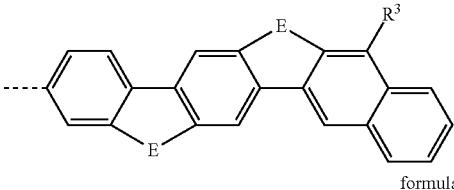

formula (4-1-2)
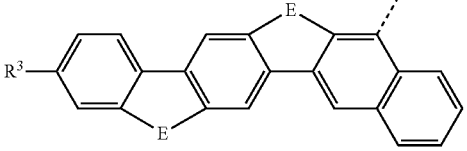

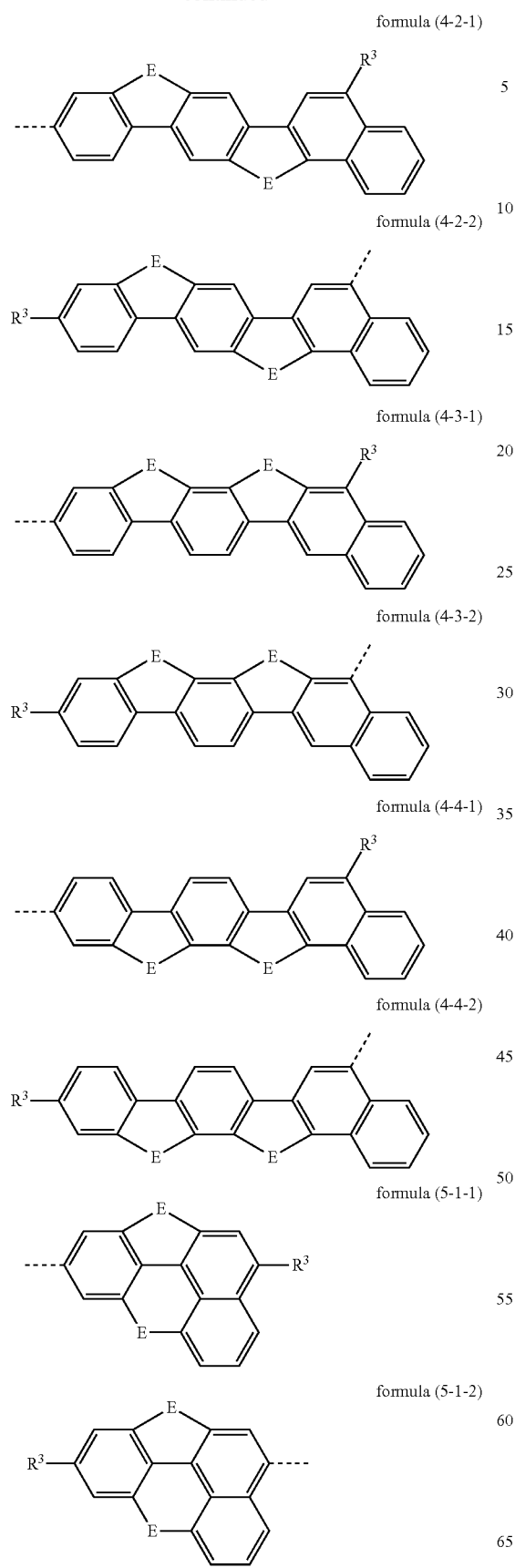
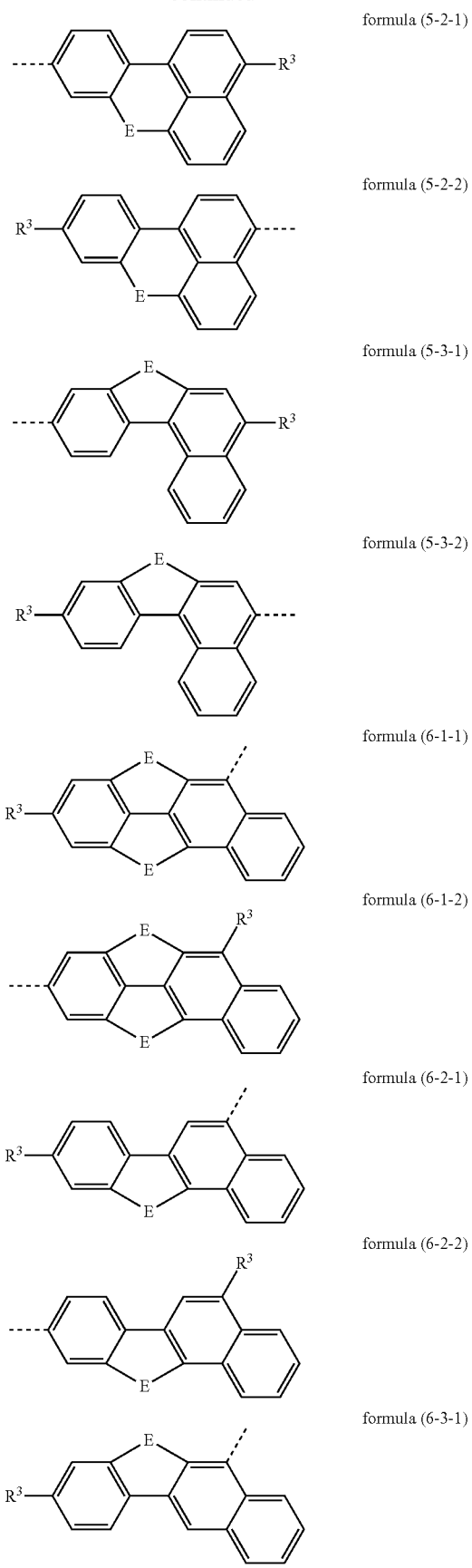

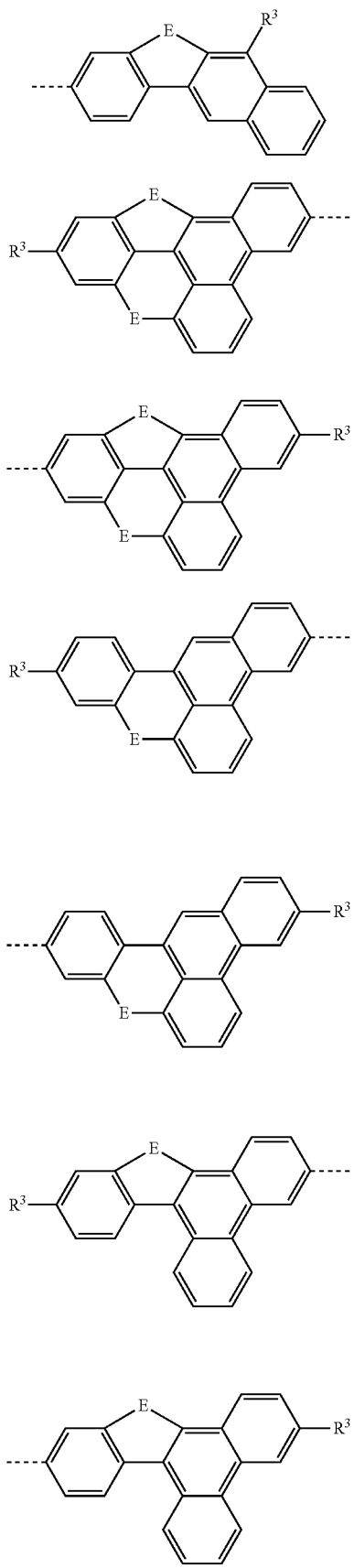

formula (6-3-2)

formula (7-1-1)

formula (7-1-2)

formula (7-2-1)

formula (7-2-2)

formula (7-3-1)

formula (7-3-2)

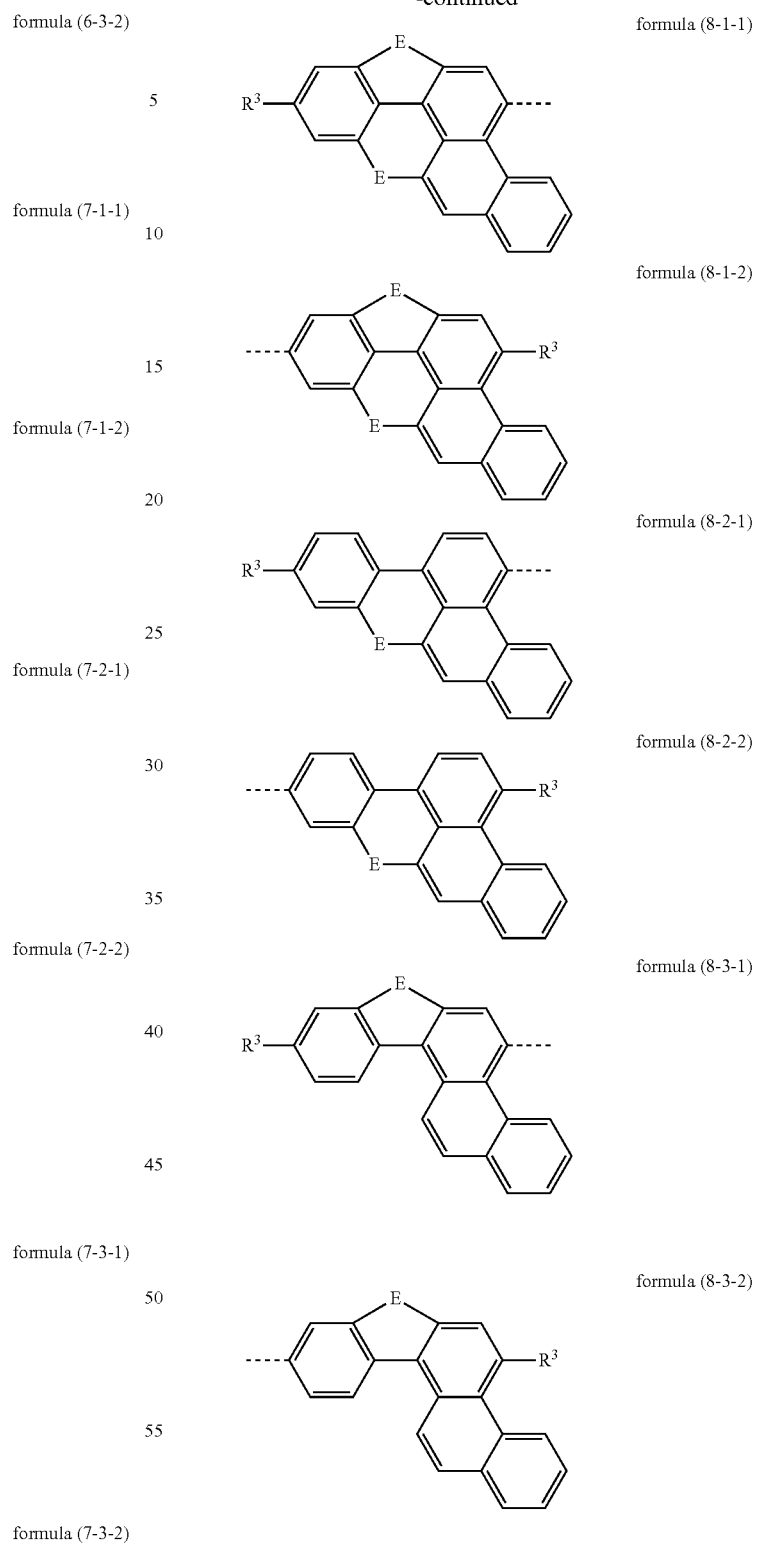

formula (8-1-1)

formula (8-1-2)

formula (8-2-1)

formula (8-2-2)

formula (8-3-1)

formula (8-3-2)

where the meaning of E and $R^3$ is the same as above and where the dashed lines represent the bonds to the 5-membered ring represented in formula (I) or (II).

Particular preference is given to compounds of the formula (I) or (II), in which the preferred embodiments mentioned above occur simultaneously. Particular preference is therefore given to compounds of formula (I) or formula (II):

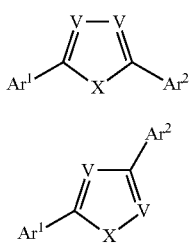

formula (I)

formula (II)

where
X is $C(R^1)_2$, $Si(R^1)_2$, O or S;
V is $CR^2$;
$Ar^1$, $Ar^2$ is, identically or differently, selected from one of the formulae (3-1) to (8-3), preferably (3-1), (3-2), (3-3), (3-4), (5-1), (5-2) or (5-3) as defined above, where E is $C(R^1)_2$ and Y is C if the 5-membered ring of formula (I) or (II) is bonded to Y and $CR^3$ otherwise;
$R^1$, $R^2$, $R^3$ is on each occurrence, identically or differently, H, D, F, CN, $Si(R^4)_3$, $N(R^4)_2$, a straight-chain alkyl or alkoxy group having 1 to 10 C atoms or a branched or cyclic alkyl or alkoxy group having 3 to 10 C atoms, where the above-mentioned groups may each be substituted by one or more radicals $R^4$ and where one or more $CH_2$ groups in the above-mentioned groups may be replaced by —C≡C—, —$R^4$C=C$R^4$—, $Si(R^4)_2$, C=O, C=$NR^4$, —$NR^4$—, —O—, —S—, —C(=O)O— or —C(=O)$NR^4$—, or an aromatic or heteroaromatic ring system having 5 to 20 aromatic ring atoms, which may in each case be substituted by one or more radicals $R^4$, where two radicals $R^1$ may be linked to one another and may form a ring, two radicals $R^2$ may be linked to one another and may form a ring or two radicals $R^3$ may be linked to one another and may form a ring;
$R^4$ is on each occurrence, identically or differently, H, D, F, CN, $Si(R^5)_3$, $N(R^5)_2$, a straight-chain alkyl or alkoxy group having 1 to 10 C atoms or a branched or cyclic alkyl or alkoxy group having 3 to 10 C atoms, where the above-mentioned groups may each be substituted by one or more radicals $R^5$ and where one or more $CH_2$ groups in the above-mentioned groups may be replaced by —C≡C—, —$R^5$C=C$R^5$—, $Si(R^5)_2$, C=O, C=$NR^5$, —$NR^5$—, —O—, —S—, —C(=O)O— or —C(=O)$NR^5$—, or an aromatic or heteroaromatic ring system having 5 to 20 aromatic ring atoms, which may in each case be substituted by one or more radicals $R^5$, where two or more radicals $R^4$ may be linked to one another and may form a ring;
$R^5$ has the same meaning as above;
a+b=1;
c+d=1;
e+f=1 or 2.

The following table shows examples of compounds of the formulae (I) or (II):

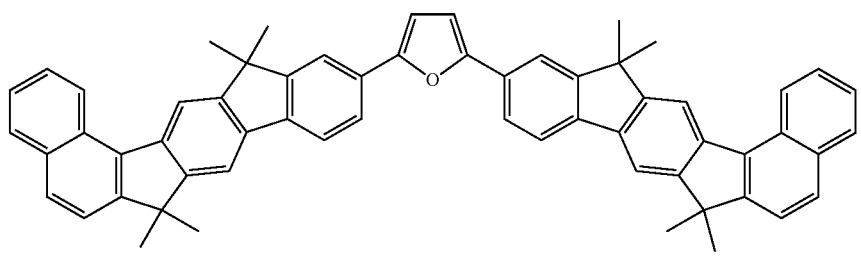 [SMILES: CC1(C)c2cc(-c3ccc(-c4ccc5c(c4)C(C)(C)c4cc6c(cc4-5)C(C)(C)c4ccc5ccccc5c4-6)o3)ccc2-c2cc3c(cc21)-c1c(ccc2ccccc12)C3(C)C]

1

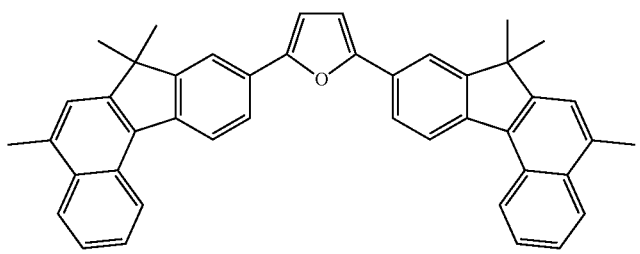

2

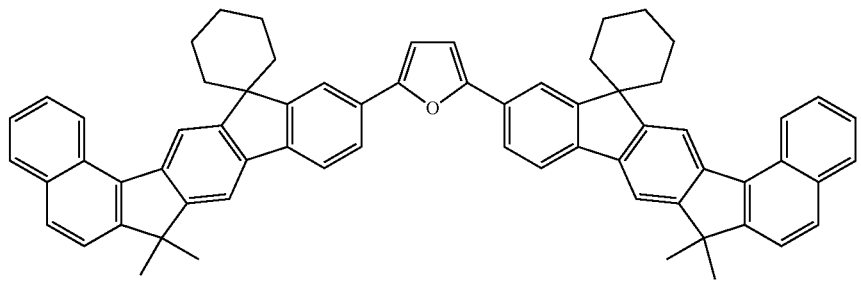 [SMILES: CC1(C)c2cc3c(cc2-c2c1ccc1ccccc21)C1(CCCCC1)c1cc(-c2ccc(-c4ccc5c(c4)C4(CCCCC4)c4cc6c(cc4-5)C(C)(C)c4ccc5ccccc5c4-6)o2)ccc1-3]

3

-continued
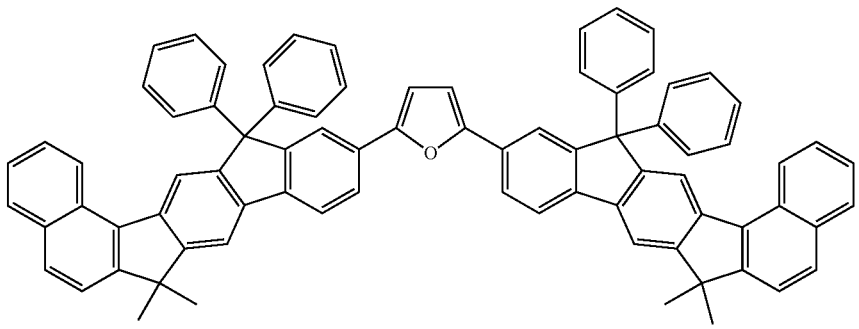 [SMILES: CC1(C)c2cc3c(cc2-c2c1ccc1ccccc21)C(c1ccccc1)(c1ccccc1)c1cc(-c2ccc(-c4ccc5c(c4)C(c4ccccc4)(c4ccccc4)c4cc6c(cc4-5)C(C)(C)c4ccc5ccccc5c4-6)o2)ccc1-3]
4
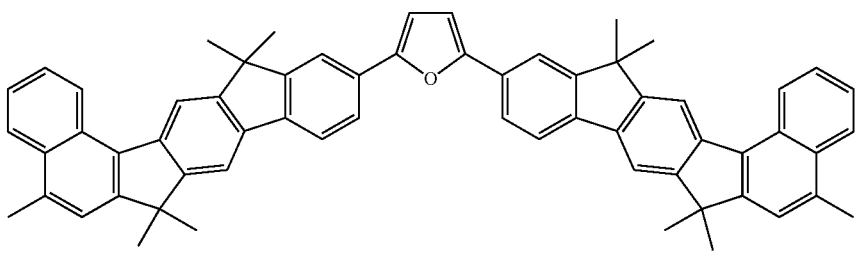 [SMILES: Cc1cc2c(c3ccccc13)-c1cc3c(cc1C2(C)C)-c1ccc(-c2ccc(-c4ccc5c(c4)C(C)(C)c4cc6c(cc4-5)C(C)(C)c4cc(C)c5ccccc5c4-6)o2)cc1C3(C)C]
5
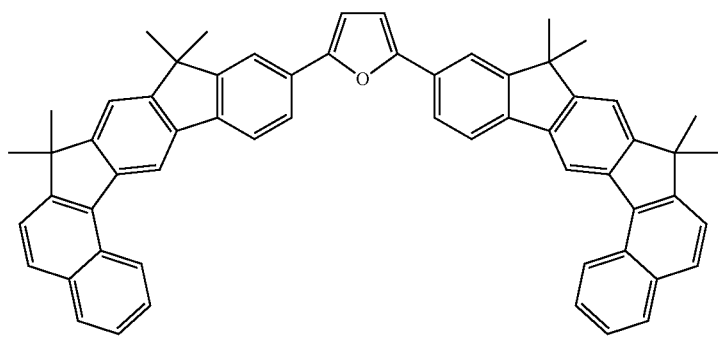
6
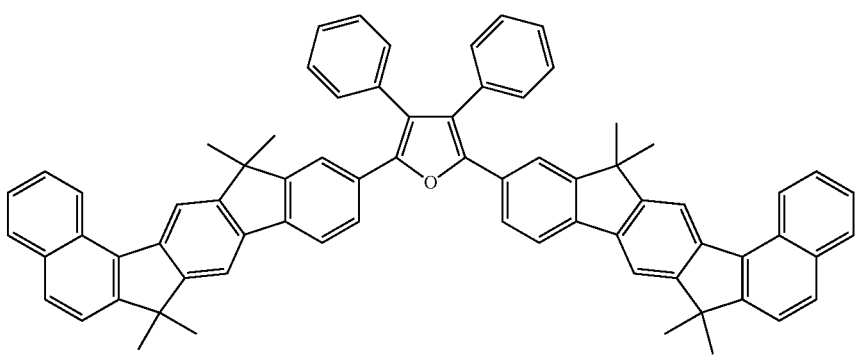 [SMILES: CC1(C)c2cc(-c3oc(-c4ccc5c(c4)C(C)(C)c4cc6c(cc4-5)C(C)(C)c4ccc5ccccc5c4-6)c(-c4ccccc4)c3-c3ccccc3)ccc2-c2cc3c(cc21)-c1c(ccc2ccccc12)C3(C)C]
7
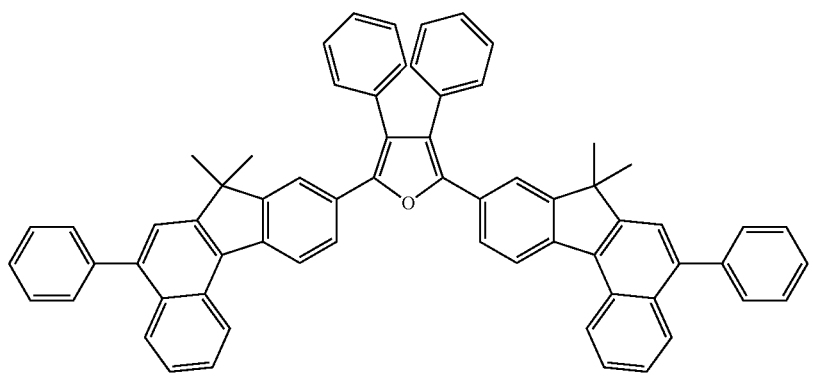 [SMILES: CC1(C)c2cc(-c3oc(-c4ccc5c(c4)C(C)(C)c4cc(-c6ccccc6)c6ccccc6c4-5)c(-c4ccccc4)c3-c3ccccc3)ccc2-c2c1cc(-c1ccccc1)c1ccccc21]
8

-continued
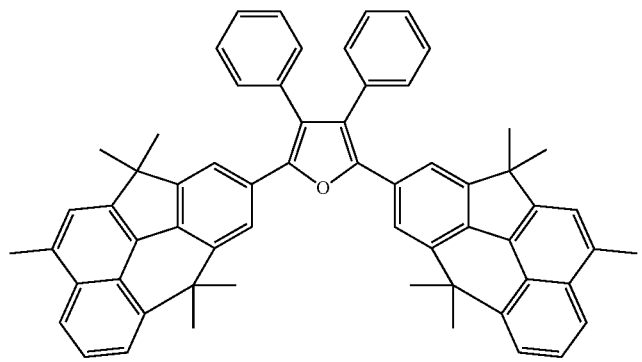
9
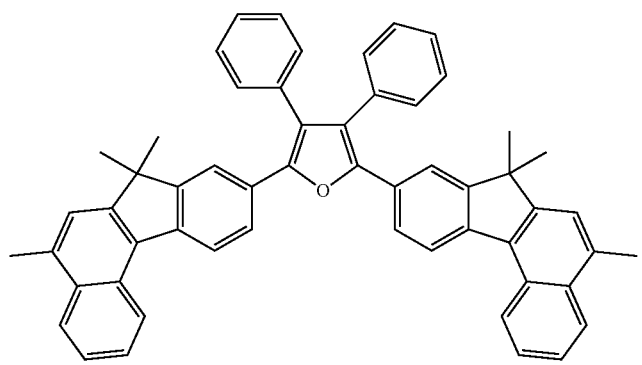
10
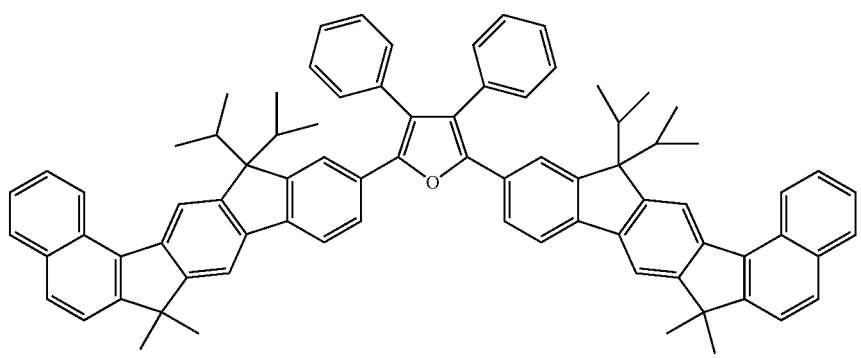 [SMILES: CC(C)C1(C(C)C)c2cc(-c3oc(-c4ccc5c(c4)C(C(C)C)(C(C)C)c4cc6c(cc4-5)C(C)(C)c4ccc5ccccc5c4-6)c(-c4ccccc4)c3-c3ccccc3)ccc2-c2cc3c(cc21)-c1c(ccc2ccccc12)C3(C)C]
11
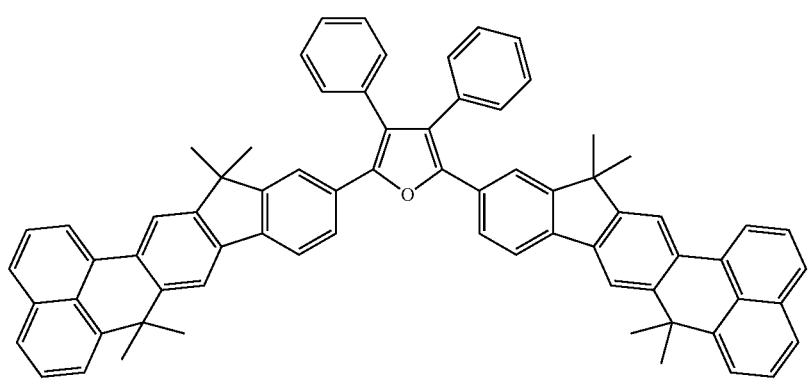 [SMILES: CC1(C)c2cc(-c3oc(-c4ccc5c(c4)C(C)(C)c4cc6c(cc4-5)C(C)(C)c4cccc5cccc-6c45)c(-c4ccccc4)c3-c3ccccc3)ccc2-c2cc3c(cc21)-c1cccc2cccc(c12)C3(C)C]
12

13
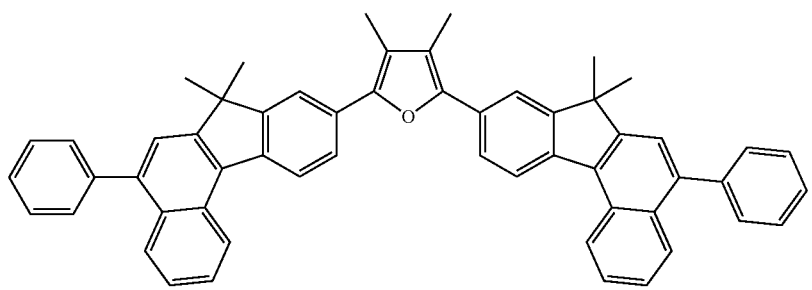 [SMILES: Cc1c(-c2ccc3c(c2)C(C)(C)c2cc(-c4ccccc4)c4ccccc4c2-3)oc(-c2ccc3c(c2)C(C)(C)c2cc(-c4ccccc4)c4ccccc4c2-3)c1C]
14
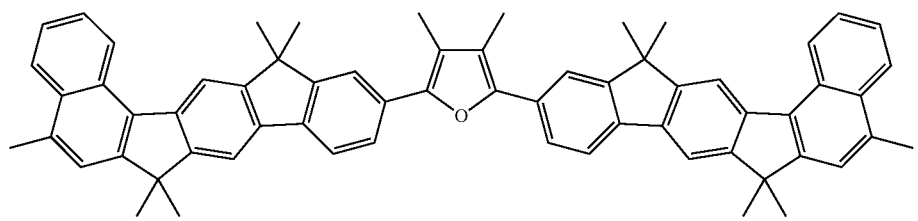
15
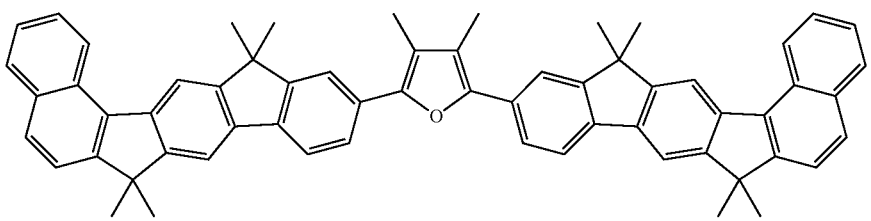 [SMILES: Cc1c(-c2ccc3c(c2)C(C)(C)c2cc4c(cc2-3)C(C)(C)c2ccc3ccccc3c2-4)oc(-c2ccc3c(c2)C(C)(C)c2cc4c(cc2-3)C(C)(C)c2ccc3ccccc3c2-4)c1C]
16
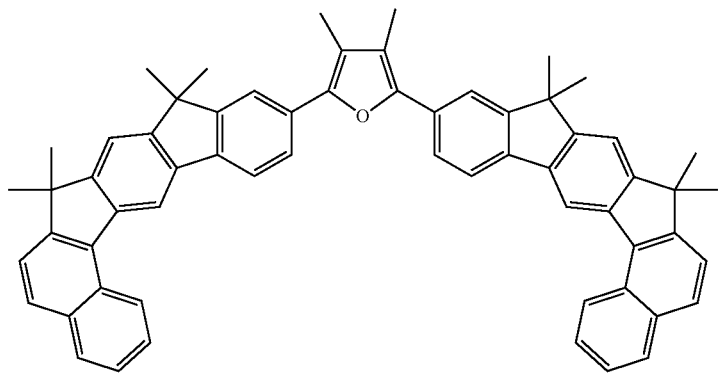
17
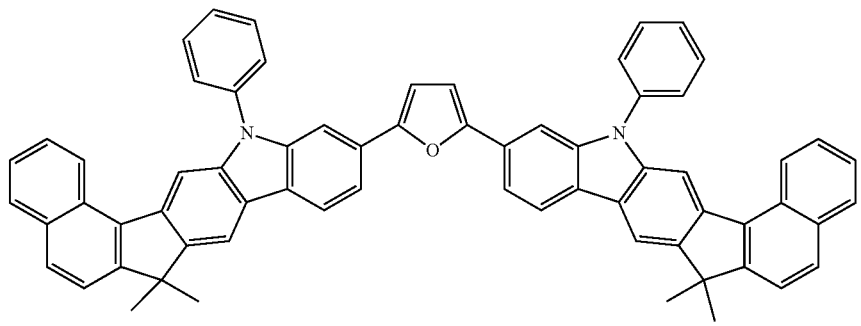 [SMILES: CC1(C)c2cc3c4ccc(-c5ccc(-c6ccc7c8cc9c(cc8n(-c8ccccc8)c7c6)-c6c(ccc7ccccc67)C9(C)C)o5)cc4n(-c4ccccc4)c3cc2-c2c1ccc1ccccc21]

-continued
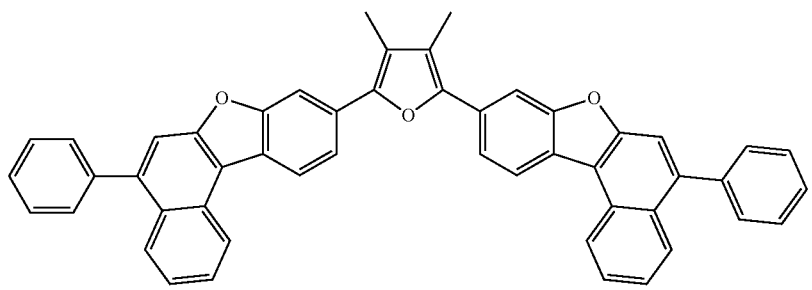 [SMILES: Cc1c(-c2ccc3c(c2)oc2cc(-c4ccccc4)c4ccccc4c23)oc(-c2ccc3c(c2)oc2cc(-c4ccccc4)c4ccccc4c23)c1C]
18
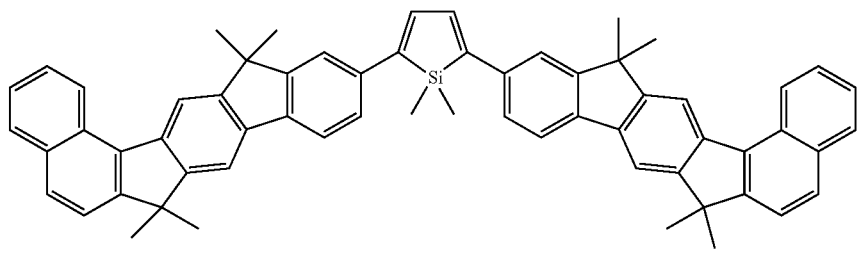 [SMILES: CC1(C)c2cc(C3=CC=C(c4ccc5c(c4)C(C)(C)c4cc6c(cc4-5)C(C)(C)c4ccc5ccccc5c4-6)[Si]3(C)C)ccc2-c2cc3c(cc21)-c1c(ccc2ccccc12)C3(C)C]
19
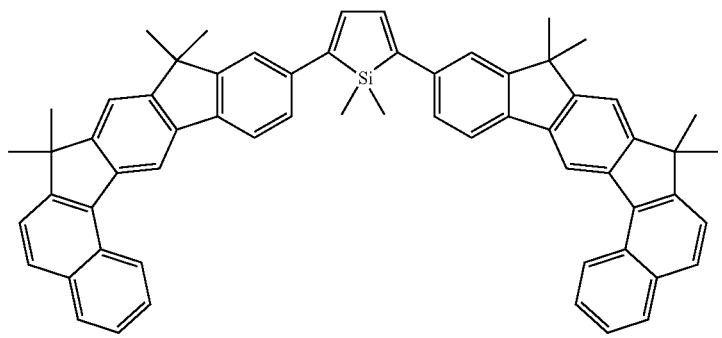
20
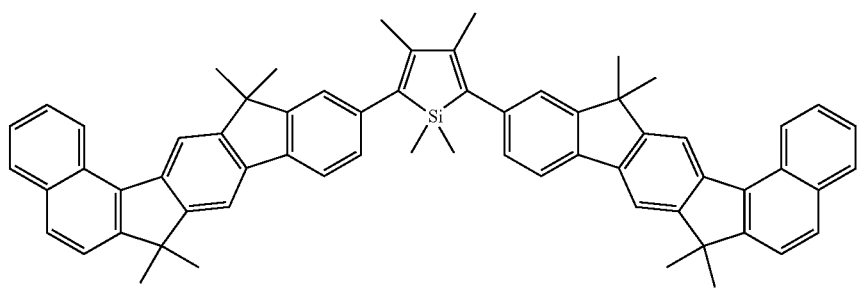 [SMILES: CC1=C(c2ccc3c(c2)C(C)(C)c2cc4c(cc2-3)C(C)(C)c2ccc3ccccc3c2-4)[Si](C)(C)C(c2ccc3c(c2)C(C)(C)c2cc4c(cc2-3)C(C)(C)c2ccc3ccccc3c2-4)=C1C]
21
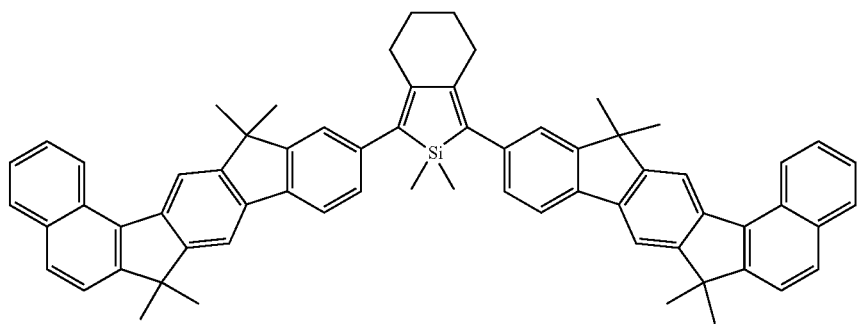 [SMILES: CC1(C)c2cc(C3=C4CCCCC4=C(c4ccc5c(c4)C(C)(C)c4cc6c(cc4-5)C(C)(C)c4ccc5ccccc5c4-6)[Si]3(C)C)ccc2-c2cc3c(cc21)-c1c(ccc2ccccc12)C3(C)C]
22

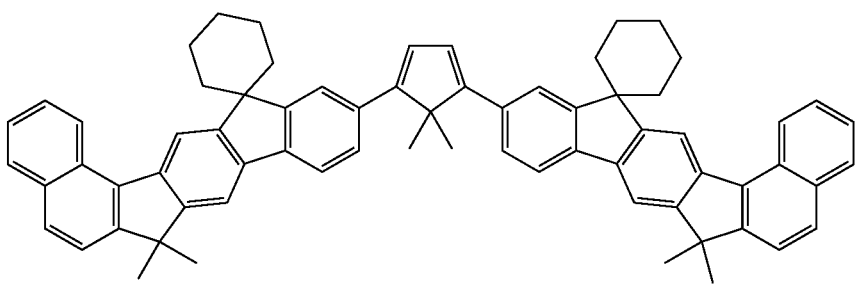 [SMILES: CC1(C)C(c2ccc3c(c2)C2(CCCCC2)c2cc4c(cc2-3)C(C)(C)c2ccc3ccccc3c2-4)=CC=C1c1ccc2c(c1)C1(CCCCC1)c1cc3c(cc1-2)C(C)(C)c1ccc2ccccc2c1-3]
23
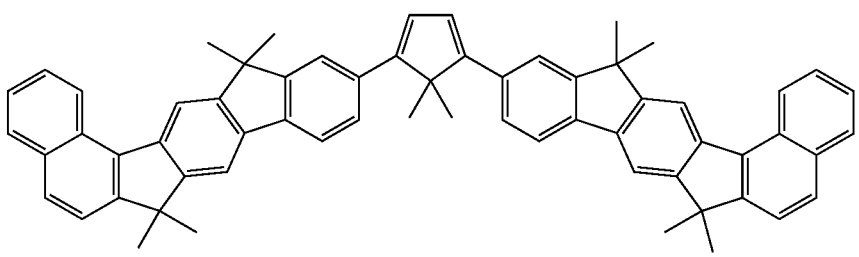 [SMILES: CC1(C)C(c2ccc3c(c2)C(C)(C)c2cc4c(cc2-3)C(C)(C)c2ccc3ccccc3c2-4)=CC=C1c1ccc2c(c1)C(C)(C)c1cc3c(cc1-2)C(C)(C)c1ccc2ccccc2c1-3]
24
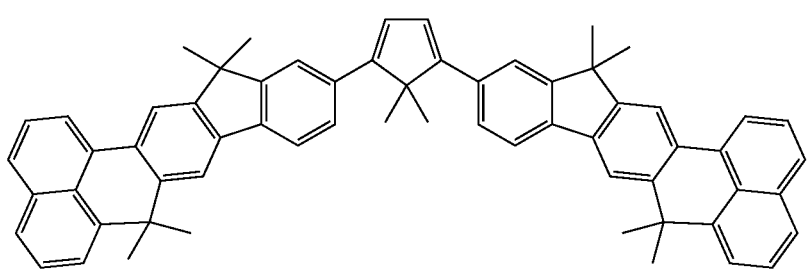 [SMILES: CC1(C)C(c2ccc3c(c2)C(C)(C)c2cc4c(cc2-3)C(C)(C)c2cccc3cccc-4c23)=CC=C1c1ccc2c(c1)C(C)(C)c1cc3c(cc1-2)C(C)(C)c1cccc2cccc-3c12]
25
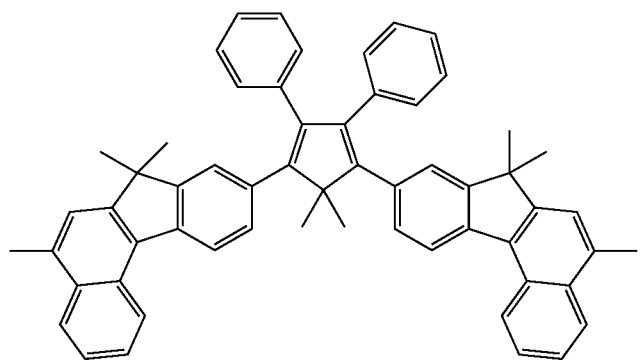
26
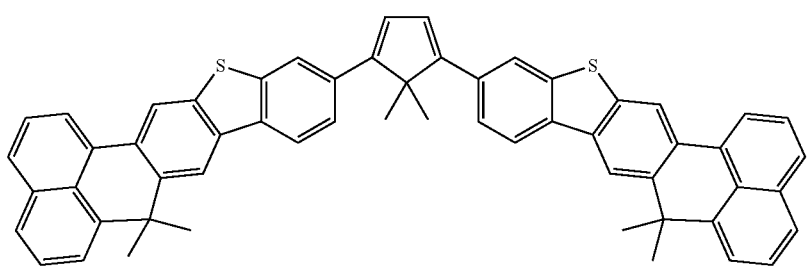 [SMILES: CC1(C)C(c2ccc3c(c2)sc2cc4c(cc23)C(C)(C)c2cccc3cccc-4c23)=CC=C1c1ccc2c(c1)sc1cc3c(cc12)C(C)(C)c1cccc2cccc-3c12]
27

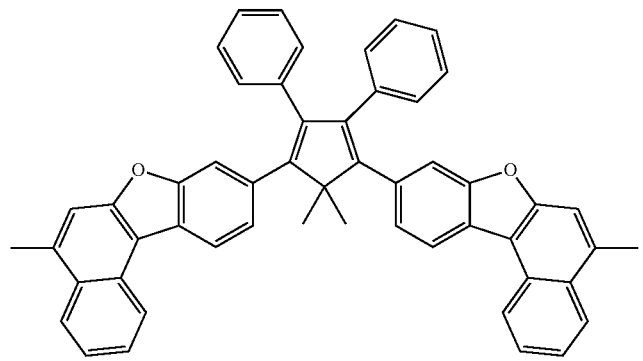
28
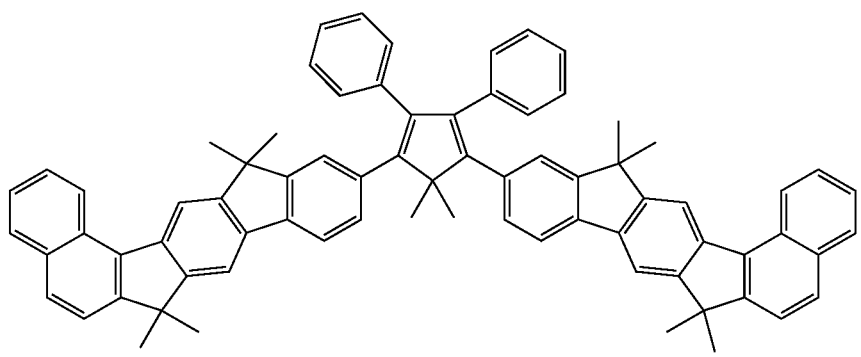 [SMILES: CC1(C)C(c2ccc3c(c2)C(C)(C)c2cc4c(cc2-3)C(C)(C)c2ccc3ccccc3c2-4)=C(c2ccccc2)C(c2ccccc2)=C1c1ccc2c(c1)C(C)(C)c1cc3c(cc1-2)C(C)(C)c1ccc2ccccc2c1-3]
29
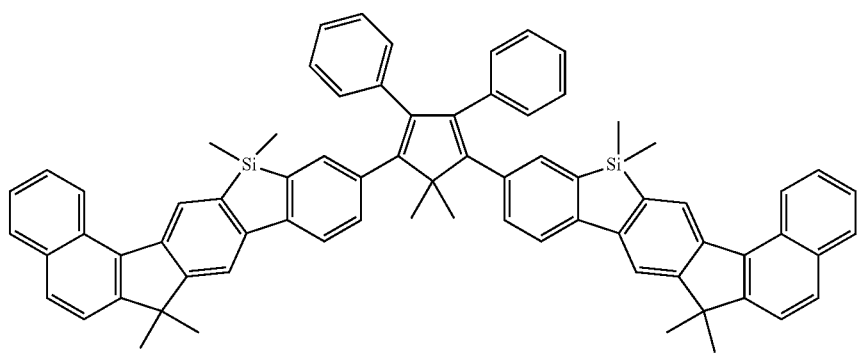 [SMILES: CC1(C)C(c2ccc3c(c2)[Si](C)(C)c2cc4c(cc2-3)C(C)(C)c2ccc3ccccc3c2-4)=C(c2ccccc2)C(c2ccccc2)=C1c1ccc2c(c1)[Si](C)(C)c1cc3c(cc1-2)C(C)(C)c1ccc2ccccc2c1-3]
30
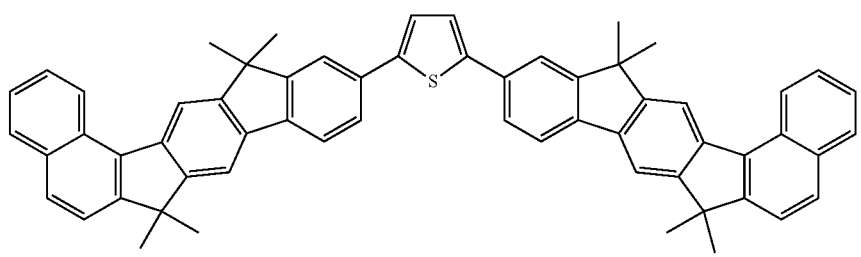 [SMILES: CC1(C)c2cc(-c3ccc(-c4ccc5c(c4)C(C)(C)c4cc6c(cc4-5)C(C)(C)c4ccc5ccccc5c4-6)s3)ccc2-c2cc3c(cc21)-c1c(ccc2ccccc12)C3(C)C]
31
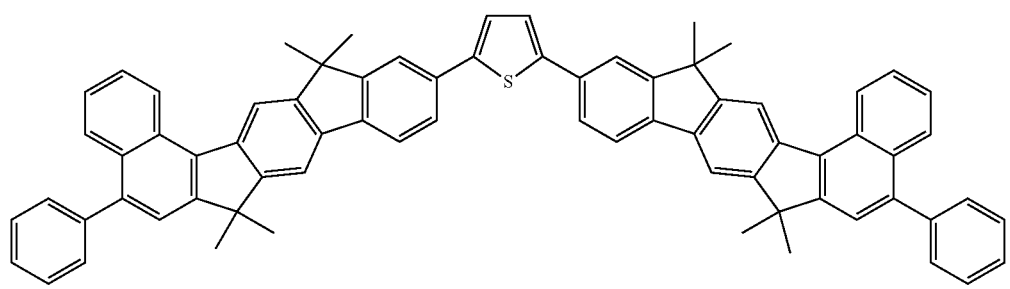 [SMILES: CC1(C)c2cc(-c3ccc(-c4ccc5c(c4)C(C)(C)c4cc6c(cc4-5)C(C)(C)c4cc(-c5ccccc5)c5ccccc5c4-6)s3)ccc2-c2cc3c(cc21)-c1c(cc(-c2ccccc2)c2ccccc12)C3(C)C]
32

-continued
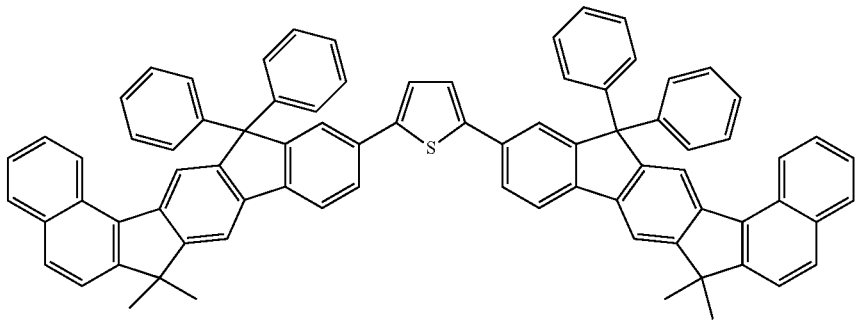 [SMILES: CC1(C)c2cc3c(cc2-c2c1ccc1ccccc21)C(c1ccccc1)(c1ccccc1)c1cc(-c2ccc(-c4ccc5c(c4)C(c4ccccc4)(c4ccccc4)c4cc6c(cc4-5)C(C)(C)c4ccc5ccccc5c4-6)s2)ccc1-3]
33
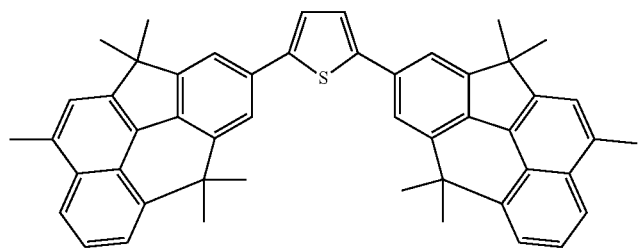
34
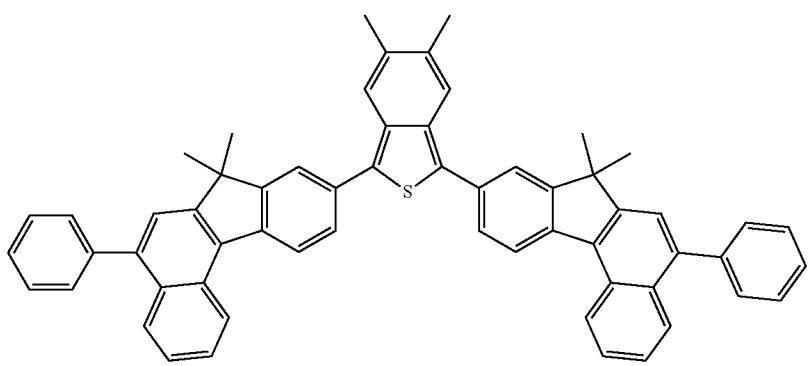 [SMILES: Cc1cc2c(-c3ccc4c(c3)C(C)(C)c3cc(-c5ccccc5)c5ccccc5c3-4)sc(-c3ccc4c(c3)C(C)(C)c3cc(-c5ccccc5)c5ccccc5c3-4)c2cc1C]
35
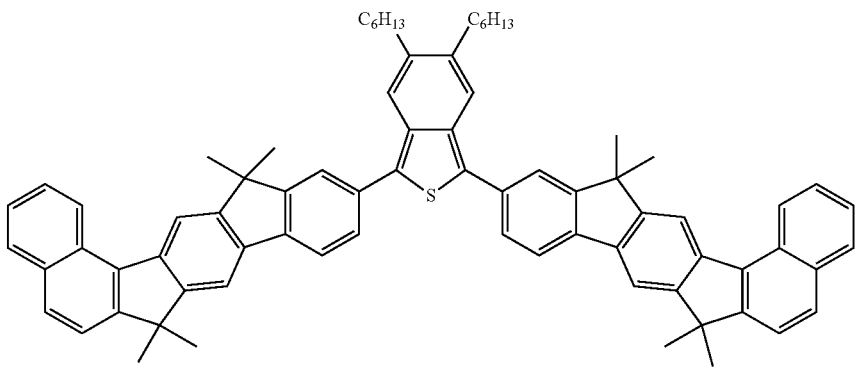
36
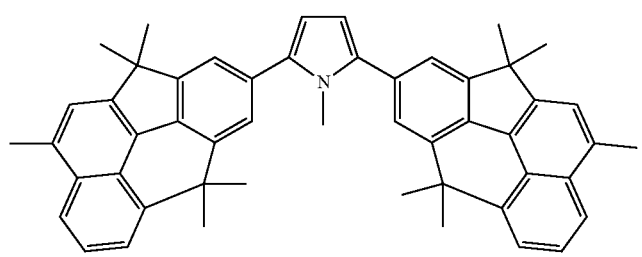
37

-continued
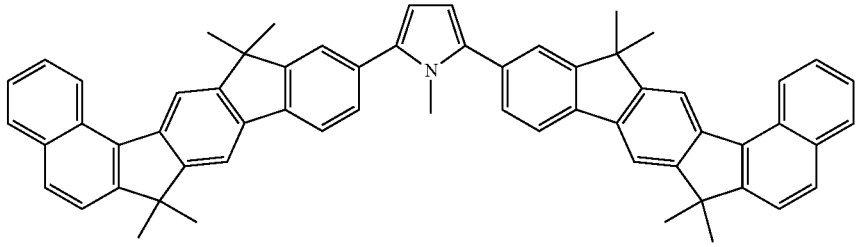 [SMILES: Cn1c(-c2ccc3c(c2)C(C)(C)c2cc4c(cc2-3)C(C)(C)c2ccc3ccccc3c2-4)ccc1-c1ccc2c(c1)C(C)(C)c1cc3c(cc1-2)C(C)(C)c1ccc2ccccc2c1-3]
38
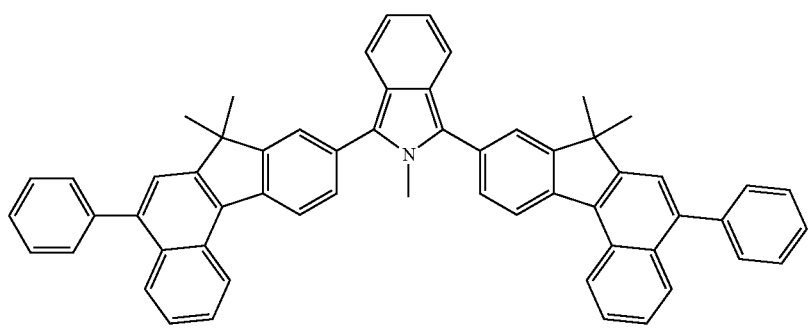 [SMILES: Cn1c(-c2ccc3c(c2)C(C)(C)c2cc(-c4ccccc4)c4ccccc4c2-3)c2ccccc2c1-c1ccc2c(c1)C(C)(C)c1cc(-c3ccccc3)c3ccccc3c1-2]
39
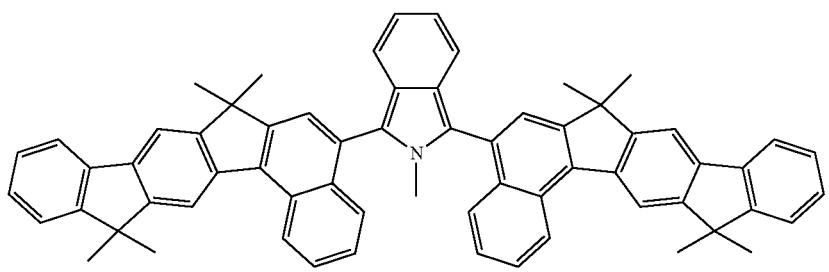 [SMILES: Cn1c(-c2cc3c(c4ccccc24)-c2cc4c(cc2C3(C)C)-c2ccccc2C4(C)C)c2ccccc2c1-c1cc2c(c3ccccc13)-c1cc3c(cc1C2(C)C)-c1ccccc1C3(C)C]
40
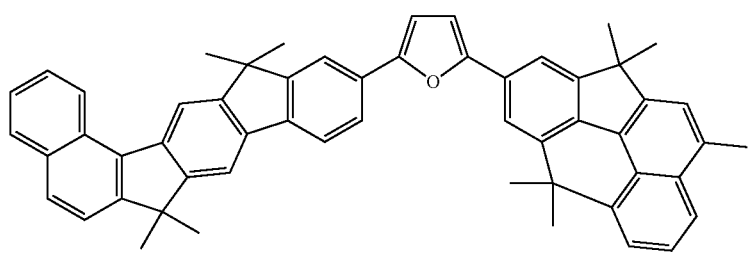 [SMILES: Cc1cc2c3c4c(cccc14)C(C)(C)c1cc(-c4ccc(-c5ccc6c(c5)C(C)(C)c5cc7c(cc5-6)C(C)(C)c5ccc6ccccc6c5-7)o4)cc(c1-3)C2(C)C]
41
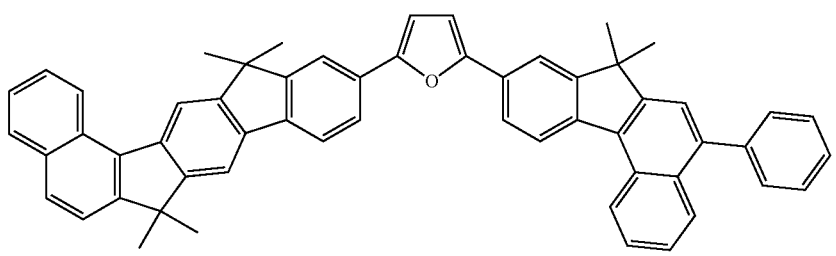 [SMILES: CC1(C)c2cc(-c3ccc(-c4ccc5c(c4)C(C)(C)c4cc(-c6ccccc6)c6ccccc6c4-5)o3)ccc2-c2cc3c(cc21)-c1c(ccc2ccccc12)C3(C)C]
42
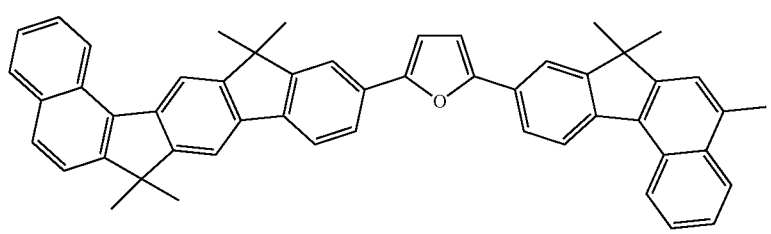 [SMILES: Cc1cc2c(c3ccccc13)-c1ccc(-c3ccc(-c4ccc5c(c4)C(C)(C)c4cc6c(cc4-5)C(C)(C)c4ccc5ccccc5c4-6)o3)cc1C2(C)C]
43

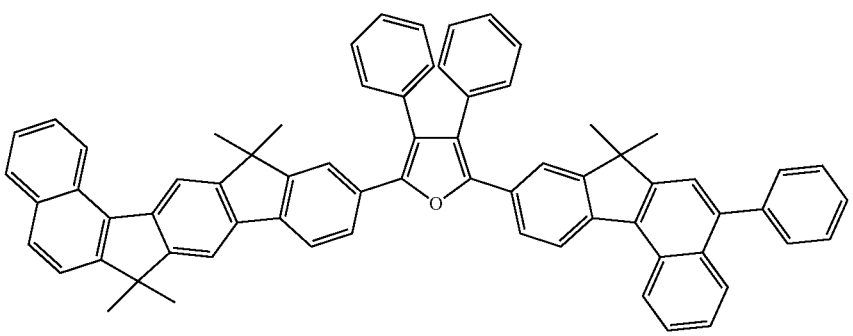 [SMILES: CC1(C)c2cc(-c3oc(-c4ccc5c(c4)C(C)(C)c4cc(-c6ccccc6)c6ccccc6c4-5)c(-c4ccccc4)c3-c3ccccc3)ccc2-c2cc3c(cc21)-c1c(ccc2ccccc12)C3(C)C]

-continued
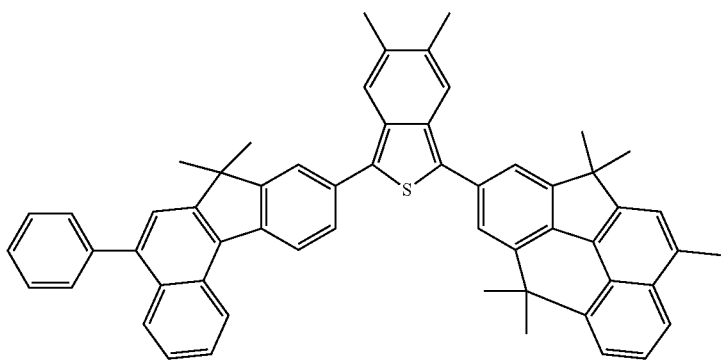 [SMILES: Cc1cc2c(-c3ccc4c(c3)C(C)(C)c3cc(-c5ccccc5)c5ccccc5c3-4)sc(-c3cc4c5c(c3)C(C)(C)c3cccc6c(C)cc(c-5c36)C4(C)C)c2cc1C]
49
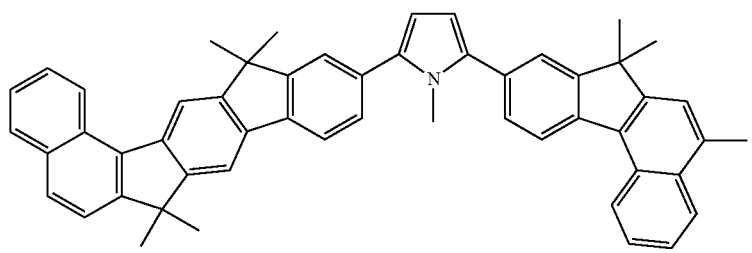 [SMILES: Cc1cc2c(c3ccccc13)-c1ccc(-c3ccc(-c4ccc5c(c4)C(C)(C)c4cc6c(cc4-5)C(C)(C)c4ccc5ccccc5c4-6)n3C)cc1C2(C)C]
50
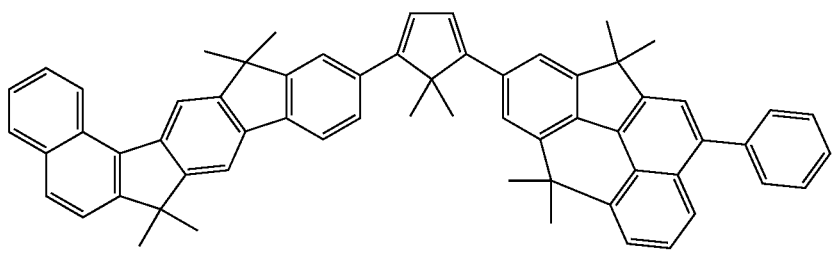 [SMILES: CC1(C)C(c2ccc3c(c2)C(C)(C)c2cc4c(cc2-3)C(C)(C)c2ccc3ccccc3c2-4)=CC=C1c1cc2c3c(c1)C(C)(C)c1cccc4c(-c5ccccc5)cc(c-3c14)C2(C)C]
51
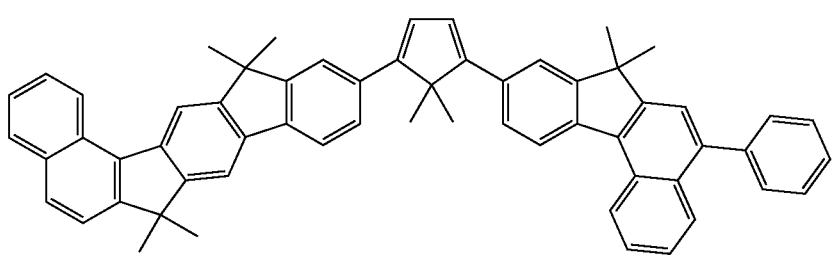 [SMILES: CC1(C)C(c2ccc3c(c2)C(C)(C)c2cc4c(cc2-3)C(C)(C)c2ccc3ccccc3c2-4)=CC=C1c1ccc2c(c1)C(C)(C)c1cc(-c3ccccc3)c3ccccc3c1-2]
52
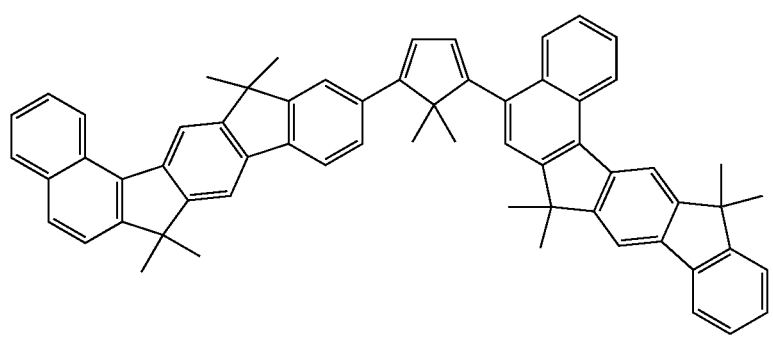 [SMILES: CC1(C)C(c2ccc3c(c2)C(C)(C)c2cc4c(cc2-3)C(C)(C)c2ccc3ccccc3c2-4)=CC=C1c1cc2c(c3ccccc13)-c1cc3c(cc1C2(C)C)-c1ccccc1C3(C)C]
53

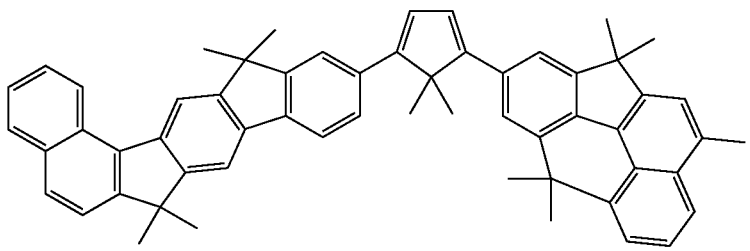 [SMILES: Cc1cc2c3c4c(cccc14)C(C)(C)c1cc(C4=CC=C(c5ccc6c(c5)C(C)(C)c5cc7c(cc5-6)C(C)(C)c5ccc6ccccc6c5-7)C4(C)C)cc(c1-3)C2(C)C]
54
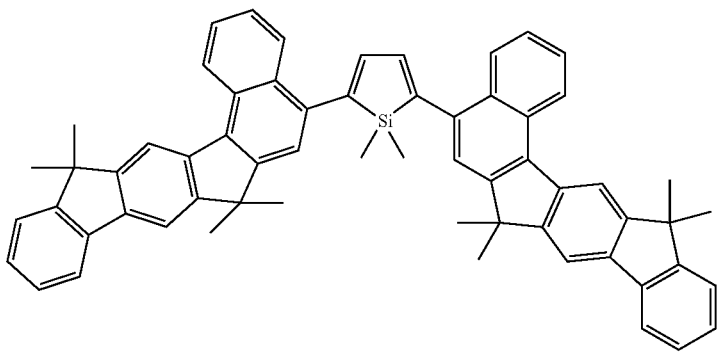 [SMILES: CC1(C)c2ccccc2-c2cc3c(cc21)-c1c(cc(C2=CC=C(c4cc5c(c6ccccc46)-c4cc6c(cc4C5(C)C)-c4ccccc4C6(C)C)[Si]2(C)C)c2ccccc12)C3(C)C]
55
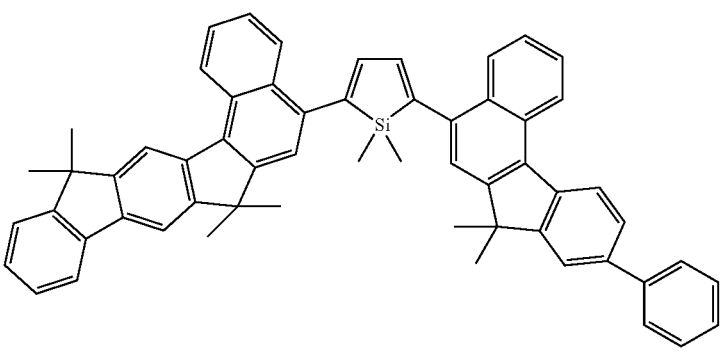 [SMILES: CC1(C)c2ccccc2-c2cc3c(cc21)-c1c(cc(C2=CC=C(c4cc5c(c6ccccc46)-c4ccc(-c6ccccc6)cc4C5(C)C)[Si]2(C)C)c2ccccc12)C3(C)C]
56
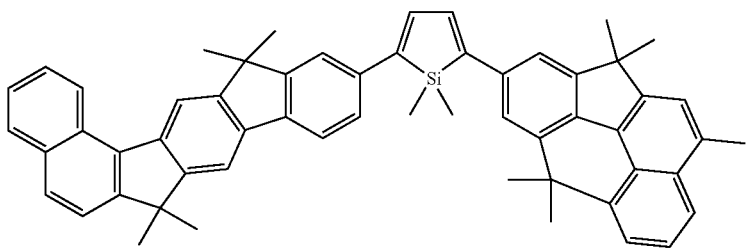
57
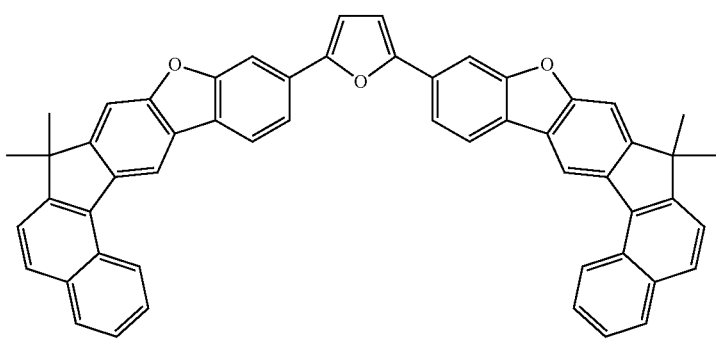
58

-continued
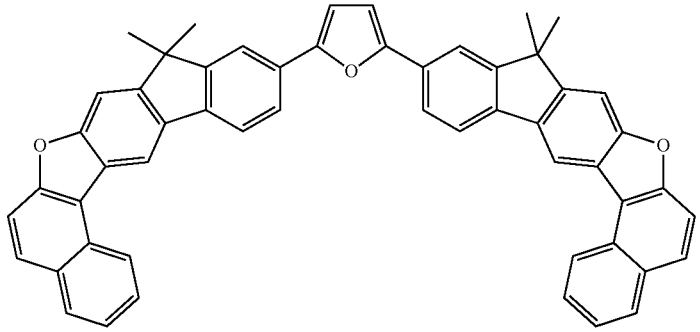 [SMILES: CC1(C)c2cc(-c3ccc(-c4ccc5c(c4)C(C)(C)c4cc6oc7ccc8ccccc8c7c6cc4-5)o3)ccc2-c2cc3c(cc21)oc1ccc2ccccc2c13]
59
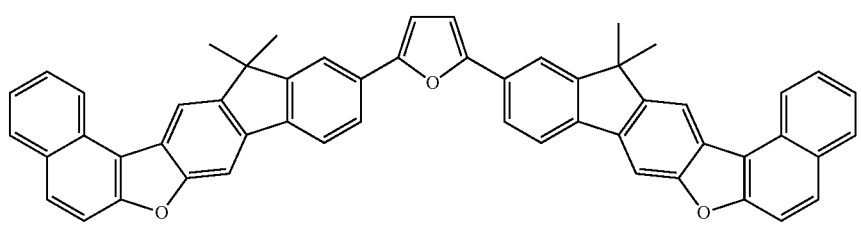 [SMILES: CC1(C)c2cc(-c3ccc(-c4ccc5c(c4)C(C)(C)c4cc6c(cc4-5)oc4ccc5ccccc5c46)o3)ccc2-c2cc3oc4ccc5ccccc5c4c3cc21]
60
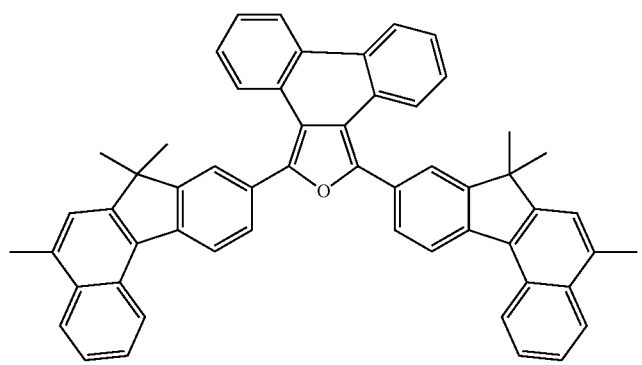
61
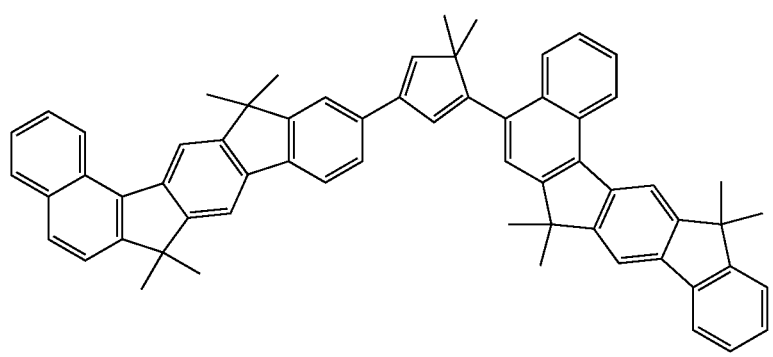 [SMILES: CC1(C)C=C(c2ccc3c(c2)C(C)(C)c2cc4c(cc2-3)C(C)(C)c2ccc3ccccc3c2-4)C=C1c1cc2c(c3ccccc13)-c1cc3c(cc1C2(C)C)-c1ccccc1C3(C)C]
62
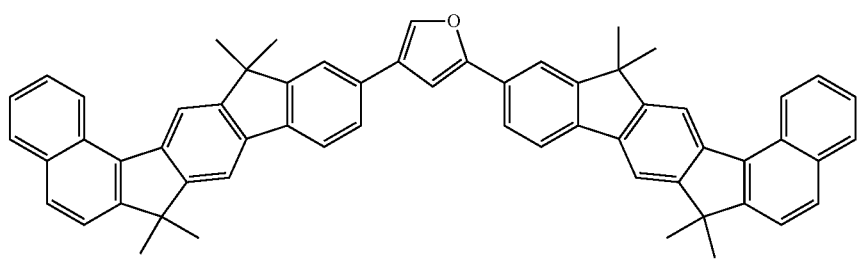 [SMILES: CC1(C)c2cc(-c3coc(-c4ccc5c(c4)C(C)(C)c4cc6c(cc4-5)C(C)(C)c4ccc5ccccc5c4-6)c3)ccc2-c2cc3c(cc21)-c1c(ccc2ccccc12)C3(C)C]
63

-continued
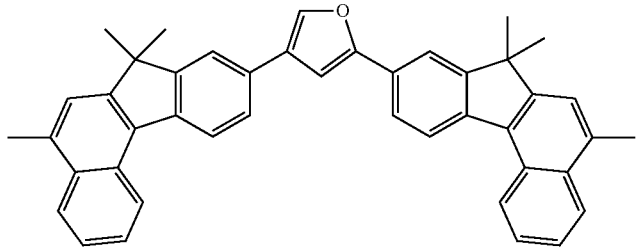
64
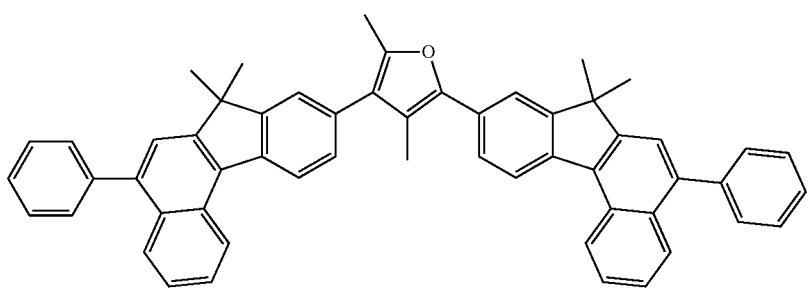 [SMILES: Cc1oc(-c2ccc3c(c2)C(C)(C)c2cc(-c4ccccc4)c4ccccc4c2-3)c(C)c1-c1ccc2c(c1)C(C)(C)c1cc(-c3ccccc3)c3ccccc3c1-2]
65
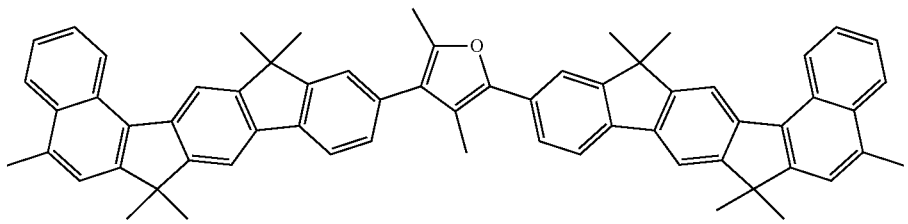
66
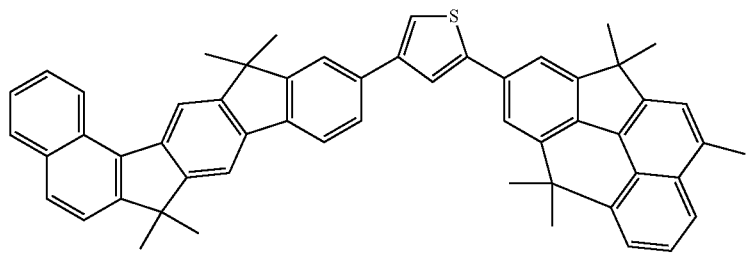 [SMILES: Cc1cc2c3c4c(cccc14)C(C)(C)c1cc(-c4cc(-c5ccc6c(c5)C(C)(C)c5cc7c(cc5-6)C(C)(C)c5ccc6ccccc6c5-7)cs4)cc(c1-3)C2(C)C]
67
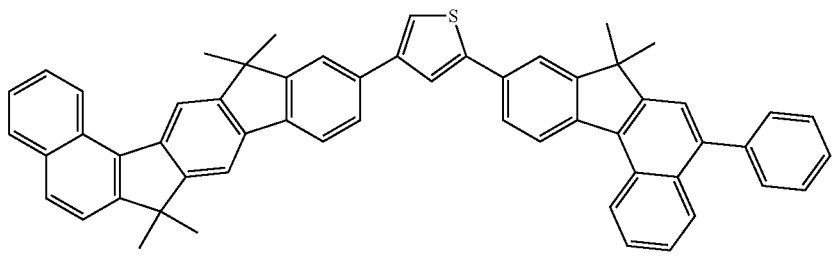 [SMILES: CC1(C)c2cc(-c3csc(-c4ccc5c(c4)C(C)(C)c4cc(-c6ccccc6)c6ccccc6c4-5)c3)ccc2-c2cc3c(cc21)-c1c(ccc2ccccc12)C3(C)C]
68
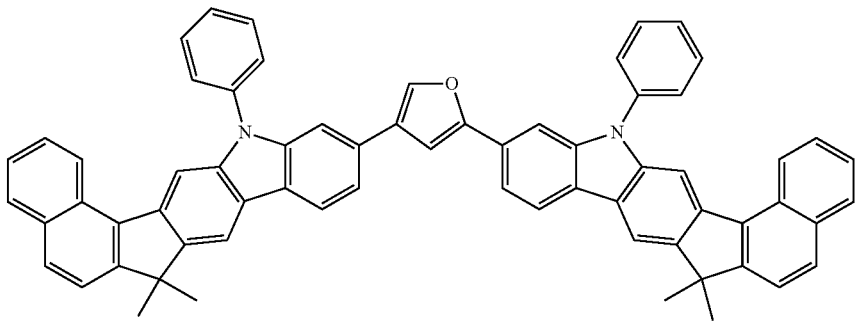 [SMILES: CC1(C)c2cc3c4ccc(-c5coc(-c6ccc7c8cc9c(cc8n(-c8ccccc8)c7c6)-c6c(ccc7ccccc67)C9(C)C)c5)cc4n(-c4ccccc4)c3cc2-c2c1ccc1ccccc21]
69

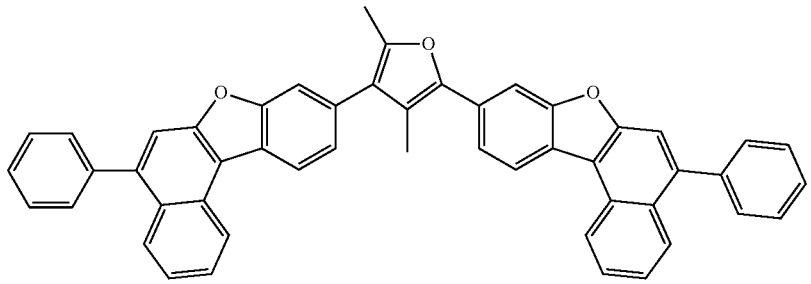 [SMILES: Cc1oc(-c2ccc3c(c2)oc2cc(-c4ccccc4)c4ccccc4c23)c(C)c1-c1ccc2c(c1)oc1cc(-c3ccccc3)c3ccccc3c12]

70

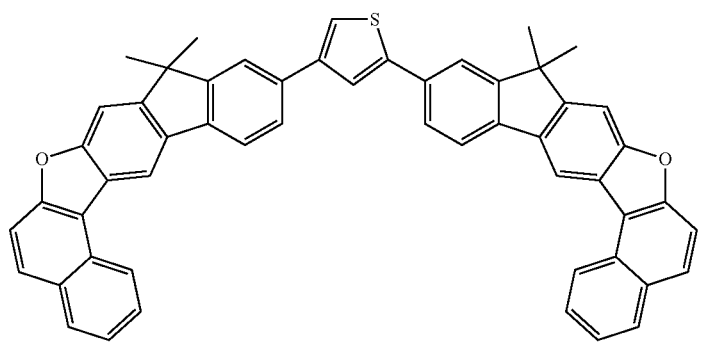 [SMILES: CC1(C)c2cc(-c3csc(-c4ccc5c(c4)C(C)(C)c4cc6oc7ccc8ccccc8c7c6cc4-5)c3)ccc2-c2cc3c(cc21)oc1ccc2ccccc2c13]

71

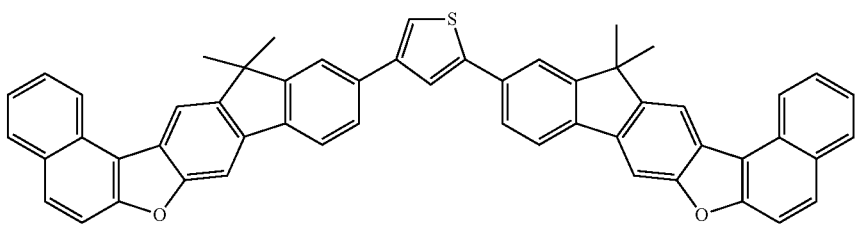 [SMILES: CC1(C)c2cc(-c3csc(-c4ccc5c(c4)C(C)(C)c4cc6c(cc4-5)oc4ccc5ccccc5c46)c3)ccc2-c2cc3oc4ccc5ccccc5c4c3cc21]

72

The present application furthermore relates to a process for the preparation of a compound according to the invention.

The compounds according to the invention can be prepared by means of known synthetic steps of organic chemistry. These include, for example, transition metal-catalysed coupling reactions, such as Suzuki coupling, brominations and halogenations.

Illustrative processes for the preparation of the compounds according to the invention are presented below. The processes shown are particularly suitable for the preparation of the compounds according to the invention. However, alternative processes are conceivable and possibly preferable in certain cases. Accordingly, the person skilled in the art will be able to modify the processes shown below within the scope of his general expert knowledge.

The compounds according to the invention are preferably synthesised as shown in Scheme 1 and Scheme 2. All compounds shown may optionally be substituted by one or more organic radicals.

Scheme 1

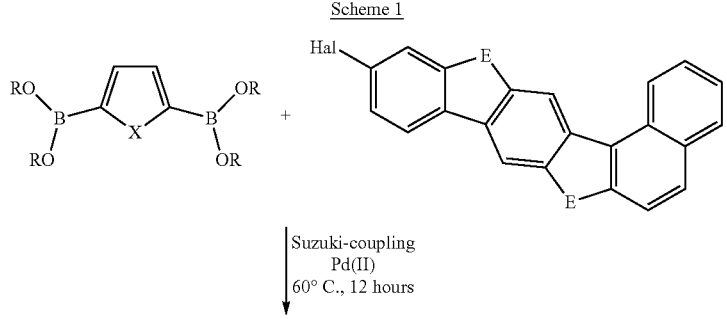

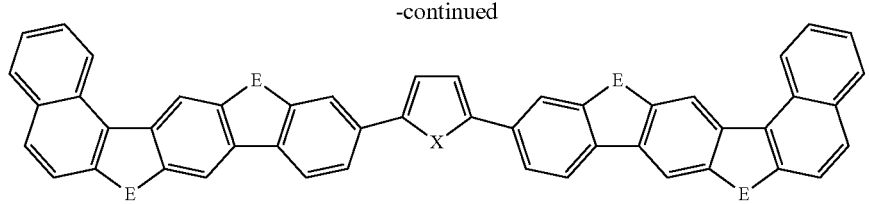

Scheme 2

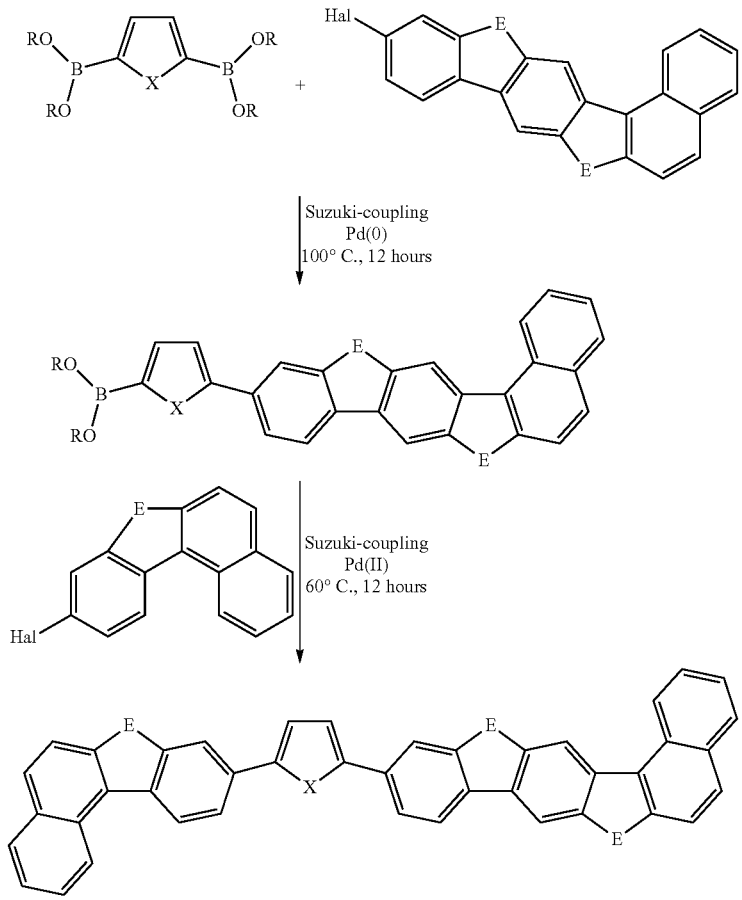

In schemes 1 and 2, "Hal" denotes any desired reactive group, preferably a halogen group, particularly preferably bromine. All compounds shown may optionally be substituted by one or more organic radicals.

In the synthetic process according to Scheme 1, a benzindenofluorene derivative or a benzofluorene derivative is reacted with an heteroaromatic 5-membered ring compound. The C—C coupling reaction between the benzindenofluorene derivative or the benzofluorene derivative with the 5-membered ring is preferably a Suzuki-coupling reaction. In each case, two benzindenofluorene derivatives or benzofluorene derivatives are coupled to an heteroaromatic 5-membered ring in order to give the compound according to the invention.

In the synthetic process according to Scheme 2, a first intermediate compound is synthesized, where one benzindenofluorene derivative or one benzofluorene derivative is reacted with an 5-membered ring heteroaromatic compound via a Suzuki-coupling reaction. In a second step, a benzindenofluorene derivative or a benzofluorene derivative, which is different from the compound used in the first step is reacted with the intermediate compound synthesized in step 1 so that a compound according to the invention is obtained, where two different benzindenofluorene and/or benzofluorene derivatives are coupled to an heteroaromatic 5-membered ring.

The compounds according to the invention described above, in particular compounds which are substituted by reactive leaving groups, such as bromine, iodine, chlorine, boronic acid or boronic acid ester, can be used as monomers for the production of corresponding oligomers, dendrimers or polymers. Suitable reactive leaving groups are, for example, bromine, iodine, chlorine, boronic acids, boronic acid esters, amines, alkenyl or alkynyl groups having a terminal C—C double bond or C—C triple bond, oxiranes, oxetanes, groups which undergo a cycloaddition, for example a 1,3-dipolar cycloaddition, such as, for example, dienes or azides, carboxylic acid derivatives, alcohols and silanes.

The invention therefore furthermore relates to oligomers, polymers or dendrimers containing one or more compounds of the formula (I) or (II), where the bond(s) to the polymer, oligomer or dendrimer may be localised at any desired positions in formula (I) or (II) which are substituted by $R^1$, $R^2$ or $R^3$. Depending on the linking of the compound of the formula (I) or (II), the compound is a constituent of a side chain of the oligomer or polymer or a constituent of the main chain. An oligomer in the sense of this invention is taken to mean a compound which is built up from at least three monomer units. A polymer in the sense of the invention is taken to mean a compound which is built up from at least ten monomer units. The polymers, oligomers or dendrimers according to the invention may be conjugated, partially conjugated or non-conjugated. The oligomers or polymers according to the invention may be linear, branched or dendritic. In the structures linked in a linear manner, the units of the formula (I) or (II) may be linked directly to one another or they may be linked to one another via a divalent group, for example via a substituted or unsubstituted alkylene group, via a heteroatom or via a divalent aromatic or heteroaromatic group. In branched and dendritic structures, for example, three or more units of the formula (I) or (II) may be linked via a trivalent or polyvalent group, for example via a trivalent or polyvalent aromatic or heteroaromatic group, to form a branched or dendritic oligomer or polymer.

The same preferences as described above for compounds of the formula (I) or (II) apply to the recurring units of the formula (I) or (II) in oligomers, dendrimers and polymers.

For the preparation of the oligomers or polymers, the monomers according to the invention are homopolymerised or copolymerised with further monomers. Suitable and preferred comonomers are selected from fluorenes (for example in accordance with EP 842208 or WO 2000/22026), spirobifluorenes (for example in accordance with EP 707020, EP 894107 or WO 2006/061181), para-phenylenes (for example in accordance with WO 1992/18552), carbazoles (for example in accordance with WO 2004/070772 or WO 2004/113468), thiophenes (for example in accordance with EP 1028136), dihydrophenanthrenes (for example in accordance with WO 2005/014689 or WO 2007/006383), cis- and trans-indenofluorenes (for example in accordance with WO 2004/041901 or WO 2004/113412), ketones (for example in accordance with WO 2005/040302), phenanthrenes (for example in accordance with WO 2005/104264 or WO 2007/017066) or also a plurality of these units. The polymers, oligomers and dendrimers usually also contain further units, for example emitting (fluorescent or phosphorescent) units, such as, for example, vinyltriarylamines (for example in accordance with WO 2007/068325) or phosphorescent metal complexes (for example in accordance with. WO 2006/003000), and/or charge-transport units, in particular those based on triarylamines.

The polymers and oligomers according to the invention are generally prepared by polymerisation of one or more types of monomer, at least one monomer of which results in recurring units of the formula (I) or (II) in the polymer. Suitable polymerisation reactions are known to the person skilled in the art and are described in the literature. Particularly suitable and preferred polymerisation reactions which result in C—C or C—N links are the following:
(A) SUZUKI polymerisation;
(B) YAMAMOTO polymerisation;
(C) STILLE polymerisation; and
(D) HARTWIG-BUCHWALD polymerisation.

The way in which the polymerisation can be carried out by these methods and the way in which the polymers can then be separated off from the reaction medium and purified is known to the person skilled in the art and is described in detail in the literature, for example in WO 2003/048225, WO 2004/037887 and WO 2004/037887.

The present invention thus also relates to a process for the preparation of the polymers, oligomers and dendrimers according to the invention, which is characterised in that they are prepared by SUZUKI polymerisation, YAMAMOTO polymerisation, STILLE polymerisation or HARTWIG-BUCHWALD polymerisation. The dendrimers according to the invention can be prepared by processes known to the person skilled in the art or analogously thereto. Suitable processes are described in the literature, such as, for example, in Frechet, Jean M. J.; Hawker, Craig J., "Hyperbranched polyphenylene and hyperbranched polyesters: new soluble, three-dimensional, reactive polymers", Reactive & Functional Polymers (1995), 26(1-3), 127-36; Janssen, H. M.; Meijer, E. W., "The synthesis and characterization of dendritic molecules", Materials Science and Technology (1999), 20 (Synthesis of Polymers), 403-458; Tomalia, Donald A., "Dendrimer molecules", Scientific American (1995), 272(5), 62-6; WO 2002/067343 A1 and WO 2005/026144 A1.

For the processing of the compounds according to the invention from the liquid phase, for example by spin coating or by printing processes, formulations of the compounds according to the invention are necessary. These formulations can be, for example, solutions, dispersions or emulsions. It may be preferred to use mixtures of two or more solvents for this purpose. Suitable and preferred solvents are, for example, toluene, anisole, o-, m- or p-xylene, methyl benzoate, mesitylene, tetralin, veratrol, THF, methyl-THF, THP, chlorobenzene, dioxane, phenoxytoluene, in particular 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetol, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The invention therefore furthermore relates to a formulation, in particular a solution, dispersion or emulsion, comprising at least one compound of the formula (I) or (II) or at least one polymer, oligomer or dendrimer containing at least one unit of the formula (I) or (II), and at least one solvent, preferably an organic solvent. The way in which solutions of this type can be prepared is known to the person skilled in the art and is described, for example, in WO 2002/072714, WO 2003/019694 and the literature cited therein.

The compounds of the formula (I) or (II) according to the invention are suitable for use in electronic devices, in particular in organic electroluminescent devices (OLEDs).

Depending on the substitution, the compounds are employed in different functions and layers.

The invention therefore furthermore relates to the use of a compound of the formula (I) or (II) in an electronic device. The electronic device here is preferably selected from the group consisting of organic integrated circuits (GICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and particularly preferably organic electroluminescent devices (OLEDs).

The invention furthermore relates to an electronic device comprising at least one compound of the formula (I) or (II). The electronic device is preferably selected from the devices indicated above. Particular preference is given to an organic electroluminescent device comprising anode, cathode and at least one emitting layer, characterised in that at least one organic layer comprises at least one compound of the formula (I) or (II).

Apart from cathode, anode and emitting layer, the organic electroluminescent device may also comprise further layers. These are selected, for example, from in each case one or more hole-injection layers, hole-transport layers, hole-blocking layers, electron-transport layers, electron-injection layers, electron-blocking layers, exciton-blocking layers, interlayers, charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n junctions. However, it should be pointed out that each of these layers does not necessarily have to be present and the choice of layers is always dependent on the compounds used and in particular also on whether the electroluminescent device is fluorescent or phosphorescent.

The sequence of the layers of the organic electroluminescent device is preferably the following:
anode-hole-injection layer-hole-transport layer-emitting layer-electron-transport layer-electron-injection layer-cathode.

It should again be pointed out here that not all the said layers have to be present, and/or that further layers may additionally be present.

The organic electroluminescent device according to the invention may comprise a plurality of emitting layers. These emission layers in this case particularly preferably have in total a plurality of emission maxima between 380 nm and 750 nm, resulting overall in white emission, i.e. various emitting compounds which are able to fluoresce or phosphoresce and which emit blue or yellow or orange or red light are used in the emitting layers. Particular preference is given to three-layer systems, i.e. systems having three emitting layers, where at least one of these layers preferably comprises at least one compound of the formula (I) or (II) and where the three layers exhibit blue, green and orange or red emission (for the basic structure see, for example, WO 2005/011013). It should be noted that, for the generation of white light, an emitter compound used individually which emits in a broad wavelength range may also be suitable instead of a plurality of emitter compounds emitting in colour.

The compounds according to the invention may alternatively and/or additionally also be present in the hole-transport layer or in another layer.

It is preferred for the compound of the formula (I) or (II) to be employed in an emitting layer. In particular, the compound of the formula (I) or (II) is suitable for use as emitting material (emitter compound).

The compound according to the invention is particularly suitable for use as blue-emitting emitter compound. The electronic device concerned may comprise a single emitting layer comprising the compound according to the invention or it may comprise two or more emitting layers. The further emitting layers here may comprise one or more compounds according to the invention or alternatively other compounds.

If the compound according to the invention is employed as emitting material in an emitting layer, it is preferably employed in combination with one or more matrix materials.

The proportion of the compound according to the invention in the mixture of the emitting layer is in this case preferably between 0.1 and 50.0% by vol., particulary preferably between 0.5 and 20.0% by vol., very particularly preferably between 1.0 and 10.0% by vol. Correspondingly, the proportion of the matrix material or matrix materials is between 50.0 and 99.9% by vol., particularly preferably between 80.0 and 99.5% by vol., very particularly preferably between 90.0 and 99.0% by vol.

Preferred matrix materials for use in combination with the materials according to the invention as emitters are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 2004/081017), the hole-conducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benzanthracenes (for example in accordance with WO 2008/145239). Particularly preferred matrix materials are selected from the classes of the oligoarylenes, comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes, comprising anthracene, benzanthracene, benzophenanthrene and/or pyrene or atropisomers of these compounds. An oligoarylene in the sense of this invention is intended to be taken to mean a compound in which at least three aryl or arylene groups are bonded to one another.

Preferred matrix materials for use in combination with the compound of the formula (I) or (II) in the emitting layer are depicted in the following table.

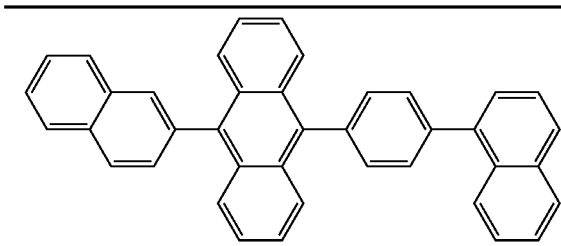

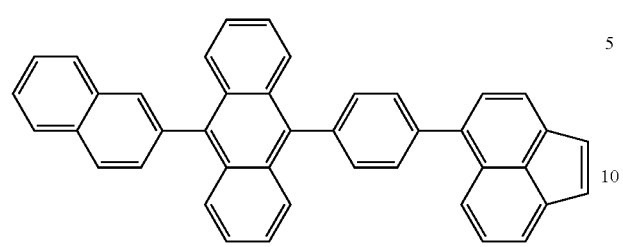
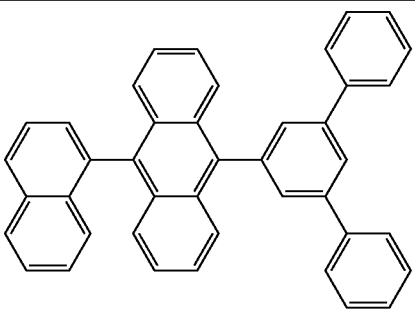
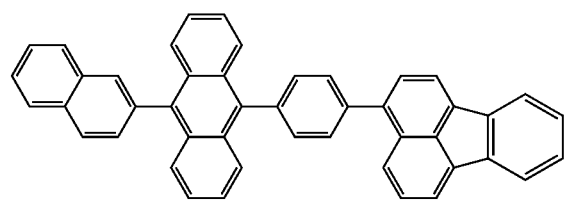 [SMILES: c1ccc2c(c1)-c1cccc3c(-c4ccc(-c5c6ccccc6c(-c6ccc7ccccc7c6)c6ccccc56)cc4)ccc-2c13]
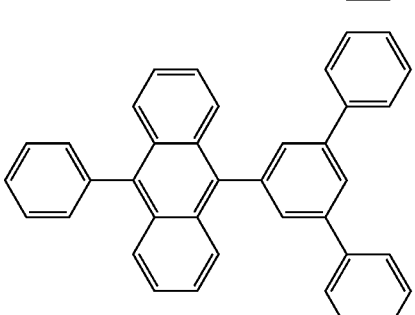
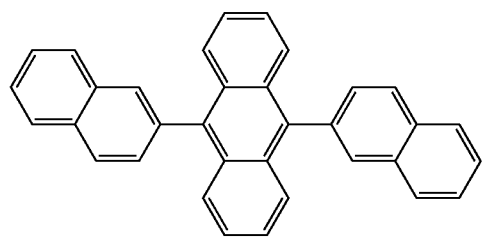 [SMILES: c1ccc2cc(-c3c4ccccc4c(-c4ccc5ccccc5c4)c4ccccc34)ccc2c1]
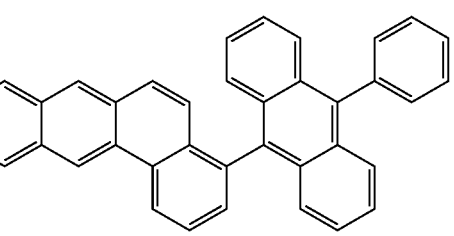
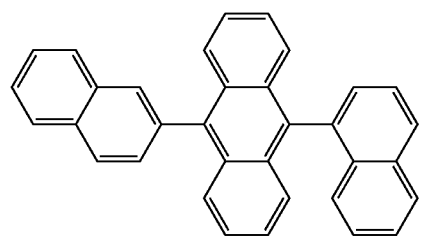 [SMILES: c1ccc2cc(-c3c4ccccc4c(-c4cccc5ccccc45)c4ccccc34)ccc2c1]
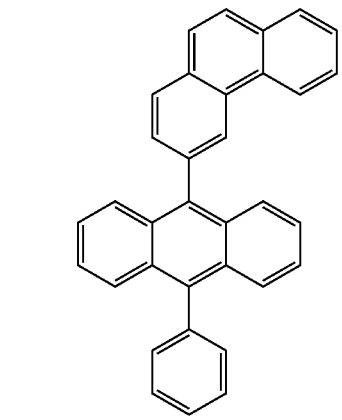 [SMILES: c1ccc(-c2c3ccccc3c(-c3ccc4ccc5ccccc5c4c3)c3ccccc23)cc1]
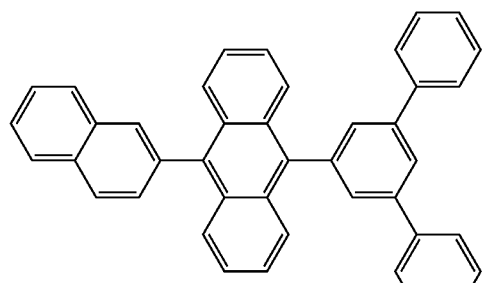
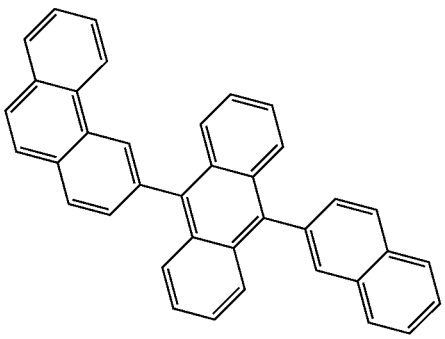 [SMILES: c1ccc2cc(-c3c4ccccc4c(-c4ccc5ccc6ccccc6c5c4)c4ccccc34)ccc2c1]
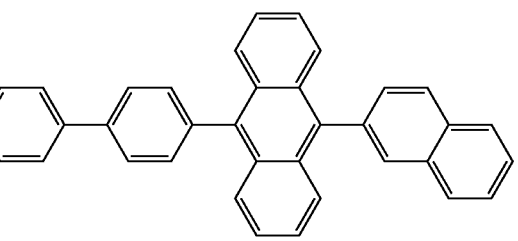

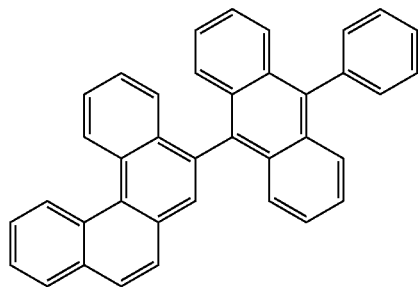 [SMILES: c1ccc(-c2c3ccccc3c(-c3cc4ccc5ccccc5c4c4ccccc34)c3ccccc23)cc1]
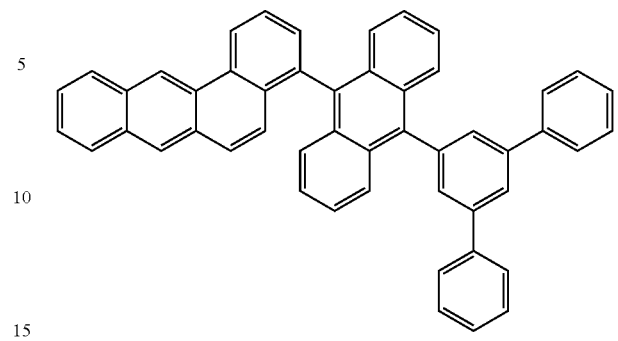
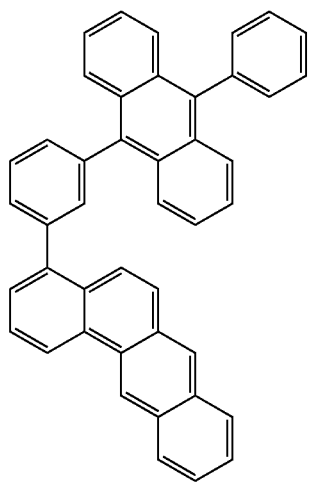 [SMILES: c1ccc(-c2c3ccccc3c(-c3cccc(-c4cccc5c4ccc4cc6ccccc6cc45)c3)c3ccccc23)cc1]
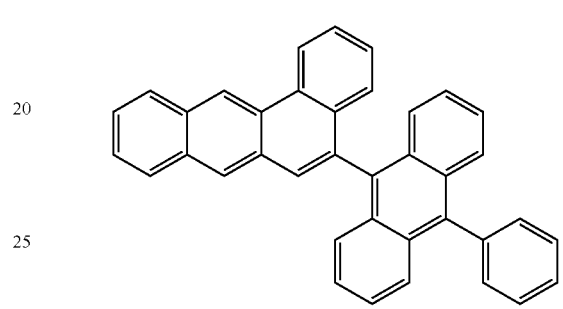
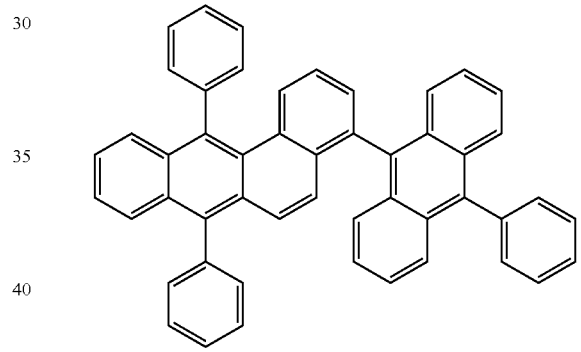
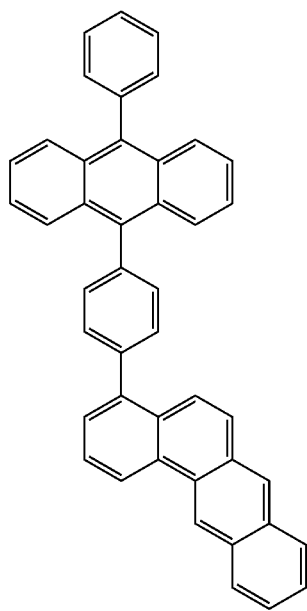 [SMILES: c1ccc(-c2c3ccccc3c(-c3ccc(-c4cccc5c4ccc4cc6ccccc6cc45)cc3)c3ccccc23)cc1]
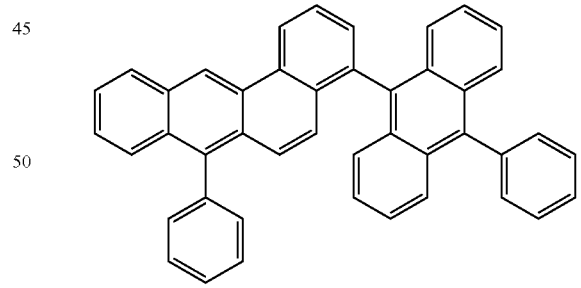
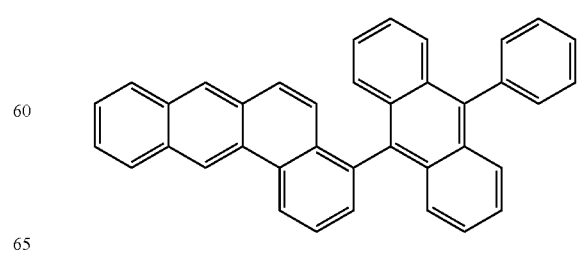

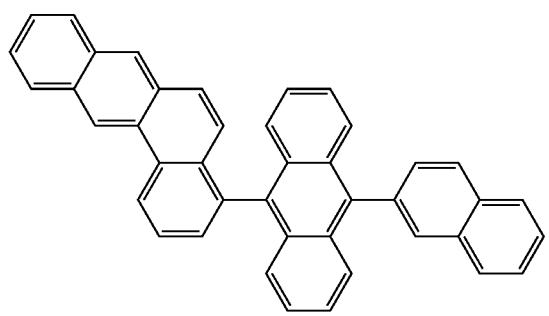 [SMILES: c1ccc2cc(-c3c4ccccc4c(-c4cccc5c4ccc4cc6ccccc6cc45)c4ccccc34)ccc2c1]
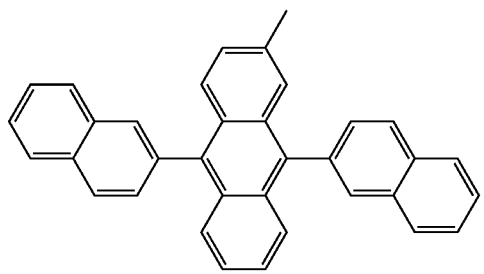
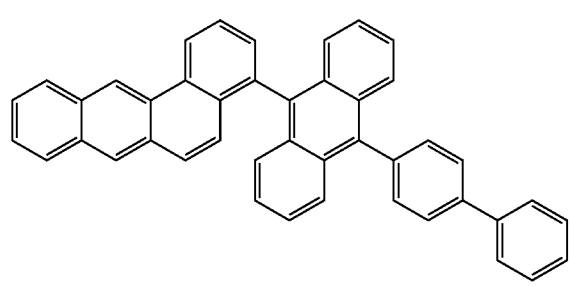 [SMILES: c1ccc(-c2ccc(-c3c4ccccc4c(-c4cccc5c4ccc4cc6ccccc6cc45)c4ccccc34)cc2)cc1]
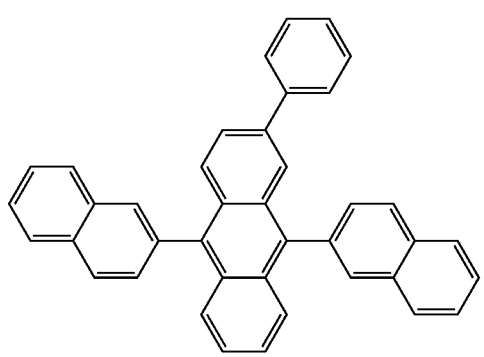
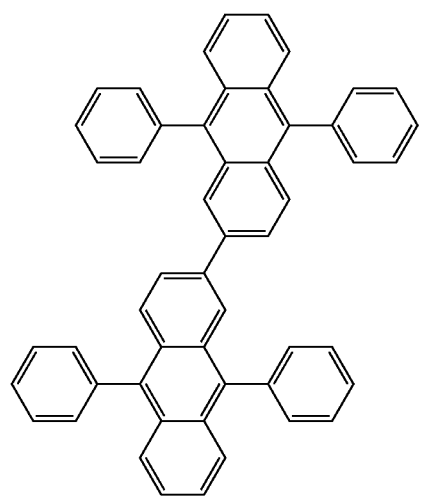 [SMILES: c1ccc(-c2c3ccccc3c(-c3ccccc3)c3cc(-c4ccc5c(-c6ccccc6)c6ccccc6c(-c6ccccc6)c5c4)ccc23)cc1]
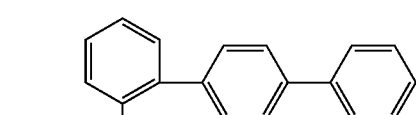
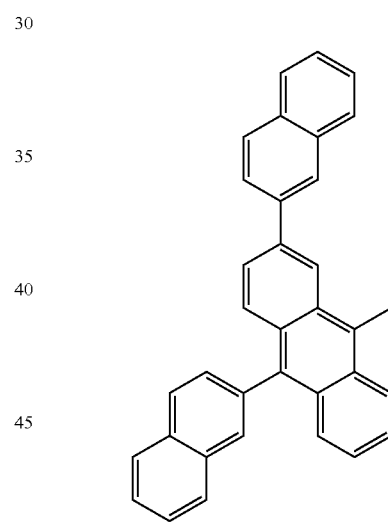
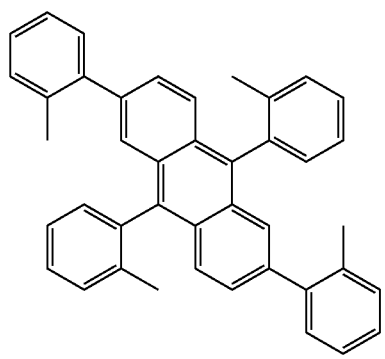 [SMILES: Cc1ccccc1-c1ccc2c(-c3ccccc3C)c3cc(-c4ccccc4C)ccc3c(-c3ccccc3C)c2c1]

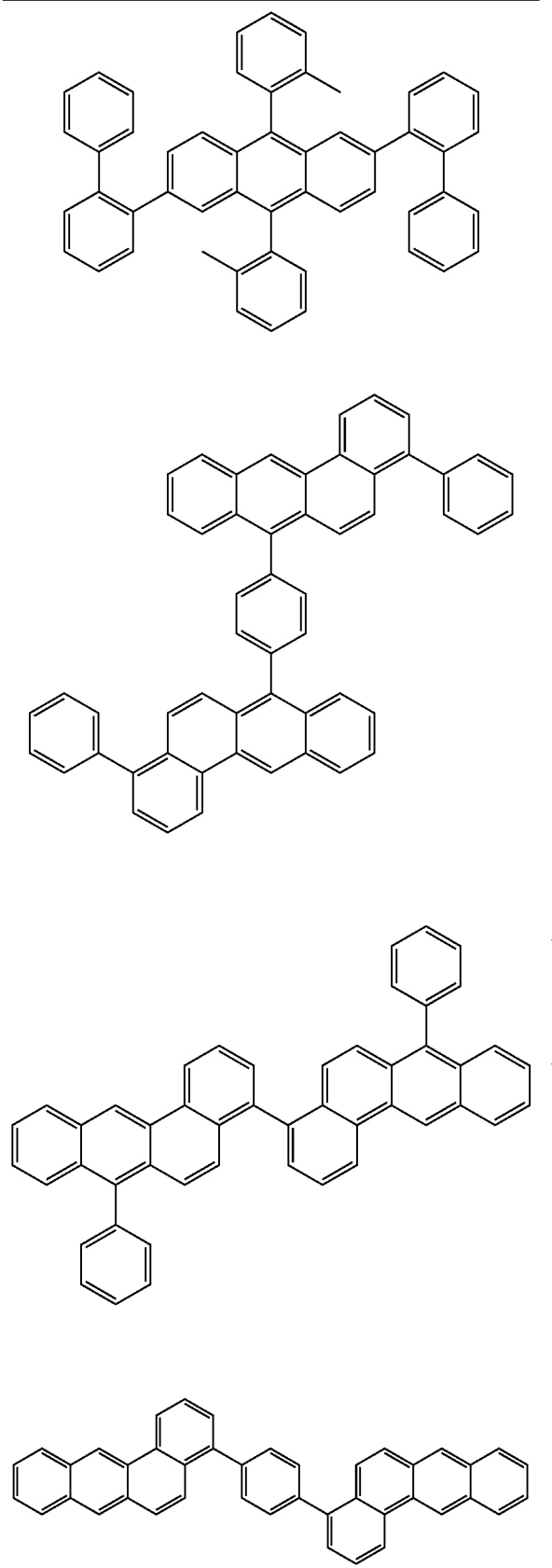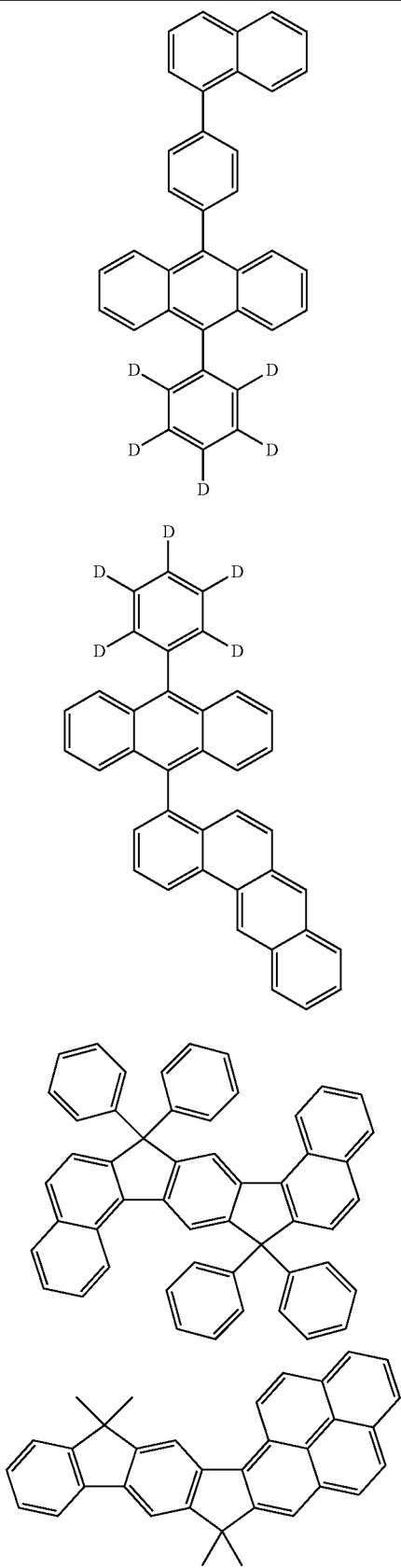

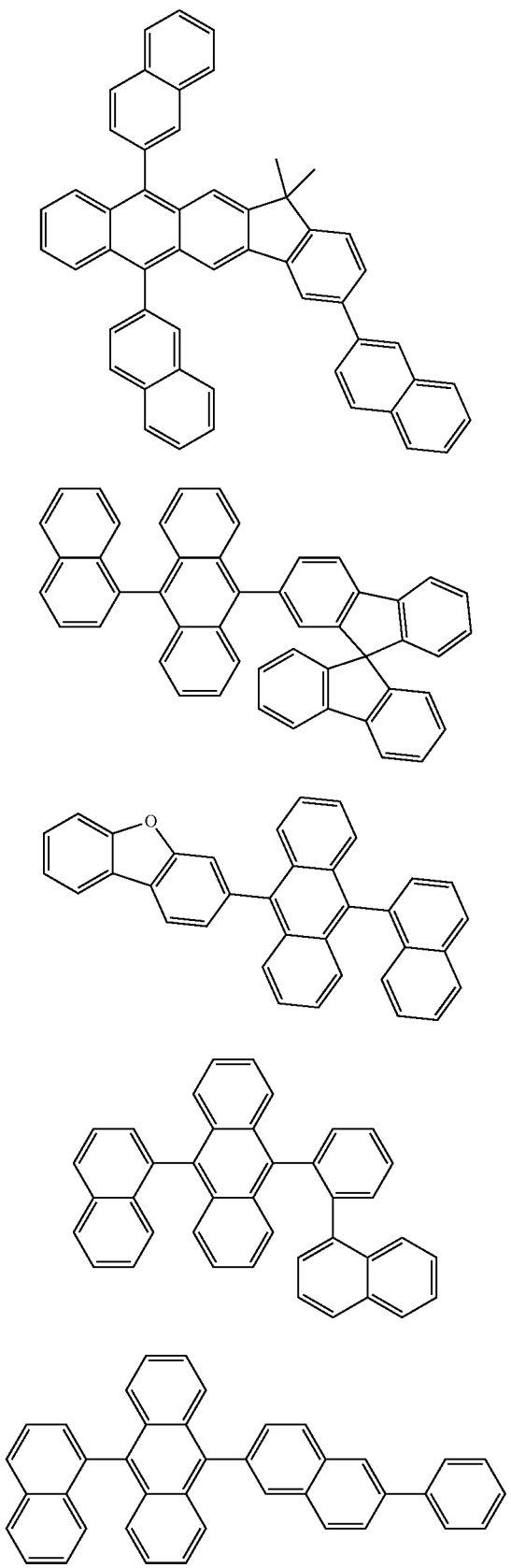
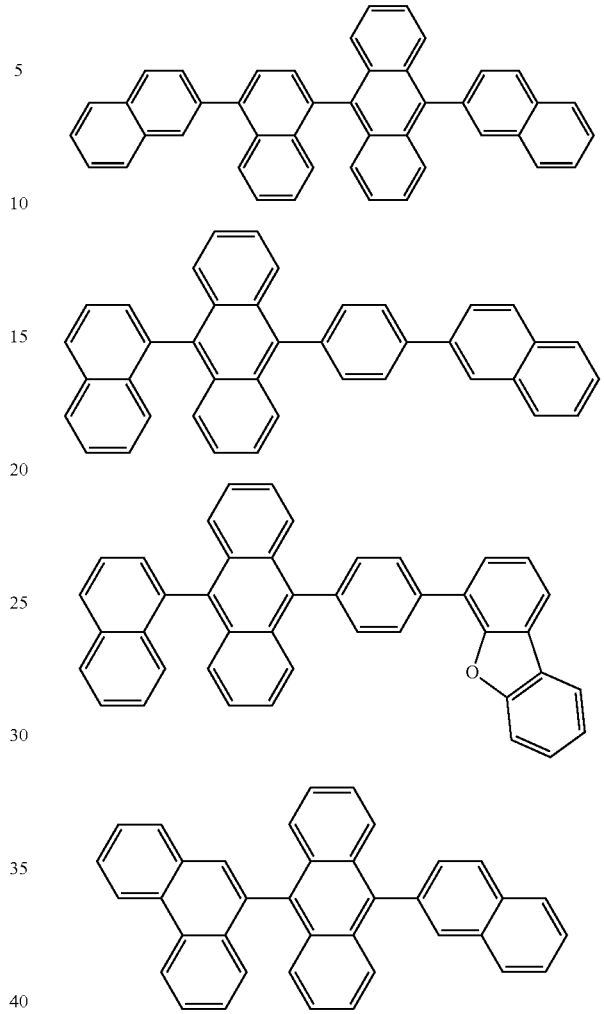

The compounds according to the invention can also be employed in other layers, for example as hole-transport materials in a hole-injection or hole-transport layer or electron-blocking layer or as matrix materials in an emitting layer, preferably as matrix materials for fluorescent emitters.

If the compound of the formula (I) or (II) is employed as hole-transport material in a hole-transport layer, a hole-injection layer or an electron-blocking layer, the compound can be employed as pure material, i.e. in a proportion of 100%, in the hole-transport layer, or it can be employed in combination with one or more further compounds. According to a preferred embodiment, the organic layer comprising the compound of the formula (I) or (II) then additionally comprises one or more p-dopants. The p-dopants employed in accordance with the present invention are preferably organic electron-acceptor compounds which are able to oxidise one or more of the other compounds of the mixture.

Particularly preferred embodiments of p-dopants are the compounds disclosed in WO 2011/073149, EP 1968131, EP 2276085, EP 2213662, EP 1722602, EP 2045848, DE 102007031220, U.S. Pat. No. 8,044,390, U.S. Pat. No. 8,057,712, WO 2009/003455, WO 2010/094378, WO 2011/120709, US 2010/0096600 and WO 2012/095143.

If the compound of the formula (I) or (II) is employed as matrix material in combination with a phosphorescent emitter in an emitting layer, the phosphorescent emitter is preferably selected from the classes and embodiments of phosphorescent emitters indicated below. Furthermore, one or more further matrix materials are preferably present in the emitting layer in this case.

So-called mixed-matrix systems of this type preferably comprise two or three different matrix materials, particularly preferably two different matrix materials. It is preferred here for one of the two materials to be a material having hole-transporting properties and for the other material to be a material having electron-transporting properties. The compound of the formula (I) or (II) is preferably the material having hole-transporting properties.

However, the desired electron-transporting and hole-transporting properties of the mixed-matrix components may also be combined mainly or completely in a single mixed-matrix component, where the further mixed-matrix component or components satisfy other functions. The two different matrix materials may be present here in a ratio of 1:50 to 1:1, preferably 1:20 to 1:1, particularly preferably 1:10 to 1:1 and very particularly preferably 1:4 to 1:1. Mixed-matrix systems are preferably employed in phosphorescent organic electroluminescent devices. Further details on mixed-matrix systems are contained, inter alia, in the application WO 2010/108579.

Particularly suitable matrix materials which can be used as matrix components of a mixed-matrix system in combination with the compounds according to the invention are selected from the preferred matrix materials for phosphorescent emitters indicated below or the preferred matrix materials for fluorescent emitters, depending on what type of emitter compound is employed in the mixed-matrix system.

Generally preferred classes of material for use as corresponding functional materials in the organic electroluminescent devices according to the invention are indicated below.

Suitable phosphorescent emitters are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent emitters used are preferably compounds which contain copper, molybdenum, tungsten, rhenium, ruthenium, osmium, rhodium, iridium, palladium, platinum, silver, gold or europium, in particular compounds which contain iridium, platinum or copper.

For the purposes of the present invention, all luminescent iridium, platinum or copper complexes are regarded as phosphorescent compounds.

Examples of the phosphorescent emitters described above are revealed by the applications WO 2000/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as used in accordance with the prior art for phosphorescent OLEDs and as are known to the person skilled in the art in the area of organic electroluminescent devices are suitable for use in the devices according to the invention. The person skilled in the art will also be able to employ further phosphorescent complexes without inventive step in combination with the compounds according to the invention in OLEDs.

Preferred fluorescent emitters, besides the compounds according to the invention, are selected from the class of the arylamines. An arylamine or aromatic amine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position.

Preferred matrix materials for use with fluorescent emitters compounds are indicated above.

Preferred matrix materials for phosphorescent emitters are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example in accordance with WO 2007/063754 or WO 2008/056746, indenocarbazole derivatives, for example in accordance with WO 2010/136109, WO 2011/000455 or WO 2013/041176, azacarbazole derivatives, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, diazasilole or tetraazasilole derivatives, for example in accordance with WO 2010/054729, diazaphosphole derivatives, for example in accordance with WO 2010/054730, bridged carbazole derivatives, for example in accordance with US 2009/0136779, WO 2010/050778, WO 2011/042107, WO 2011/088877 or WO 2012/143080, triphenylene derivatives, for example in accordance with WO 2012/048781, or lactams, for example in accordance with WO 2011/116865 or WO 2011/137951.

Besides the compounds according to the invention, suitable charge-transport materials, as can be used in the hole-injection or hole-transport layer or electron-blocking layer or in the electron-transport layer of the electronic device according to the invention, are, for example, the compounds disclosed in Y. Shirota et al., Chem. Rev. 2007, 107(4), 953-1010, or other materials as are employed in these layers in accordance with the prior art.

Materials which can be used for the electron-transport layer are all materials as are used in accordance with the prior art as electron-transport materials in the electron-transport layer. Particularly suitable are aluminium complexes, for example $Alq_3$, zirconium complexes, for example $Zrq_4$, lithium complexes, for example Liq, benzimidazole derivatives, triazine derivatives, pyrimidine derivatives, pyridine derivatives, pyrazine derivatives, quinoxaline derivatives, quinoline derivatives, oxadiazole derivatives, aromatic ketones, lactams, boranes, diazaphosphole derivatives and phosphine oxide derivatives. Furthermore suitable materials are derivatives of the above-mentioned compounds, as disclosed in JP 2000/053957, WO 2003/060956, WO 2004/028217, WO 2004/080975 and WO 2010/072300.

Preferred hole-transport materials which can be used in a hole-transport, hole-injection or electron-blocking layer in the electroluminescent device according to the invention are indenofluorenamine derivatives (for example in accordance with WO 06/122630 or WO 06/100896), the amine derivatives disclosed in EP 1661888, hexaazatriphenylene derivatives (for example in accordance with WO 01/049806), amine derivatives containing condensed aromatic rings (for example in accordance with U.S. Pat. No. 5,061,569), the amine derivatives disclosed in WO 95/09147, monobenzo-indenofluorenamines (for example in accordance with WO 08/006449), dibenzoindenofluorenamines (for example in accordance with WO 07/140847), spirobifluorenamines (for example in accordance with WO 2012/034627 or WO 2013/120577), fluorenamines (for example in accordance with the as yet unpublished applications EP 12005369.9, EP 12005370.7 and EP 12005371.5), spirodibenzopyranamines (for example in accordance with WO 2013/083216) and dihydroacridine derivatives (for example in accordance with WO 2012/150001). The compounds according to the invention can also be used as hole-transport materials.

The cathode of the organic electroluminescent device preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag, Mg/Ag or Ag/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example $Al/Ni/NiO_x$, $Al/PtO_x$) may also be preferred. For some applications, at least one of the electrodes must be transparent or partially transparent in order to facilitate either irradiation of the organic material (organic solar cells) or the coupling-out of light (OLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive doped polymers.

The device is appropriately (depending on the application) structured, provided with contacts and finally sealed, since the lifetime of the devices according to the invention is shortened in the presence of water and/or air.

In a preferred embodiment, the organic electroluminescent device according to the invention is characterised in that one or more layers are coated by means of a sublimation process, in which the materials are applied by vapour deposition in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds of the formula (I) or (II) are necessary for this purpose. High solubility can be achieved through suitable substitution of the compounds.

For the production of an organic electroluminescent device according to the invention, it is furthermore preferred to apply one or more layers from solution and one or more layers by a sublimation process.

In accordance with the invention, the electronic devices comprising one or more compounds according to the invention can be employed in displays, as light sources in lighting applications and as light sources in medical and/or cosmetic applications (for example light therapy).

WORKING EXAMPLES

A) Synthesis Examples

A-1) Variant I:

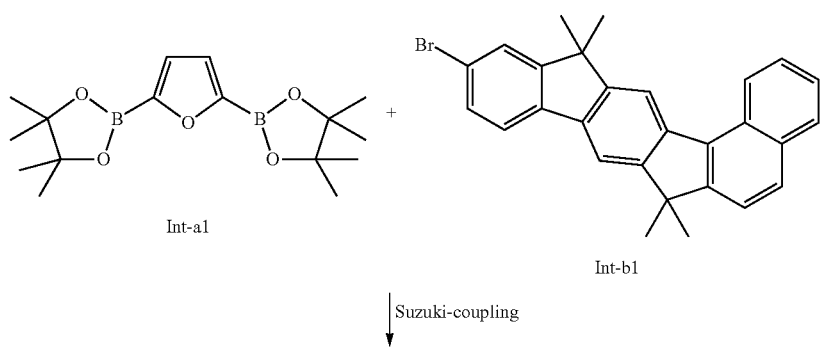

Int-a1

Int-b1

Suzuki-coupling

-continued

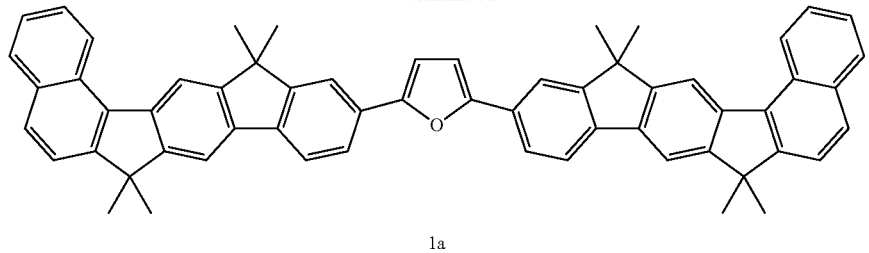

1a

Synthesis of Compound 1a

Compound Int-b1 (43.25 g, 98.44 mmol), Compound Int-a1 (15 g, 46.88 mmol), sodium metaborate tetrahydrate (19.39 g, 140.63 mmol) and hydrazine hydroxide are suspended in 200 mL of water and 600 mL of tetrahydrofuran. The solution is then degassed and argon-saturated.

Bis(triphenylphosphin)palladium(II) chloride (1.32 g, 1.88 mmol) is then added to the reaction mixture and the mixture is heated overnight at 60° C. The suspension is then cooled, filtrated and the rest is extracted in a Soxhlet extractor with chlorobenzene. Finally, the solid product is stirred and heated in chlorobenzene. As a result, a yellow solid (purity 99.55%, HPLC) is obtained with a yield of 9.91 g (12.6 mmol, 25%).

Synthesis of Compounds 1b to 1k

The compounds 1b to 1k (see below) are synthesised analogously to the process described above for the synthesis of compound 1a.

The structure of the different intermediate products is given below.

| Intermediate compounds | | Synthesis |
|---|---|---|
| Int-a1 | | Adv. Synth. Catal. 2003, 345, 1103-1106 |
| Int-a2 | | Org. Lett. 2013, 15, 5970-5973 |
| Int-a3 | | Commercially available |
| Int-a4 | | J. Am. CHem. Soc. 2009, 131, 6070-6071 |
| Int-a5 | | Tetrahedron 2012, 68, 9982-9998 und Adv. Synth. Catal. 2003, 345, 1103-1106 |

-continued
| Intermediate compounds | | Synthesis |
|---|---|---|
| Int-a6 | 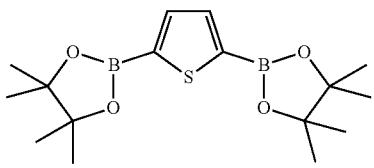 | Commercialy available |
| Int-b1 | 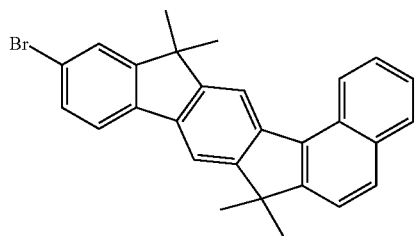 [SMILES: CC1(C)c2cc(Br)ccc2-c2cc3c(cc21)-c1c(ccc2ccccc12)C3(C)C] | WO2014/037077 |
| Int-b2 | 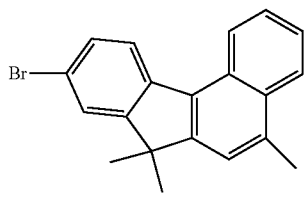 [SMILES: Cc1cc2c(c3ccccc13)-c1ccc(Br)cc1C2(C)C] | WO2010/049050 |
| Int-b3 | 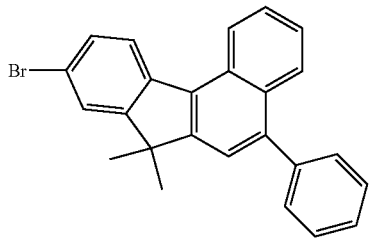 [SMILES: CC1(C)c2cc(Br)ccc2-c2c1cc(-c1ccccc1)c1ccccc21] | WO2014/106522 |
| Int-b4 | 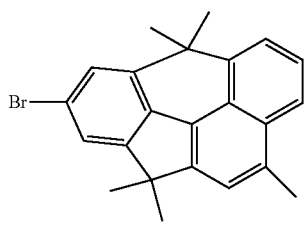 [SMILES: Cc1cc2c3c4c(cccc14)C(C)(C)c1cc(Br)cc(c1-3)C2(C)C] | WO2010/049050 |
| Int-b5 | 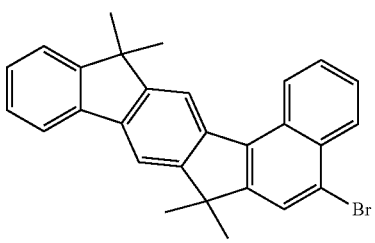 [SMILES: CC1(C)c2ccccc2-c2cc3c(cc21)-c1c(cc(Br)c2ccccc12)C3(C)C] | WO2008/006449 |

| Intermediate compounds | Synthesis |
|---|---|
| Int-b6 | WO2014/037077 |
| Int-b7 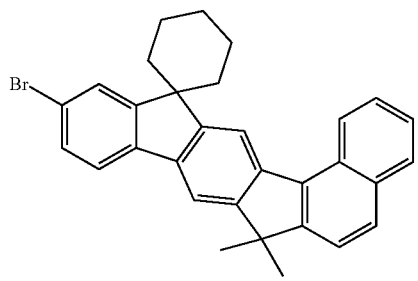 [SMILES: CC1(C)c2cc3c(cc2-c2c1ccc1ccccc21)C1(CCCCC1)c1cc(Br)ccc1-3] | WO2013065589 |
| 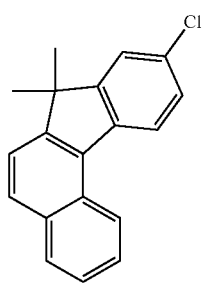 [SMILES: CC1(C)c2cc(Cl)ccc2-c2c1ccc1ccccc21] | |
The following table represents the structure of the compounds 1a to 1 k as well as the corresponding yields.
| | Yield % |
|---|---|
| Int-a1 Int-b1 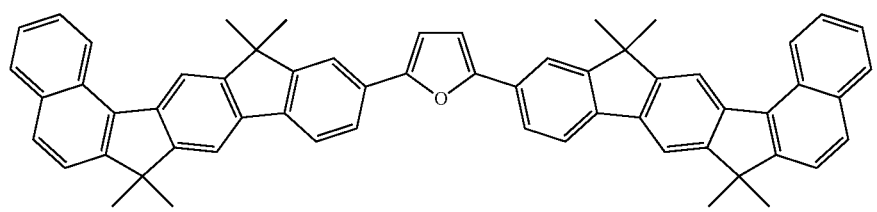<br>1a | 25 |
| Int-a1 Int-b2 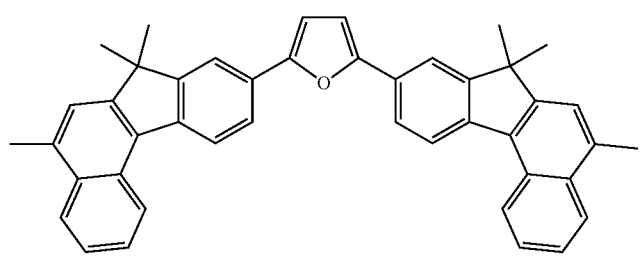<br>1b | 43 |

-continued
| | | Yield % |
|---|---|---|
| Int-a1 Int-b6 | 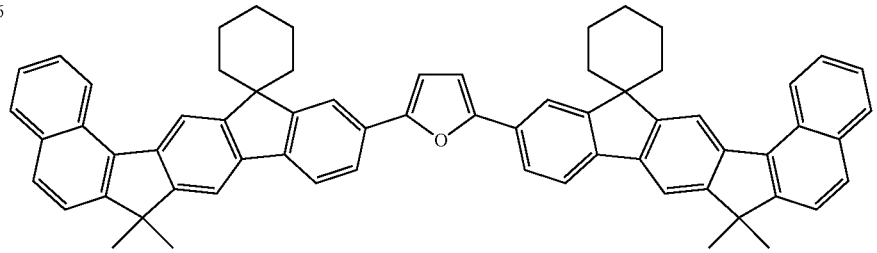<br>1c | 32 |
| Int-a2 Int-b1 | 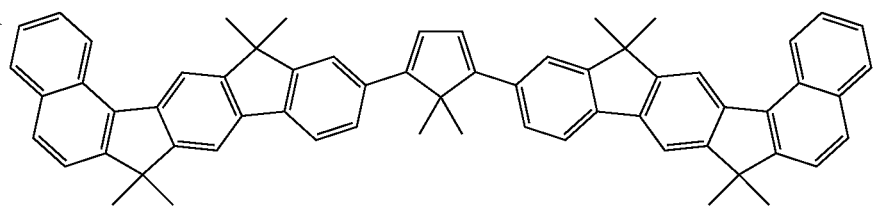<br>1d | 48 |
| Int-a3 Int-b4 | 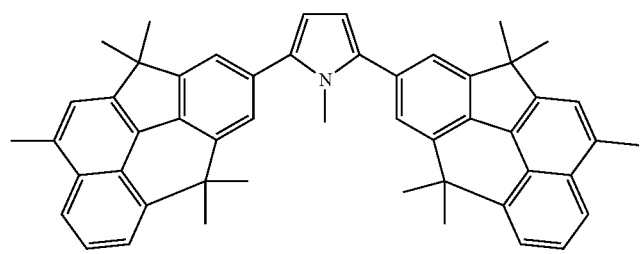<br>1e | 18 |
| Int-a4 Int-b3 | 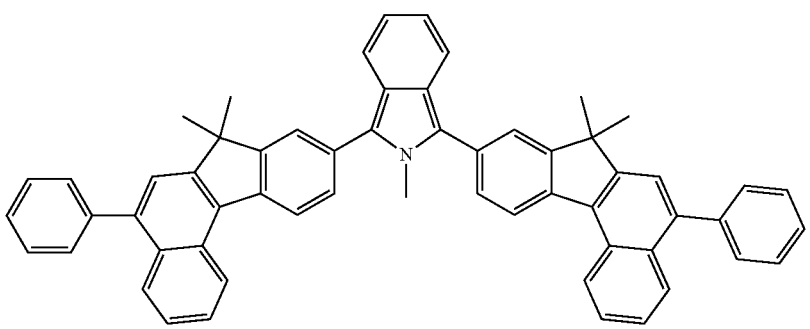 [SMILES: Cn1c(-c2ccc3c(c2)C(C)(C)c2cc(-c4ccccc4)c4ccccc4c2-3)c2ccccc2c1-c1ccc2c(c1)C(C)(C)c1cc(-c3ccccc3)c3ccccc3c1-2]<br>1f | 27 |
| Int-a4 Int-b5 | 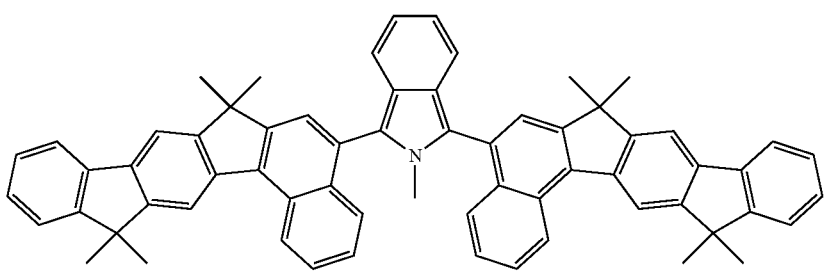 [SMILES: Cn1c(-c2cc3c(c4ccccc24)-c2cc4c(cc2C3(C)C)-c2ccccc2C4(C)C)c2ccccc2c1-c1cc2c(c3ccccc13)-c1cc3c(cc1C2(C)C)-c1ccccc1C3(C)C]<br>1g | 38 |

-continued
| | | Yield % |
|---|---|---|
| Int-a5 Int-b1 | 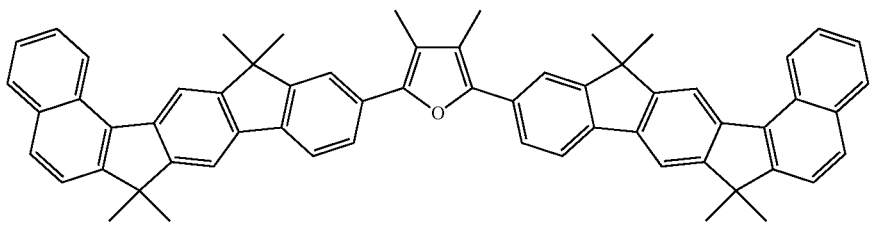 [SMILES: Cc1c(-c2ccc3c(c2)C(C)(C)c2cc4c(cc2-3)C(C)(C)c2ccc3ccccc3c2-4)oc(-c2ccc3c(c2)C(C)(C)c2cc4c(cc2-3)C(C)(C)c2ccc3ccccc3c2-4)c1C] 1h | 31 |
| Int-a5 Int-b3 | 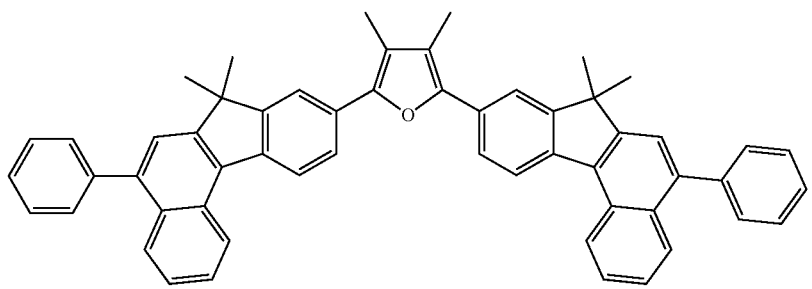 [SMILES: Cc1c(-c2ccc3c(c2)C(C)(C)c2cc(-c4ccccc4)c4ccccc4c2-3)oc(-c2ccc3c(c2)C(C)(C)c2cc(-c4ccccc4)c4ccccc4c2-3)c1C] 1i | 27 |
| Int-a6 Int-b1 | 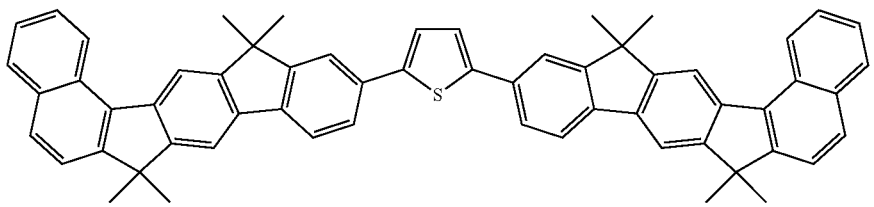 [SMILES: CC1(C)c2cc(-c3ccc(-c4ccc5c(c4)C(C)(C)c4cc6c(cc4-5)C(C)(C)c4ccc5ccccc5c4-6)s3)ccc2-c2cc3c(cc21)-c1c(ccc2ccccc12)C3(C)C] 1j | 44 |
| Int-a6 Int-b4 | 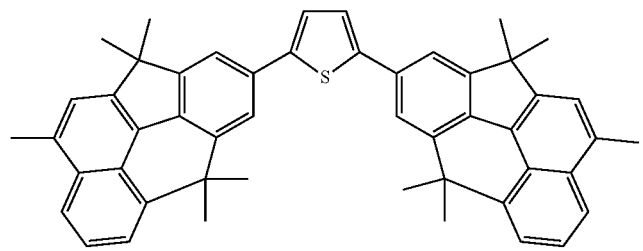 1k | 39 |
| Int-a1 Int-b7 | 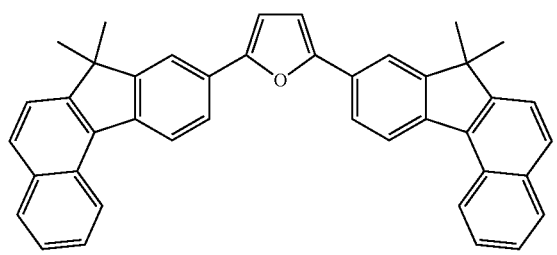 [SMILES: CC1(C)c2cc(-c3ccc(-c4ccc5c(c4)C(C)(C)c4ccc6ccccc6c4-5)o3)ccc2-c2c1ccc1ccccc21] 1l | 37 |

A-2) Variant II:
First Step

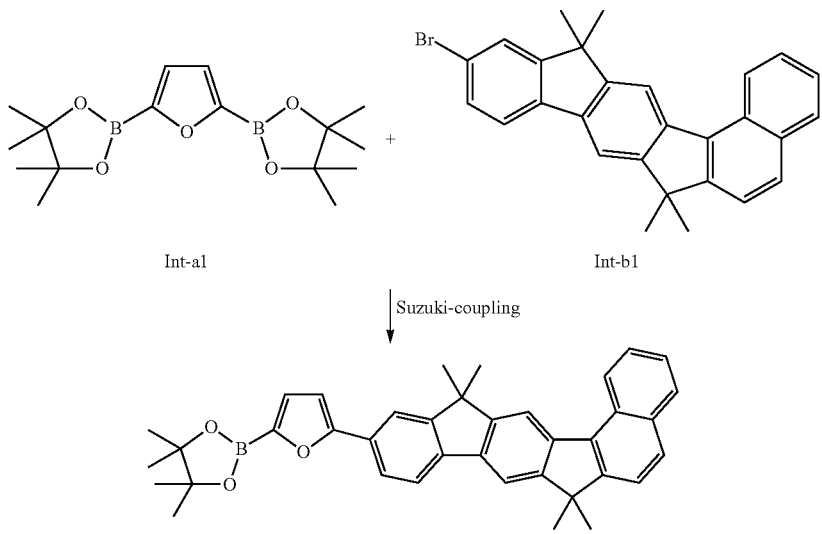

Second Step

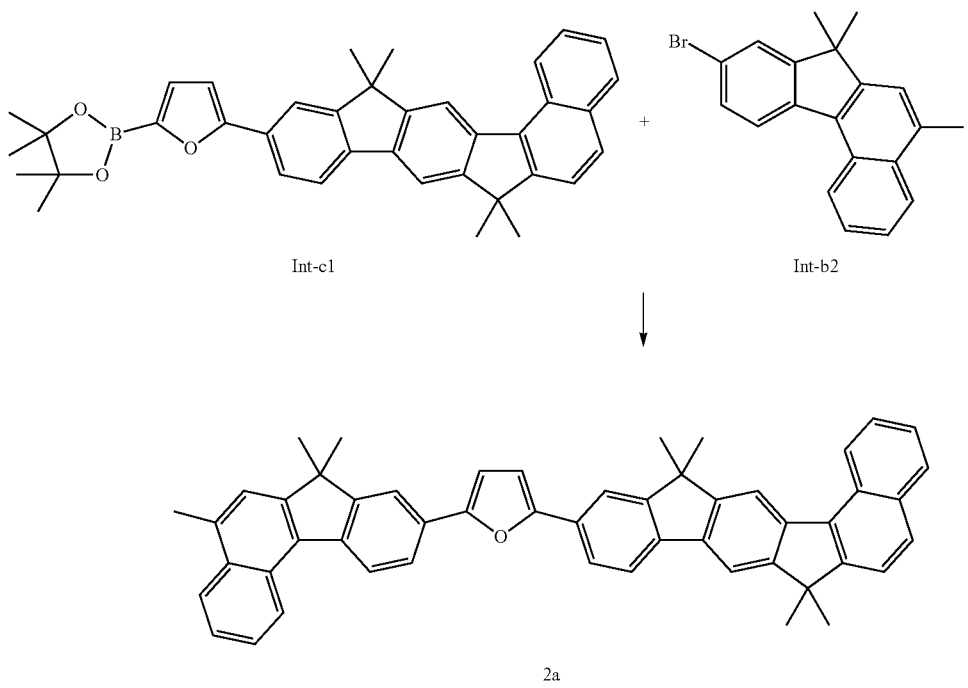

Synthesis of the Intermediate Compound Int-c1

Compound Int-b1 (13.73 g, 31.25 mmol), Compound Int-a1 (10 g, 31.25 mmol) and potassium carbonate (6.47 g, 46.87 mmol) are suspended in 250 mL of water and 250 mL of tetrahydrofuran. The solution is then degassed and argon-saturated. Tetrakis(triphenylphosphin)palladium(0) chloride (1.08 g, 0.94 mmol) is then added to the reaction mixture and the mixture is heated overnight at 100° C. The mixture is then cooled, the aqueous and organic phases are separated and the aqueous phase is extracted several times with toluene. After removing the solvent, the rest is extracted in a Soxhlet extractor with toluene and recrystallized once from toluene. As a result, a yellow solid (purity 98%, HPLC) is obtained with a yield of 14.16 g (15.62 mmol, 82%).

Synthesis of Intermediate Compounds Int-c2 to Int-c4

The intermediate compounds Int-c2 to Int-c4 (see below) are synthesised analogously to the process described above for the synthesis of the intermediate compound Int-c1.

The structure of the different intermediate products and their respective yield is given in the table below.

| Int-a | Int-b | Int-c | Yield % |
|---|---|---|---|
| Int-a1 | Int-b1 | 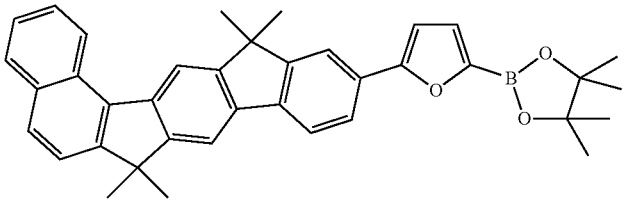 [SMILES: CC1(C)c2cc(-c3ccc(B4OC(C)(C)C(C)(C)O4)o3)ccc2-c2cc3c(cc21)-c1c(ccc2ccccc12)C3(C)C]<br>Int-c1 | 82 |
| Int-a2 | Int-b1 | 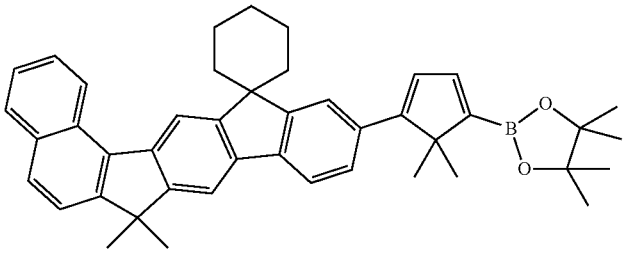 [SMILES: CC1(C)C(B2OC(C)(C)C(C)(C)O2)=CC=C1c1ccc2c(c1)C1(CCCCC1)c1cc3c(cc1-2)C(C)(C)c1ccc2ccccc2c1-3]<br>Int-c2 | 75 |
| Int-a4 | Int-b3 | 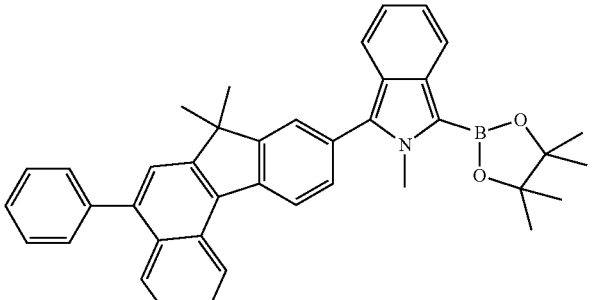<br>Int-c3 | 87 |
| Int-a6 | Int-b4 | 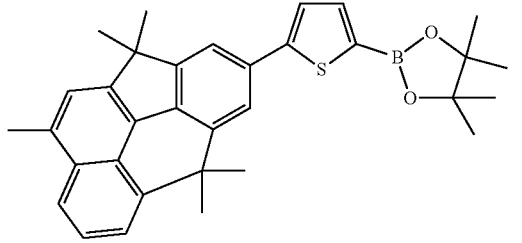<br>Int-c4 | 62 |

Synthesis of Compound 2a

Int-b2 (9.50 g, 28.18 mmol), Int-c1 (14.16 g, 25.62 mmol), sodium metaborate tetrahydrate (5.29 g, 38.43 mmol) and hydrazine hydroxide are suspended in 100 mL of water and 300 mL of tetrahydrofuran. The solution is then degassed and argon-saturated. Bis(triphenylphosphin)palladium(II) chloride (0.36 g, 0.51 mmol) is then added to the reaction mixture and the mixture is heated overnight at 60° C. The suspension is then cooled, filtrated and the rest is extracted in a Soxhlet extractor with chlorobenzene. Finally, the solid product is stirred and heated in chlorobenzene. As a result, a yellow solid (purity 99.89%, HPLC) is obtained with a yield of 9.01 g (13.32 mmol, 52%).

Synthesis of Compound 2b to 2e

The compounds 2b to 2e (see below) are synthesised analogously to the process described above for the synthesis of compound 2a.

| Int-b | Int-c | 2 | Yield % |
|---|---|---|---|
| Int-b2 | Int-c1 | 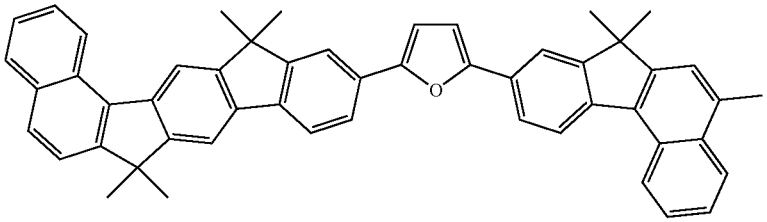 [SMILES: Cc1cc2c(c3ccccc13)-c1ccc(-c3ccc(-c4ccc5c(c4)C(C)(C)c4cc6c(cc4-5)C(C)(C)c4ccc5ccccc5c4-6)o3)cc1C2(C)C]<br>2a | 52 |
| Int-b4 | Int-c2 | 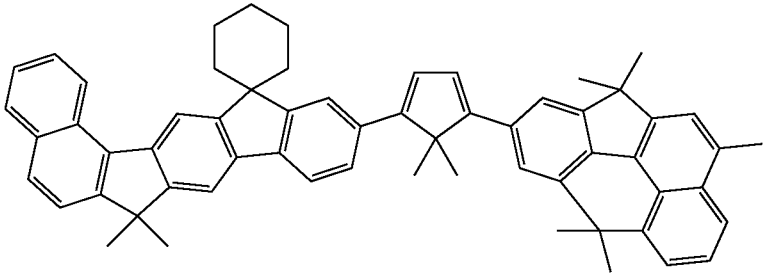 [SMILES: Cc1cc2c3c4c(cccc14)C(C)(C)c1cc(C4=CC=C(c5ccc6c(c5)C5(CCCCC5)c5cc7c(cc5-6)C(C)(C)c5ccc6ccccc6c5-7)C4(C)C)cc(c1-3)C2(C)C]<br>2b | 43 |
| Int-b2 | Int-c3 | 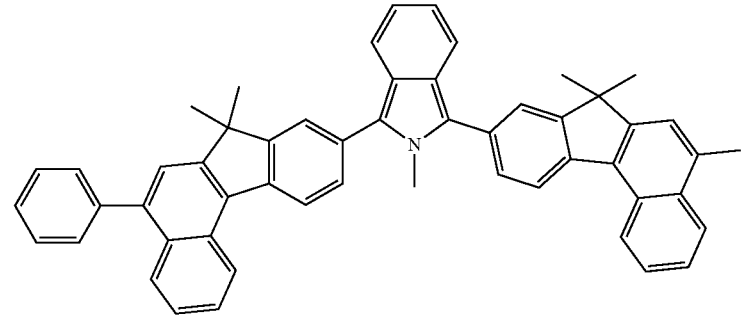 [SMILES: Cc1cc2c(c3ccccc13)-c1ccc(-c3c4ccccc4c(-c4ccc5c(c4)C(C)(C)c4cc(-c6ccccc6)c6ccccc6c4-5)n3C)cc1C2(C)C]<br>2c | 38 |
| Int-b5 | Int-c4 | 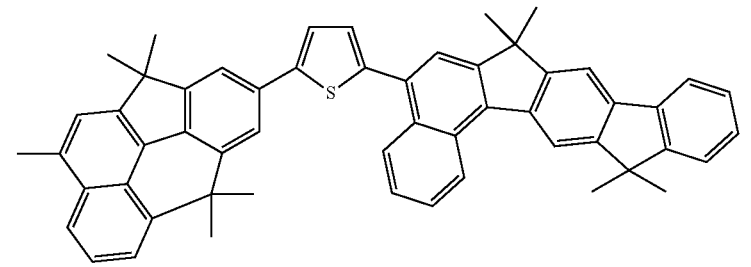 [SMILES: Cc1cc2c3c4c(cccc14)C(C)(C)c1cc(-c4ccc(-c5cc6c(c7ccccc57)-c5cc7c(cc5C6(C)C)-c5ccccc5C7(C)C)s4)cc(c1-3)C2(C)C]<br>2d | 56 |
| Int-b3 | Int-c1 | 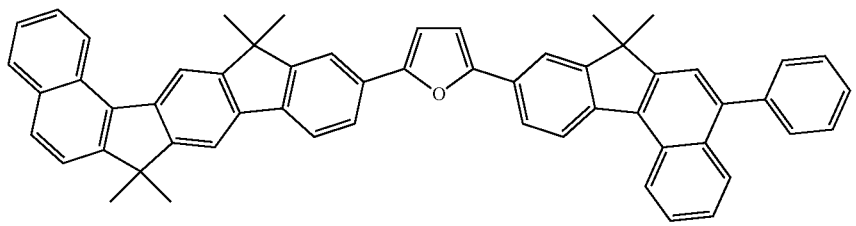 [SMILES: CC1(C)c2cc(-c3ccc(-c4ccc5c(c4)C(C)(C)c4cc(-c6ccccc6)c6ccccc6c4-5)o3)ccc2-c2cc3c(cc21)-c1c(ccc2ccccc12)C3(C)C]<br>2e | 51 |

B) Device Examples: Production of OLEDs

OLEDs according to the invention and OLEDs in accordance with the prior art are produced by a general process in accordance with WO 2004/058911, which is adapted to the circumstances described here (layer-thickness variation, materials).

The data for various OLEDs comprising a compound according to the invention (E1 to E5) or a compound according to the prior art (V1 to V3) are presented below (see Tables 1 to 3). The substrates used are glass plates coated with structured ITO (indium tin oxide) in a thickness of 50 nm. The OLEDs basically have the following layer structure: substrate/Buffer/hole-injection layer (95% HTL1+5% HIL, 20 nm)/hole-transport layer (HTL2, 195 nm)/emission layer (20 nm)/electron-transport layer (ETL, 20 nm)/electron-injection layer (EIL, 3 nm) and finally a cathode. The cathode is formed by an aluminium layer with a thickness of 100 nm. The buffer layer consists of 20 nm thick Clevios P VP Al 4083 (Heraues Clevios GmbH, Leverkusen), which is processed from solution by spin-coating. All other materials are applied by thermal vapour deposition in a vacuum chamber. The precise structure of the OLEDs is shown in Table 1. The materials required for the production of the OLEDs are shown in Table 3.

The emission layer here always consists of at least one matrix material (host material) and an emitting dopant (emitter), which is admixed with the matrix material or matrix materials in a certain proportion by volume by co-evaporation. An expression such as H1:D1 (97%:3%) here means that material H1 is present in the layer in a proportion by volume of 97% and D1 is present in the layer in a proportion of 3%. Analogously, the electron-transport layer may also consist of a mixture of two materials.

The OLEDs are characterised by standard methods. For this purpose, the electroluminescence spectra, the current efficiency (measured in cd/A), the power efficiency (measured in lm/W), the external quantum efficiency (EQE, measured in percentage) as a function of the luminous density as calculated from current/voltage/luminous density characteristic lines (IUL characteristic lines) assuming Lambert emission characteristics, and the lifetime are determined. The electroluminescence spectra are determined at a luminous density of 1000 cd/m², and the CIE 1931 x and y colour coordinates are calculated therefrom. The expression EQE @ 1000 cd/m² denotes the external quantum efficiency at an operating luminous density of 1000 cd/m². LT95 @ 1000 cd/m² is the lifetime until the OLED has dropped from a luminance of 1000 cd/m² to 95% of the initial intensity, i.e. to 950 cd/m². The data for the various OLEDs are summarised in Table 2.

Use of Compounds According to the Invention as Emitter Material in Fluorescent OLEDs In particular, compounds according to the present invention are suitable as fluorescent blue dopants (emitter) in OLEDs when mixed into a host material (matrix). In comparison with present state-of-the-art dopants (reference VD1, VD2) the samples comprising the compounds according to the invention are highly efficient and exhibit a significantly improved lifetime.

TABLE 1

Structure of the OLEDs

| Experiment | EML |
|---|---|
| V1 | H1(97%):VD1(3%) |
| V2 | H2(97%):VD1(3%) |
| V3 | H1(97%):VD2(3%) |
| E1 | H1(97%):D1(3%) |
| E2 | H2(97%):D1(3%) |
| E3 | H1(97%):D2(3%) |
| E4 | H2(97%):D2(3%) |
| E5 | H1(97%):D3(3%) |

TABLE 2

Data for the OLEDs

| Ex. | EQE @ 1000 cd/m2 % | LT95 @ 1000 cd/m² [h] | CIE x | CIE y |
|---|---|---|---|---|
| V1 | 7.8 | 110 | 0.13 | 0.13 |
| V2 | 7.5 | 90 | 0.13 | 0.14 |
| V3 | 8.0 | 90 | 0.13 | 0.16 |
| E1 | 8.1 | 160 | 0.15 | 0.18 |
| E2 | 8.0 | 150 | 0.14 | 0.16 |
| E3 | 8.3 | 180 | 0.15 | 0.17 |
| E4 | 8.1 | 130 | 0.14 | 0.16 |
| E5 | 8.3 | 150 | 0.14 | 0.14 |

TABLE 3

Structures of the materials used

HIL

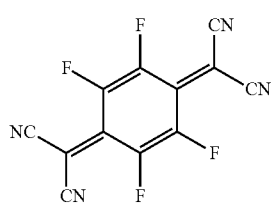 [SMILES: N#CC(C#N)=c1c(F)c(F)c(=C(C#N)C#N)c(F)c1F]

TABLE 3-continued
Structures of the materials used
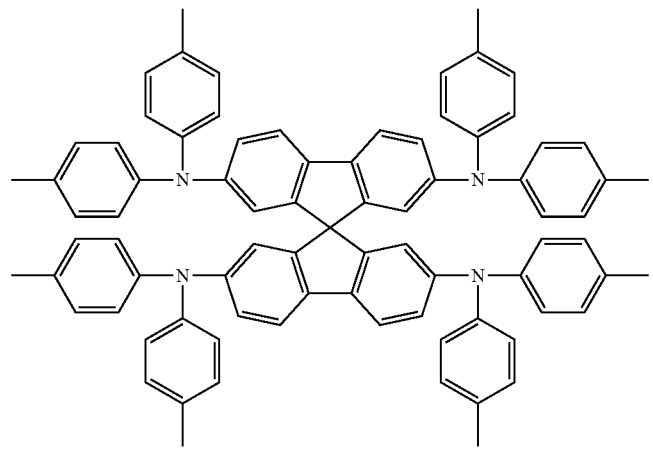
HTL1
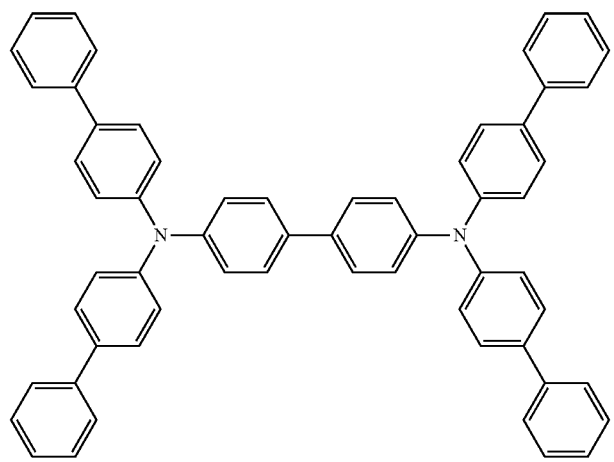 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1]
HTL2
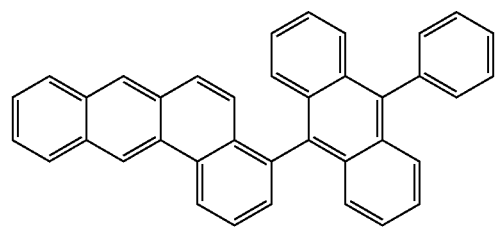 [SMILES: c1ccc(-c2c3ccccc3c(-c3cccc4c3ccc3cc5ccccc5cc34)c3ccccc23)cc1]
H1
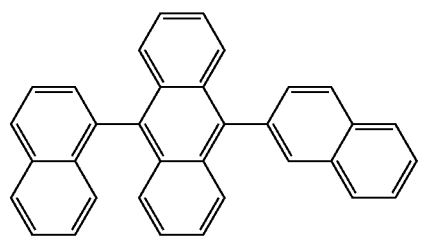 [SMILES: c1ccc2cc(-c3c4ccccc4c(-c4cccc5ccccc45)c4ccccc34)ccc2c1]
H2

TABLE 3-continued
Structures of the materials used
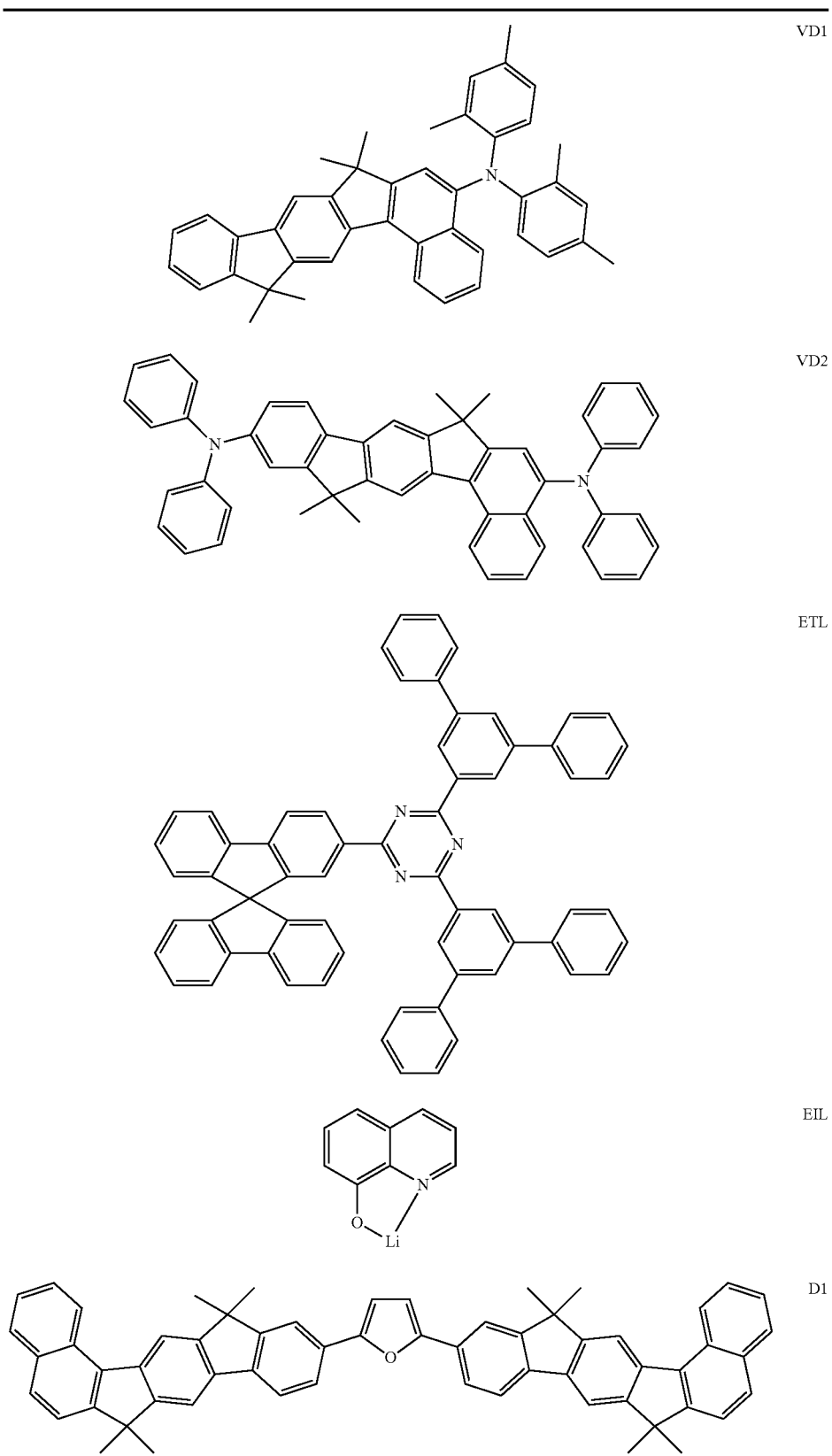

TABLE 3-continued

Structures of the materials used

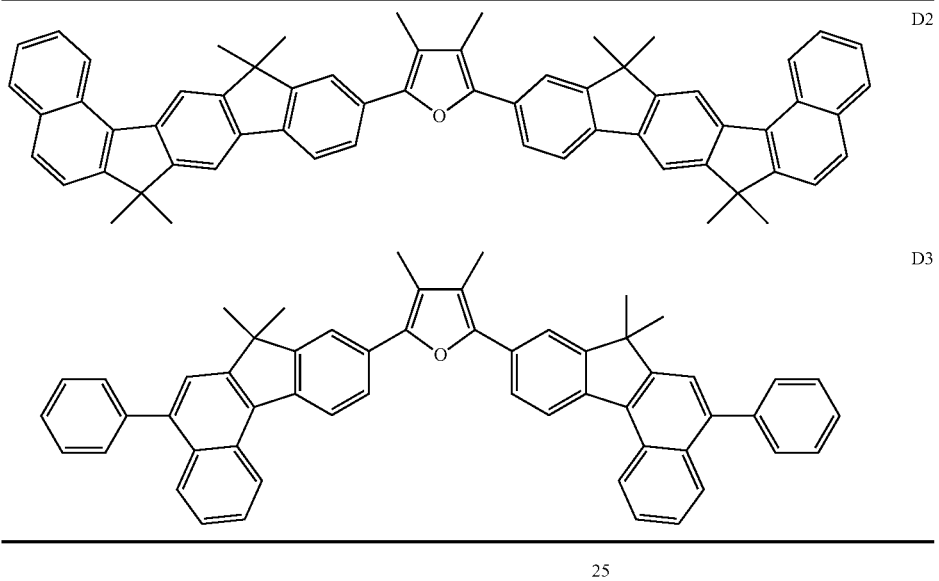

D2

D3

The invention claimed is:
1. A compound of formula (I) or formula (II):

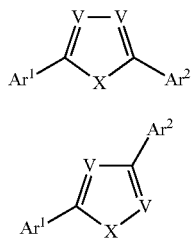

wherein
X is selected from the group consisting of $C(R^1)_2$, $Si(R^1)_2$, $Ge(R^1)_2$, O, S, $NR^1$, and Se;
V is, on each occurrence, identically or differently, selected from the group consisting of N or $CR^2$;
$Ar^1$ and $Ar^2$
are, identically or differently, selected from group consisting of formulae (3) through (8):

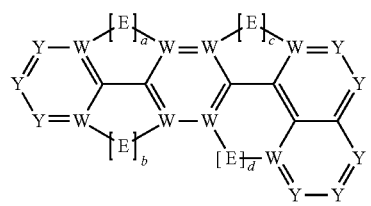

formula (3)

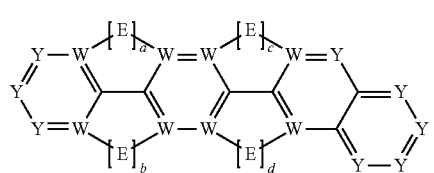

formula (4)

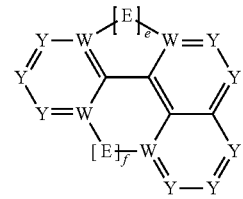

formula (5)

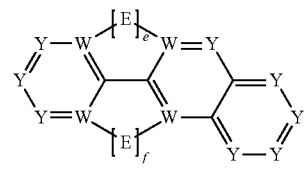

formula (6)

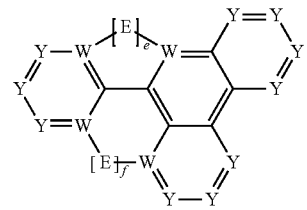

formula (7)

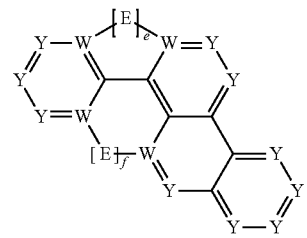

formula (8)

wherein
$Ar^1$ and $Ar^2$
are connected to the 5-membered ring of formula (I) or (II) via one group Y of one of formulae (3) through (8);

Y is C if the 5-membered ring of formula (I) or (II) is bonded to Y and is CR³ or N if the 5-membered ring of formula (I) or (II) is not bonded to the group Y;

E is, on each occurrence, identically or differently, a divalent bridge selected from the group consisting of B(R¹), C(R¹)₂, Si(R¹)₂, C=O, C=NR¹, C=C(R¹)₂, O, S, S=O, SO₂, N(R¹), P(R¹), and P(=O)R¹;

W is C if a bridge E is bonded to the group W and is CR³ or N if no bridge E is bonded to the group W;

R¹, R², and R³
is, on each occurrence, identically or differently, H, D, F, Br, Cl, I, C(=O)R⁴, CN, Si(R⁴)₃, N(R⁴)₂, P(=O)(R⁴)₂, S(=O)R⁴, S(=O)₂R⁴, a straight-chain alkyl or alkoxy group having 1 to 20 C atoms or a branched or cyclic alkyl or alkoxy group having 3 to 20 C atoms or an alkenyl or alkynyl group having 2 to 20 C atoms, wherein these groups are each optionally substituted by one or more radicals R⁴ and wherein one or more CH₂ groups in these groups are optionally replaced by —R⁴C=CR⁴—, —C≡C—, Si(R⁴)₂, C=O, C=NR⁴, —C(=O)O—, —C(=O)NR⁴—, NR⁴, P(=O)(R⁴), —O—, —S—, SO, or SO₂, an aromatic or heteroaromatic ring system having 5 to 30 aromatic ring atoms, which in each case is optionally substituted by one or more radicals R⁴, or an aryloxy or heteroaryloxy group having 5 to 30 aromatic ring atoms, which is optionally substituted by one or more radicals R⁴, and wherein two or more substituents R¹, two or more substituents R², or two or more substituents R³ are optionally linked to one another so as to define a ring;

R⁴ is on each occurrence, identically or differently, H, D, F, Br, Cl, I, C(=O)R⁵, CN, Si(R⁵)₃, N(R⁵)₂, P(=O)(R⁵)₂, S(=O)R⁵, S(=O)₂R⁵, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where these groups are each optionally substituted by one or more radicals R⁵ and wherein one or more CH₂ groups in these groups are optionally replaced by —R⁵C=CR⁵—, —C≡C—, Si(R⁵)₂, C=O, C=NR⁵, —C(=O)O—, —C(=O)NR⁵—, NR⁵, P(=O)(R⁵), —O—, —S—, SO, or SO₂, an aromatic or heteroaromatic ring system having 5 to 30 aromatic ring atoms, which in each case is optionally substituted by one or more radicals R⁵, or an aryloxy or heteroaryloxy group having 5 to 30 aromatic ring atoms, which is optionally substituted by one or more radicals R⁵, and wherein two or more radicals R⁴ are optionally linked to one another so as to define a ring;

R⁵ is on each occurrence, identically or differently, H, D, F, or an aliphatic, aromatic, or heteroaromatic organic radical having 1 to 20 C atoms, wherein one or more H atoms are optionally replaced by D or F; and a, b, c, d, e, and f
are, on each occurrence, identically or differently, 0 or 1, with the proviso that a +b =1 or 2, c +d =1 or 2, and e +f =1 or 2, wherein when a =0, or b =0, or c =0, or d 0, or e =0, or f=0, in each case the corresponding bridge X is not present.

2. The compound of claim 1, wherein a +b =1, c +d =1, and e +f =1 or 2.

3. The compound of claim 1, wherein X is selected from C(R¹)₂, Si(R¹)₂, O, or S.

4. The compound of claim 1, wherein E is, on each occurrence, identically or differently, a divalent bridge selected from the group consisting of C(R¹)₂, Si(R¹)₂, O, S, and N(R¹), more preferably C(R¹)₂.

5. The compound of claim 1, wherein E is C(R¹)₂.

6. The compound of claim 1, wherein V is CR².

7. The compound of claim 1, wherein
Ar¹ and Ar²
are, identically or differently, selected from one of formulae (3-1) through (8-3):

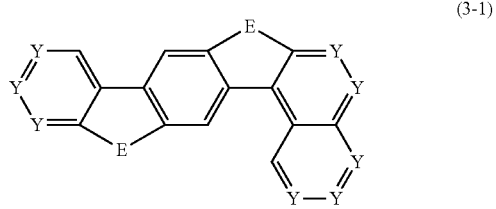
(3-1)

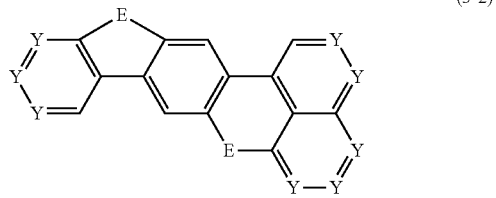
(3-2)

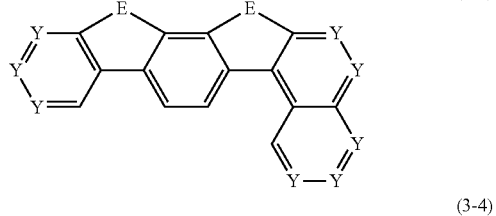
(3-3)

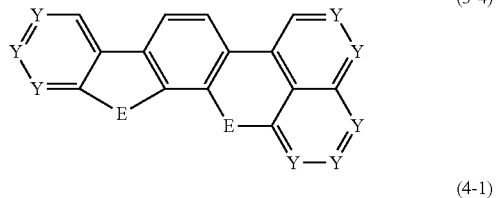
(3-4)

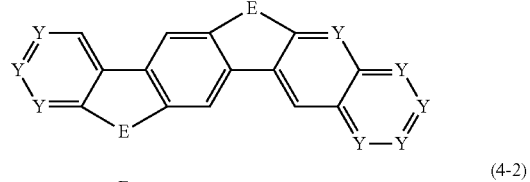
(4-1)

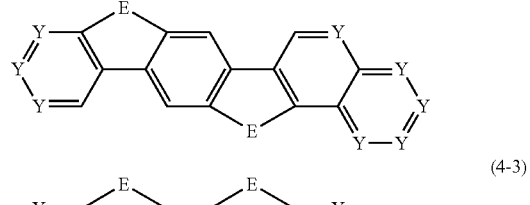
(4-2)

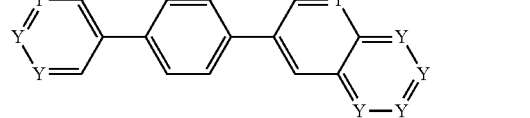
(4-3)

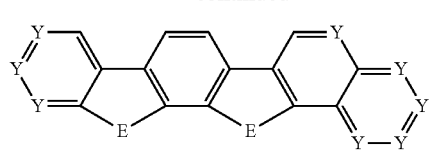
(4-4)
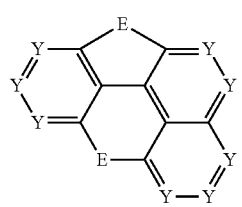
(5-1)
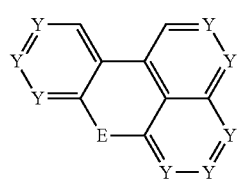
(5-2)
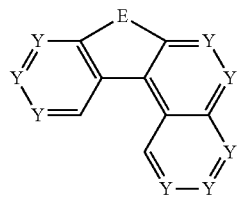
(5-3)
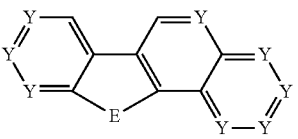
(6-1)
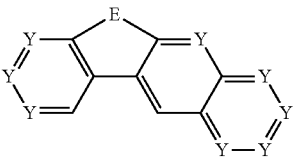
(6-2)
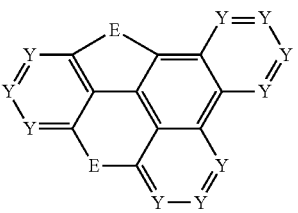
(6-3)
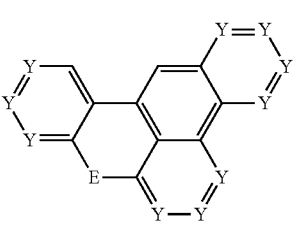
(7-1)
(7-2)
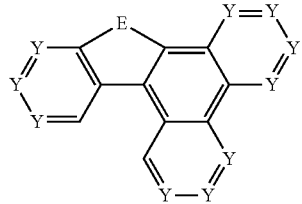
(7-3)
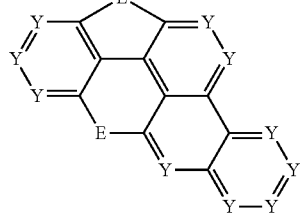
(8-1)
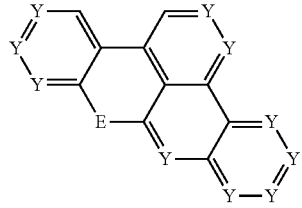
(8-2)
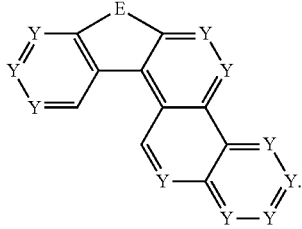
(8-3)
8. The compound of claim 1, wherein
$Ar^1$ and $Ar^2$
are, identically or differently, selected from one of the following formulae (3-1-1) to (8-3-2):
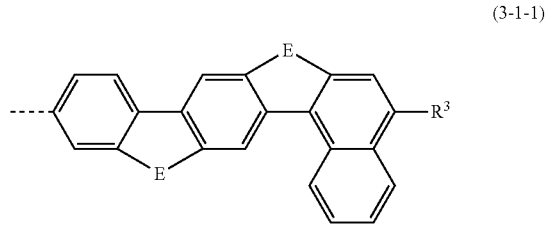
(3-1-1)
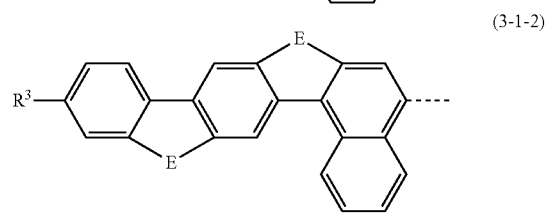
(3-1-2)

(3-2-1)
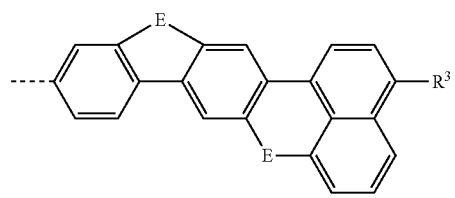
(3-2-2)
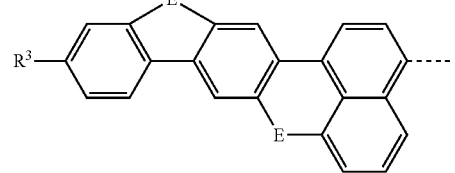
(3-4-1)
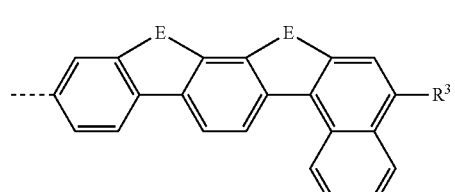
(3-4-2)
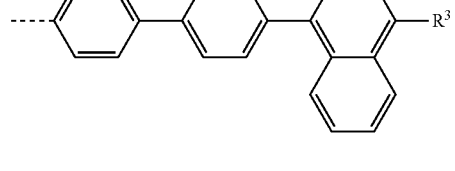
(4-1-1)
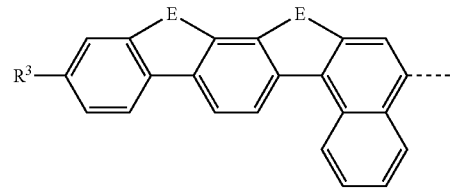
(4-1-2)
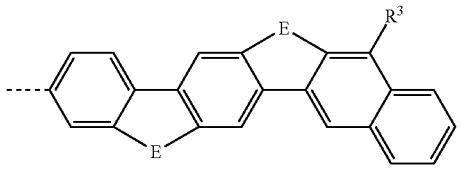
(4-2-1)
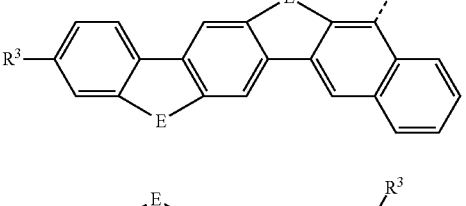
(4-2-2)
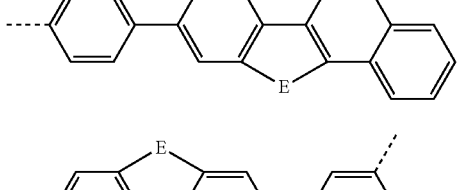
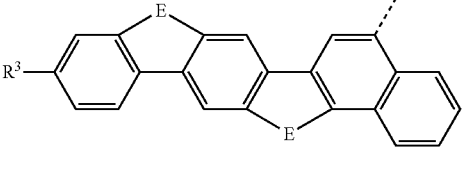
(4-3-1)
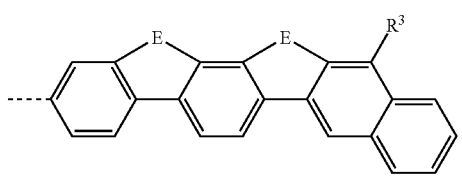
(4-3-2)
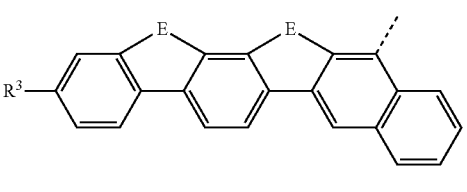
(4-4-1)
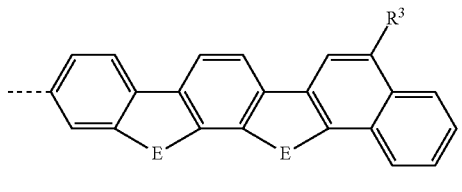
(4-4-2)
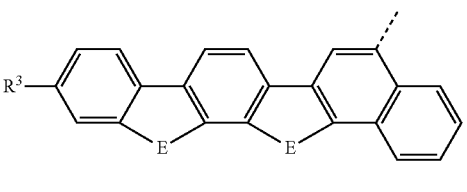
(5-1-1)
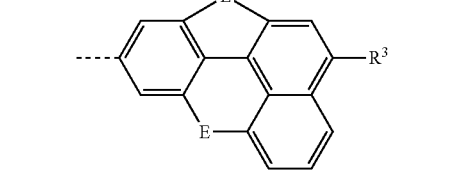
(5-1-2)
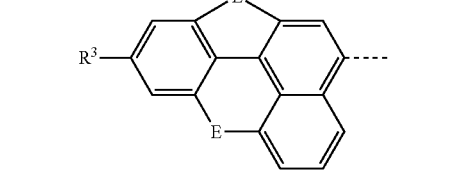
(5-2-1)
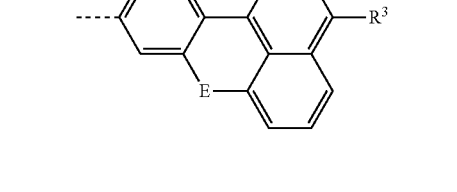
(5-2-2)
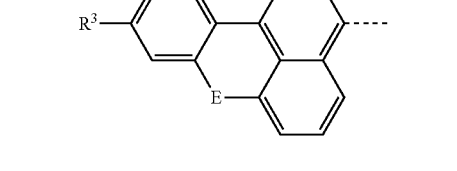

(5-3-1)
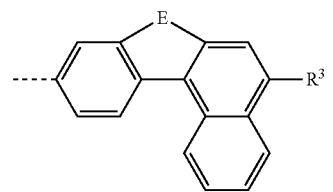
(5-3-2)
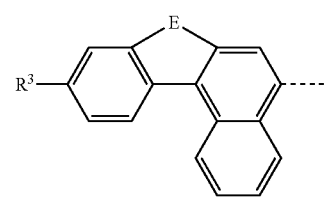
(6-1-1)
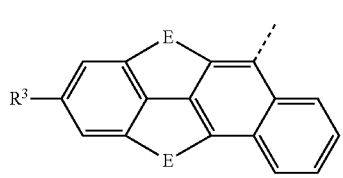
(6-1-2)
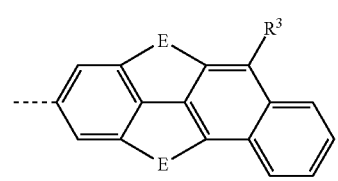
(6-2-1)
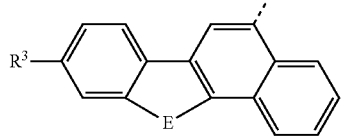
(6-2-2)
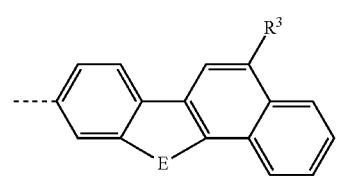
(6-3-1)
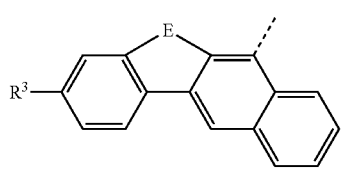
(6-3-2)
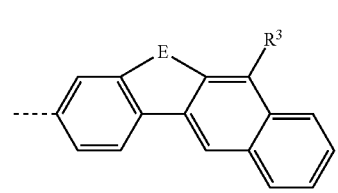
(7-1-1)
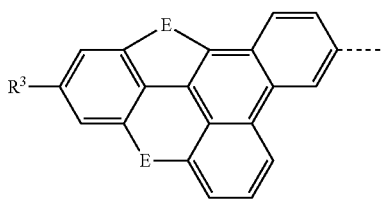
(7-1-2)
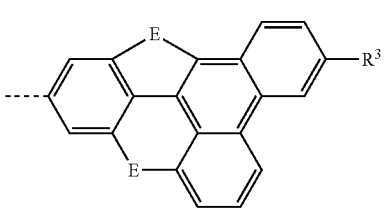
(7-2-1)
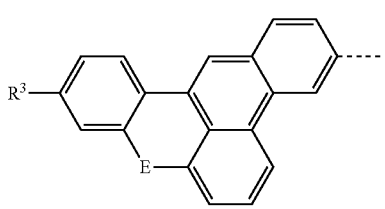
(7-2-2)
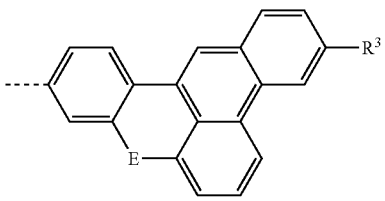
(7-3-1)
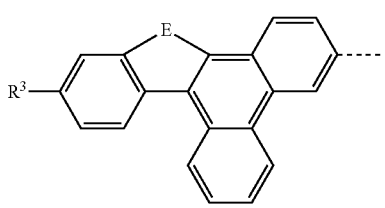
(7-3-2)
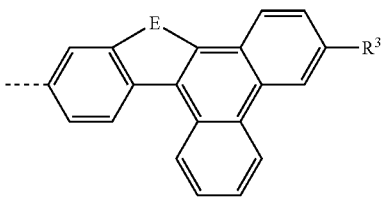
(8-1-1)
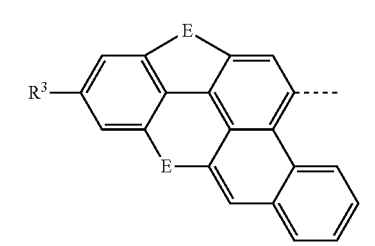

-continued
(8-1-2)
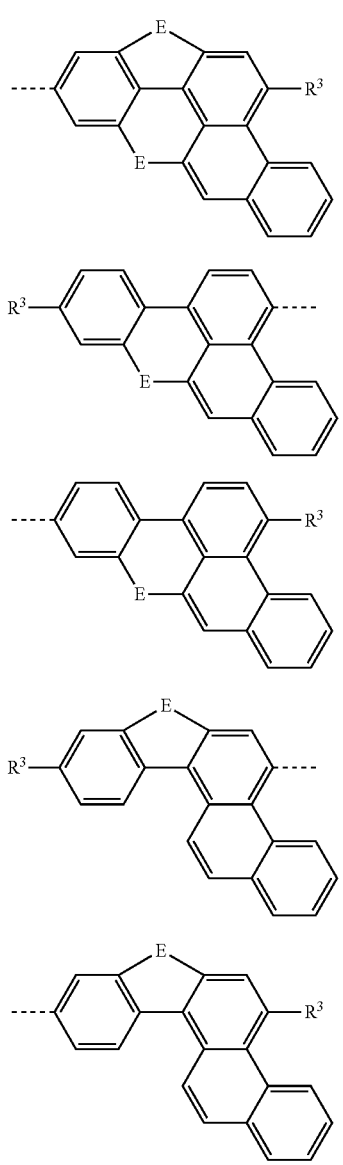
(8-2-1)
(8-2-2)
(8-3-1)
(8-3-2)
wherein the dashed lines represent the bonds to the 5-membered ring of formula (I) or (II).
9. The compound of claim 1, wherein it is a compound of formula (I) or formula (II):
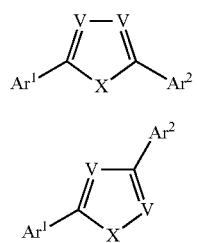
(I)
(II)
wherein
X is $C(R^1)_2$, $Si(R^1)_2$, O, or S;
V is $CR^2$;
$Ar^1$ and $A^2$ is, identically or differently, selected from the group consisting of formulae (3-1) through (8-3):
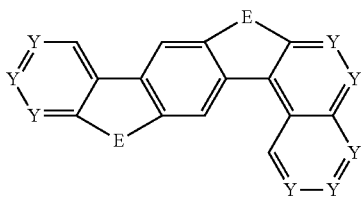
(3-1)
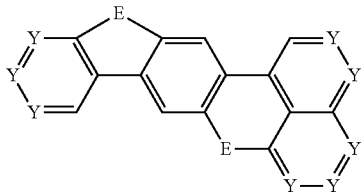
(3-2)
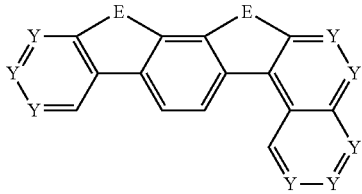
(3-3)
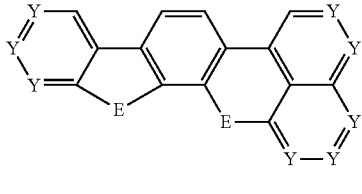
(3-4)
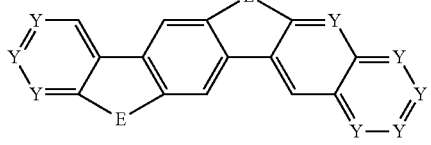
(4-1)
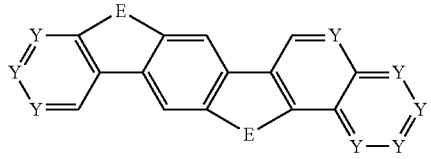
(4-2)
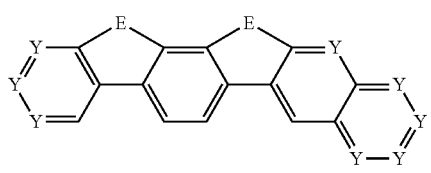
(4-3)
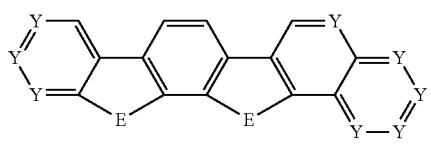
(4-4)

-continued

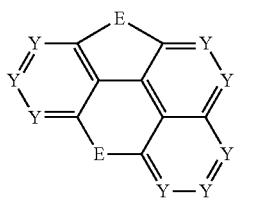
(5-1)

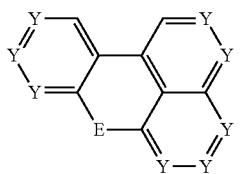
(5-2)

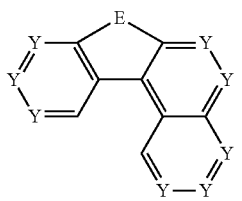
(5-3)

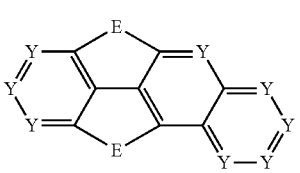
(6-1)

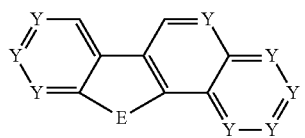
(6-2)

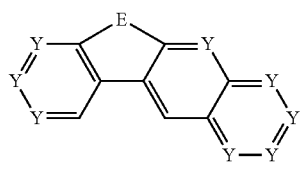
(6-3)

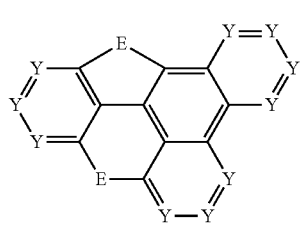
(7-1)

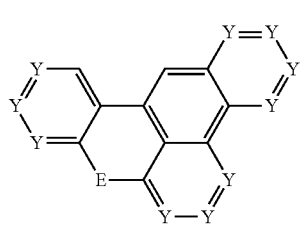
(7-2)

-continued

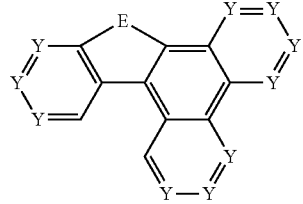
(7-3)

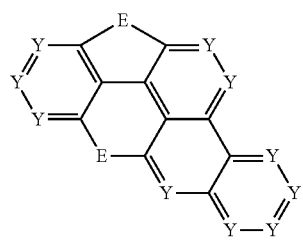
(8-1)

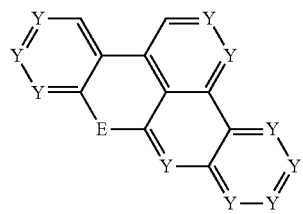
(8-2)

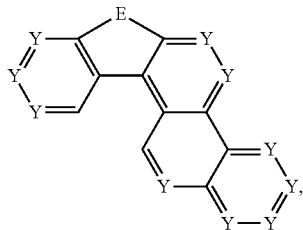
(8-3)

wherein E is $C(R^1)_2$ and Y is C if the 5-membered ring of formula (I) or (II) is bonded to Y and $CR^3$ otherwise;

$R^1$, $R^2$, and $R^3$ is on each occurrence, identically or differently, H, D, F, CN, $Si(R^4)_3$, $N(R^4)_2$, a straight-chain alkyl or alkoxy group having 1 to 10 C atoms or a branched or cyclic alkyl or alkoxy group having 3 to 10 C atoms, where these groups are each optionally substituted by one or more radicals $R^4$ and wherein one or more $CH_2$ groups in these groups are optionally replaced by —C≡C—, —$R^4$C=C$R^4$—, $Si(R^4)_2$, C=O, C=N$R^4$, —N$R^4$—, —O—, —S—, —C(=O)O—, or —C(=O)N$R^4$—, an aromatic or heteroaromatic ring system having 5 to 20 aromatic ring atoms, which in each case is optionally substituted by one or more radicals $R^4$, and wherein two radicals $R^1$ are optionally linked to one another so as to define a ring, two radicals $R^2$ are optionally linked to one another so as to define a ring, or two radicals $R^3$ are optionally linked to one another so as to define a ring; and $R^4$ is on each occurrence, identically or differently, H, D, F, CN, $Si(R^5)_3$, $N(R^5)_2$, a straight-chain alkyl or alkoxy group having 1 to 10 C atoms or a branched or cyclic alkyl or alkoxy group having 3 to 10 C atoms, where these groups are each optionally substituted by one or more radicals $R^5$ and wherein one or more $CH_2$ groups in these groups are optionally replaced by —C≡C—, —$R^5$C=C$R^5$—, $Si(R^5)_2$, C=O, C=N$R^5$, —N$R^5$—, —O—, —S—, —C(=O)O—, or —C(=O)NR$^5$—, or an aromatic or heteroaromatic ring system having 5 to 20 aromatic ring atoms, which in each case is optionally substituted by one or more radicals R$^5$, and wherein two or more radicals R$^4$ are optionally linked to one another so as to define a ring.

10. An oligomer, polymer, or dendrimer comprising one or more compounds of claim 1, wherein the bond(s) to the polymer, oligomer, or dendrimer are optionally localised at any desired position(s) in formula (I) or (II) which are substituted by R$^1$, R$^2$, or R$^3$.

11. A formulation comprising at least one compound of claim 1 and at least one solvent.

12. A formulation comprising at least one polymer, oligomer, or dendrimer of claim 10 and at least one solvent.

13. An electronic device comprising at least one compound of claim 1, wherein the electronic device is selected from the group consisting of organic integrated circuits, organic field-effect transistors, organic thin-film transistors, organic light-emitting transistors, organic solar cells, organic optical detectors, organic photoreceptors, organic field-quench devices, organic light-emitting electrochemical cells, organic laser diodes, and organic electroluminescent devices.

14. The electronic device of claim 13, wherein the electronic device is an organic electroluminescent device, wherein the organic electroluminescent device comprises an anode, a cathode, and at least one emitting layer, and wherein at least one layer of the electronic device selected from the group consisting of emitting layers, electron-transport layers, electron-injection layers, and hole-blocking layers, comprises the at least one compound.

15. The electronic device of claim 13, wherein the electronic device comprises a compound of claim 1, wherein the compound is a fluorescent compound and is present in an emitting layer.

16. A process for preparing a compound of claim 1, comprising reacting a 5-membered ring boronic ester derivative and a halogenated aromatic or heteroaromatic group via a C—C Suzuki coupling reaction.

* * * * *